(12) United States Patent
He et al.

(10) Patent No.: US 7,094,782 B1
(45) Date of Patent: Aug. 22, 2006

(54) AZOLO TRIAZINES AND PYRIMIDINES

(75) Inventors: Liqi He, West Chester, PA (US); Paul Gilligan, Wilmington, DE (US); Robert Chorvat, West Chester, PA (US); Argyrios Georgios Arvanitis, Kennett Square, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 390 days.

(21) Appl. No.: 10/703,235

(22) Filed: Nov. 7, 2003

Related U.S. Application Data

(60) Continuation of application No. 09/930,782, filed on Aug. 16, 2001, now abandoned, which is a division of application No. 09/014,734, filed on Jan. 28, 1998, now Pat. No. 6,313,124.

(60) Provisional application No. 60/023,290, filed on Jul. 24, 1996.

(51) Int. Cl.
  A61K 31/53 (2006.01)
  C07D 487/04 (2006.01)
  C07D 251/72 (2006.01)
(52) U.S. Cl. ..................... 514/246; 544/263
(58) Field of Classification Search ............. 514/246; 544/263
  See application file for complete search history.

(56) References Cited

U.S. PATENT DOCUMENTS

| | | | |
|---|---|---|---|
| 3,910,907 A | 10/1975 | O'Brien et al. | 514/212 |
| 3,920,652 A | 11/1975 | Springer et al. | 544/281 |
| 3,995,039 A | 11/1976 | Rooney et al. | 514/246 |
| 4,021,556 A | 5/1977 | Springer et al. | 514/259.3 |
| 4,567,263 A | 1/1986 | Eicken et al. | 544/263 |
| 4,892,576 A | 1/1990 | Kruger et al. | 504/133 |
| 4,990,647 A | 2/1991 | Himmler et al. | 558/414 |
| 4,997,940 A | 3/1991 | Vinogradoff et al. | 544/281 |
| 5,089,499 A | 2/1992 | Barker et al. | 514/266.3 |
| 5,137,887 A | 8/1992 | Hashimoto et al. | 514/246 |
| 5,250,534 A | 10/1993 | Bell et al. | 514/252.16 |
| 5,397,774 A | 3/1995 | Nugent et al. | 514/81 |
| 5,428,044 A | 6/1995 | Bantick et al. | 514/341 |
| 5,463,051 A | 10/1995 | Himmelsbach et al. | 548/251 |
| 5,464,847 A | 11/1995 | Courtemanche et al. | 514/342 |
| 5,484,760 A | 1/1996 | Bussler et al. | 504/103 |
| 5,486,531 A | 1/1996 | Schonafinger et al. | 514/364 |
| 5,723,608 A | 3/1998 | Yuan | 544/118 |
| 6,124,289 A * | 9/2000 | He et al. | 514/245 |

FOREIGN PATENT DOCUMENTS

| | | |
|---|---|---|
| DE | 4243279 | 12/1992 |
| EP | 0 244 097 | 4/1987 |
| EP | 0 269 859 | 6/1988 |
| EP | 0 300 688 | 1/1989 |
| EP | 0 373 891 | 12/1989 |
| EP | 0 374 448 | 6/1990 |
| EP | 0 395 144 | 10/1990 |
| EP | 0 455 545 | 11/1991 |
| EP | 0 503 099 | 9/1992 |
| EP | 0 521 622 | 1/1993 |
| EP | 0 531 901 | 3/1993 |
| EP | 0 576 350 | 12/1993 |
| EP | 0 591 528 | 4/1994 |
| EP | 0 594 149 | 4/1994 |
| EP | 0 714 898 | 6/1995 |
| EP | 0 662 477 | 7/1995 |
| EP | 0 729 758 | 9/1996 |
| EP | 0 773 023 | 5/1997 |
| EP | 0 778 277 | 6/1997 |
| EP | 0 812 831 | 12/1997 |
| JP | 4211753 | 7/1967 |
| JP | 6157587 | 3/1986 |
| JP | 9535298 | 2/1996 |
| WO | WO92/10098 | 6/1992 |
| WO | WO92/20642 | 11/1992 |
| WO | WO93/07149 | 4/1993 |
| WO | WO94/09017 | 4/1994 |

(Continued)

OTHER PUBLICATIONS

Senga et al, Chemical Abstracts, vol. 96, Entry 181036s (1982).

(Continued)

*Primary Examiner*—James O. Wilson
*Assistant Examiner*—Tamthom N. Truong
(74) *Attorney, Agent, or Firm*—Shah R. Makujina; Woodcock Washburn, LLP

(57) ABSTRACT

Corticotropin releasing factor (CRF) antagonists of formula I or II:

and their use in treating anxiety, depression, and other psychiatric, neurological disorders as well as treatment of immunological, cardiovascular or heart-related diseases and colonic hypersensitivity associated with psychopathological disturbance and stress.

1 Claim, No Drawings

FOREIGN PATENT DOCUMENTS

| | | |
|---|---|---|
| WO | WO94/13643 | 6/1994 |
| WO | WO94/13644 | 6/1994 |
| WO | WO94/13661 | 6/1994 |
| WO | WO94/13676 | 6/1994 |
| WO | WO94/13677 | 6/1994 |
| WO | WO95/11880 | 5/1995 |
| WO | WO95/32710 | 12/1995 |
| WO | WO95/33727 | 12/1995 |
| WO | WO95/33750 | 12/1995 |
| WO | WO95/34563 | 12/1995 |
| WO | WO96/19452 | 6/1996 |
| WO | WO96/23783 | 8/1996 |
| WO | WO96/35689 | 11/1996 |
| WO | WO96/39388 | 12/1996 |
| WO | WO96/39400 | 12/1996 |
| WO | WO97/00868 | 1/1997 |
| WO | WO97/14684 | 4/1997 |
| WO | WO97/29109 | 8/1997 |
| WO | WO97/29110 | 8/1997 |
| WO | WO 98/03510 | 1/1998 |
| WO | WO98/08821 | 3/1998 |
| WO | WO98/08846 | 3/1998 |
| WO | WO98/08847 | 3/1998 |

OTHER PUBLICATIONS

O'Brien et al, Chemical Abstracts, vol. 84, Entry 44171n (1976).
Hungarian Novelty Search Report dated Oct. 2, 2002 (P0102187).
Arch. Pharma (Weinheim) 320, 487-491 (1987), Ibrahim et al.
Psychopharmacology (Britton, Lee, Koob) 94:306-311 (1988).
Life Sciences (Britton, Koob, Rivier, Vale) 31:363-367 (1982).
Bull. Soc. Chim, Belg. (Maquestiau, Taghret, Enyde) vol. 101/No. 2/1992.
Corticotropin-Releasing Factor: Basic and Clinical Studies of a Neuropeptide (DeSouza, Nemeroff) 221-224, 1990.
J. Med. Chem (Senga, et al.) 25:243-249 (1982).
Comprehensive Organic Synthesis (Trost, Fleming) 3:481-520, 1991.
Synapse (Battaglia, Webster, DeSouza) 1:572-581 (1987).
Science (Nemeroff, et al.) 226:1342 (1984).
Remington's Pharmaceutical Sciences (Gennardo, ed.) 17th ed. P. 1418-1419, 1985.
Brain Research Reviews (Dunn, Berridge) 15:71-100 (1990).
Proc. Natl. Acad. Sci. (Rivier, Spiess, Vale) 80:4851-4855 (1983).
Recent Progress in Hormone Research (Vale, et al.) 39:245-271 (1983).
Journal of Neuroscience (DeSouza, et al.) Vo. 5, No. 12, P. 3189-3203 (1985).
Perspectives on Behavioral Medicine (Koob) 2:39-52 (1985).
Biol. Psychiatry (France, et al.) 23:86-88 (1988).
Hormones and Behavior (Berridge, Dunn) 21:393-401 (1987).
Hospital Practice (De Souza) p. 59-71 (1988).
Arch. Gen Psychiatry (Sapolsky) 46:1047-1051 (1989).
Psychopharmacology (Britton, et al.) 86:170-174 (1985).
Biol. Psychiatry (Arato, et al.) 25:355-359 (1989).
Regulatory Peptides (Berridge, Dunn) 16 83-93 (1986).
Neuropsychopharmacology (Grigoriadis, et al.) Vo. 2, No. 1, p. 53-60 (1989).
Psychopharmacology (Swerdlow, Geyer, Vale, Koob) 88:147-152 (1986).
Am. J. Psychiatry (Banki et al.) 144:873-877 (1987).
Arch. Gen. Psychiatry (Nemeroff, et al.) 45:577-579 (1988).
New Eng. J. Med. (Gold, et al.) vol. 314, No. 21, p. 1329-1335 (1986).
Life Sciences (Morley, et al.) 41:527-544 (1987).
Physiological Reviews (Blalock) Vo. 69, No. 1, p. 1-33 (1989).
Journal f. prakt. Chemie. (Joshi, Dubey) Band 321, Heft 2, p. 341-344 (1979).
Journal of Medicinal Chemistry (Springer et al.) vol. 19, No. 2, p. 291-296 (1976).
J. Heterocyclic Chem. (O'Brien et al.) 22:601-634 (1985).
J. Med. Chem (Senga, Novinson, Wilson) 24:610-613 (1981).
Science (Vale, et al.) 213:1394-1397 (1981).
Chemical Abstracts, vol. 67, No. 28, 1967, abstract #108663r, Takamizawa et al.
Chemical Abstracts, vol. 74, No. 28, 1971, abstract #22867t, Takamizawa et al.
Chemical abstracts, vol. 74, No. 28, 1971, abstract #22872r, Takamizawa et al.
Chemical abstracts, vol. 68, No. 28, 1968, abstract 114635v, Takamizawa et al.

* cited by examiner

AZOLO TRIAZINES AND PYRIMIDINES

CROSS-REFERENCE TO RELATED APPLICATIONS

The present application is a continuation of Ser. No. 09/930,782, filed on Aug. 16, 2001 now abandoned, which is a divisional of Ser. No. 09/014,734, filed Jan. 28, 1998, now U.S. Pat. No. 6,313,124, and claims benefit of Ser. No. 60/023,290, filed Jul. 24, 1996, the contents all of which are incorporated herein by reference.

FIELD OF THE INVENTION

This invention relates a treatment of psychiatric disorders and neurological diseases including major depression, anxiety-related disorders, post-traumatic stress disorder, supranuclear palsy and feeding disorders as well as treatment of immunological, cardiovascular or heart-related diseases and colonic hypersensitivity associated with psychopathological disturbance and stress, by administration of certain [1,5-a]pyrazolo-1,3,5-triazines, [1,5-a]-1,2,3-triazolo-1,3,5-triazines, [1,5-a]-pyrazolo-pyrimidines and [1,5-a]-1,2,3-triazolo-pyrimidines.

BACKGROUND OF THE INVENTION

Corticotropin releasing factor (herein referred to as CRF), a 41 amino acid peptide, is the primary physiological regulator of proopiomelanocortin(POMC)-derived peptide secretion from the anterior pituitary gland [J. Rivier et al., *Proc. Nat. Acad. Sci.* (*USA*) 80:4851 (1983); W. Vale et al., *Science* 213:1394 (1981)]. In addition to its endocrine role at the pituitary gland, immunohistochemical localization of CRF has demonstrated that the hormone has a broad extra-hypothalamic distribution in the central nervous system and produces a wide spectrum of autonomic, electrophysiological and behavioral effects consistent with a neurotransmitter or neuromodulator role in brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is also evidence that CRF plays a significant role in integrating the response of the immune system to physiological, psychological, and immunological stressors [J. E. Blalock, *Physiological Reviews* 69:1 (1989); J. E. Morley, *Life Sci.* 41:527 (1987)].

Clinical data provide evidence that CRF has a role in psychiatric disorders and neurological diseases including depression, anxiety-related disorders and feeding disorders. A role for CRF has also been postulated in the etiology and pathophysiology of Alzheimer's disease, Parkinson's disease, Huntington's disease, progressive supranuclear palsy and amyotrophic lateral sclerosis as they relate to the dysfunction of CRF neurons in the central nervous system [for review see E. B. De Souza, *Hosp. Practice* 23:59 (1988)].

In affective disorder, or major depression, the concentration of CRF is significantly increased in the cerebral spinal fluid (CSF) of drug-free individuals [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol Psychiatry* 25:355 (1989)]. Furthermore, the density of CRF receptors is significantly decreased in the frontal cortex of suicide victims, consistent with a hypersecretion of CRF [C. B. Nemeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am J. Psychiatry* 141:619 (1984); F. Holsboer et al., *Psychoneuroendocrinology* 9:147 (1984); P. W. Gold et al., *New Eng. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is preliminary evidence that tricyclic antidepressants can alter CRF levels and thus modulate the numbers of CRF receptors in brain [Grigoriadis et al., *Neuropsychopharmacology* 2:53 (1989)].

There has also been a role postulated for CRF in the etiology of anxiety-related disorders. CRF produces anxiogenic effects in animals and interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn *Regul. Peptides* 16:83 (1986)]. Preliminary studies using the putative CRF receptor antagonist a-helical ovine CRF (9-41) in a variety of behavioral paradigms demonstrate that the antagonist produces "anxiolytic-like" effects that are qualitatively similar to the benzodiazepines [C. W. Berridge and A. J. Dunn *Horm. Behav.* 21:393 (1987), *Brain Research Reviews* 15:71 (1990)]. Neurochemical, endocrine and receptor binding studies have all demonstrated interactions between CRF and benzodiazepine anxiolytics providing further evidence for the involvement of CRF in these disorders. Chlordiazepoxide attenuates the "anxiogenic" effects of CRF in both the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist (Ro15-1788), which was without behavioral activity alone in the operant conflict test, reversed the effects of CRF in a dose-dependent manner while the benzodiazepine inverse agonist (FG7142) enhanced the actions of CRF [K. T. Britton et al., *Psychopharmacology* 94:306 (1988)].

The mechanisms and sites of action through which the standard anxiolytics and antidepressants produce their therapeutic effects remain to be elucidated. It has been hypothesized however, that they are involved in the suppression of the CRF hypersecretion that is observed in these disorders. Of particular interest is that preliminary studies examining the effects of a CRF receptor antagonist ($\alpha$-helical $CRF_{9-41}$) in a variety of behavioral paradigms have demonstrated that the CRF antagonist produces "anxiolytic-like" effects qualitatively similar to the benzodiazepines [for review see G. F. Koob and K. T. Britton, In: *Corticotropin-Releasing Factor: Basic and Clinical Studies of a Neuropeptide*, E. B. De Souza and C. B. Nemeroff eds., CRC Press p221 (1990)].

Several publications describe corticotropin releasing factor antagonist compounds and their use to treat psychiatric disorders and neurological diseases. Examples of such publications include DuPont Merck PCT application US94/11050, Pfizer WO 95/33750, Pfizer WO 95/34563, Pfizer WO 95/33727 and Pfizer EP 0778 277 A1.

Insofar as is known, [1,5-a]-pyrazolo-1,3,5-triazines, [1,5-a]-1,2,3-triazolo-1,3,5-triazines, [1,5-a]-pyrazolo-pyrimidines and [1,5-a]1,2,3-triazolo-pyrimidines, have not been previously reported as corticotropin releasing factor antagonist compounds useful in the treatment of psychiatric disorders and neurological diseases. However, there have been publications which teach some of these compounds for other uses.

For instance, EP 0 269 859 (Ostuka, 1988) discloses pyrazolotriazine compounds of the formula:

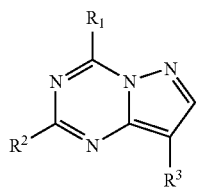

where $R^1$ is OH or alkanoyl, $R^2$ is H, OH, or SH, and $R^3$ is an unsaturated heterocyclic group, naphthyl or substituted phenyl, and states that the compounds have xanthine oxidase inhibitory activity and are useful for treatment of gout.

EP 0 594 149 (Ostuka, 1994) discloses pyrazolotriazine and pyrazolopyrimidine compounds of the formula:

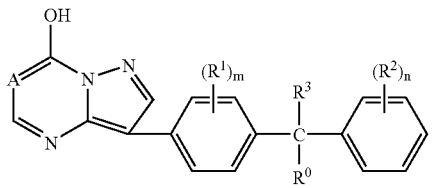

where A is CH or N, $R^0$ and $R^3$ are H or alkyl, and $R^1$ and $R^2$ are H, alkyl, alkoxyl, alkylthio, nitro, etc., and states that the compounds inhibit androgen and are useful in treatment of benign prostatic hypertrophy and prostatic carcinoma.

U.S. Pat. No. 3,910,907 (ICI, 1975) discloses pyrazolotriazines of the formula:

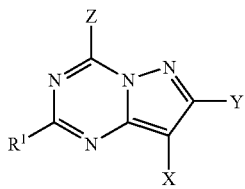

where R1 is $CH_3$, $C_2H_5$ or $C_6H_5$, X is H, $C_6H_5$, m-$CH_3C_6H_4$, CN, COOEt, Cl, I or Br, Y is H, $C_6H_5$, o-$CH_3C_6H_4$, or p-$CH_3C_6H_4$, and Z is OH, H, $CH_3$, $C_2H_5$, $C_6H_5$, n-$C_3H_7$, i-$C_3H_7$, SH, $SCH_3$, $NHC_4H_9$, or $N(C_2H_5)_2$, and states that the compounds are c-AMP phosphodiesterase inhibitors useful as bronchodilators.

U.S. Pat. No. 3,995,039 discloses pyrazolotriazines of the formula:

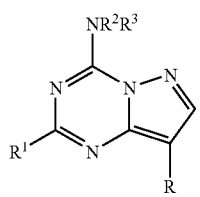

where $R^1$ is H or alkyl, $R^2$ is H or alkyl, $R^3$ is H, alkyl, alkanoyl, carbamoyl, or lower alkylcarbamoyl, and R is pyridyl, pyrimidinyl, or pyrazinyl, and states that the compounds are useful as bronchodilators.

U.S. Pat. No. 5,137,887 discloses pyrazolotriazines of the formula:

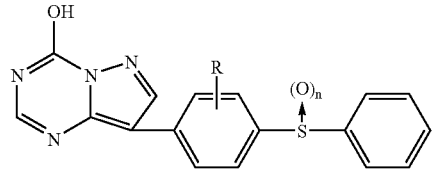

where R is lower alkoxy, and teaches that the compounds are xanthine oxidase inhibitors and are useful for treatment of gout.

U.S. Pat. No. 4,892,576 discloses pyrazolotriazines of the formula:

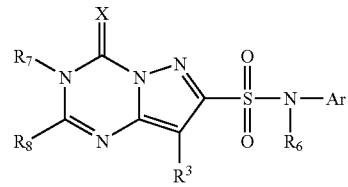

where X is O or S, Ar is a phenyl, naphthyl, pyridyl or thienyl group, $R_6$–$R_8$ are H, alkyl, etc., and $R_9$ is H, alkyl, phenyl, etc. The patent states that the compounds are useful as herbicides and plant growth regulants.

U.S. Pat. No. 5,484,760 and WO 92/10098 discloses herbicidal compositions containing, among other things, a herbicidal compound of the formula:

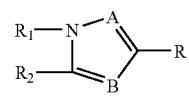

where A can be N, B can be $CR_3$, $R_3$ can be phenyl or substituted phenyl, etc., R is —$N(R_4)SO_2R_5$ or —$SO_2N(R_6)$ $R_7$ and $R_1$ and $R_2$ can be taken together to form

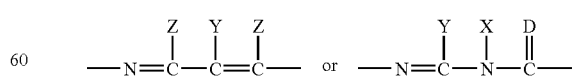

where X, Y and Z are H, alkyl, acyl, etc. and D is O or S.

U.S. Pat. No. 3,910,907 and Senga et al., J. Med. Chem., 1982, 25, 243–249, disclose triazolotriazines cAMP phosphodiesterase inhibitors of the formula:

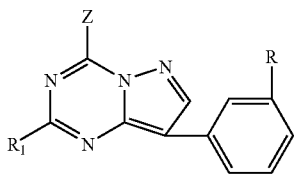

where Z is H, OH, $CH_3$, $C_2H_5$, $C_6H_5$, n-$C_3H_7$, iso-$C_3H_7$, SH, $SCH_3$, NH(n-$C_4H_9$), or N($C_2H_5$)$_2$, R is H or $CH_3$, and $R_1$ is $CH_3$ or $C_2H_5$. The reference lists eight therapeutic areas where inhibitors of cAMP phosphodiesterase could have utility: asthma, diabetes mellitus, female fertility control, male infertility, psoriasis, thrombosis, anxiety, and hypertension.

WO95/35298 (Otsuka, 1995) discloses pyrazolopyrimidines and states that they are useful as analgesics. The compounds are represented by the formula:

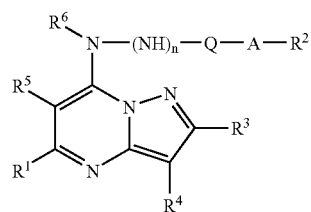

where Q is carbonyl or sulfonyl, n is 0 or 1, A is a single bond, alkylene or alkenylene, $R^1$ is H, alkyl, etc., $R^2$ is naphthyl, cycloalkyl, heteroaryl, substituted phenyl or phenoxy, $R^3$ is H, alkyl or phenyl, $R^4$ is H, alkyl, alkoxycarbonyl, phenylalkyl, optionally phenylthio-substituted phenyl, or halogen, $R^5$ and $R^6$ are H or alkyl.

EP 0 591 528 (Otsuka, 1991) discloses antiinflammatory use of pyrazolopyrimidines represented by the formula:

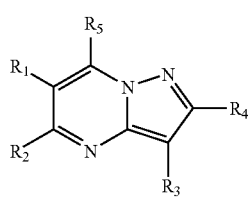

where $R_1$, $R_2$, $R_3$ and $R_4$ are H, carboxyl, alkoxycarbonyl, optionally substituted alkyl, cycloalkyl, or phenyl, $R_5$ is $SR_6$ or $NR_7R_8$, $R_6$ is pyridyl or optionally substituted phenyl, and $R_7$ and $R_8$ are H or optionally substituted phenyl.

Springer et al, J. Med. Chem., 1976, vol. 19, no. 2, 291–296 and Springer U.S. Pat. Nos. 4,021,556 and 3,920,652 disclose pyrazolopyrimidines of the formula:

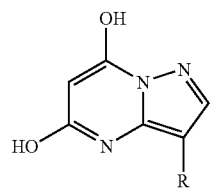

where R can be phenyl, substituted phenyl or pyridyl, and their use to treat gout, based on their ability to inhibit xanthine oxidase.

Joshi et al., J. Prakt. Chemie, 321, 2, 1979, 341–344, discloses compounds of the formula:

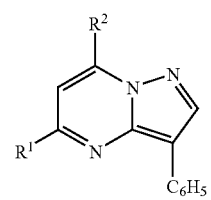

where $R^1$ is $CF_3$, $C_2F_5$, or $C_6H_4F$, and $R^2$ is $CH_3$, $C_2H_5$, $CF_3$, or $C_6H_4F$.

Maquestiau et al., Bull. Soc. Belg., vol. 101, no. 2, 1992, pages 131–136 discloses a pyrazolo[1,5-a]pyrimidine of the formula:

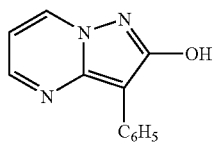

Ibrahim et al., Arch. Pharm. (weinheim) 320, 487–491 (1987) discloses pyrazolo[1,5-a]pyrimidines of the formula:

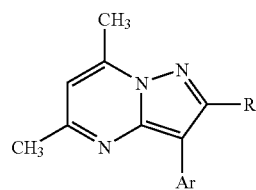

where R is NH2 or OH and Ar is 4-phenyl-3-cyano-2-aminopyrid-2-yl.

Other references which disclose azolopyrimidines inclued EP 0 511 528 (Otsuka, 1992), U.S. Pat. No. 4,997,940 (Dow, 1991), EP 0 374 448 (Nissan, 1990), U.S. Pat. No. 4,621,556 (ICN, 1997), EP 0 531 901 (Fujisawa, 1993), U.S. Pat. No. 4,567,263 (BASF, 1986), EP 0 662 477 (Isagro, 1995), DE 4 243 279 (Bayer, 1994), U.S. Pat. No. 5,397,774 (Upjohn, 1995), EP 0 521 622 (Upjohn, 1993), WO 94/109017 (Upjohn, 1994), J. Med. Chem., 24, 610–613 (1981), and J. Het. Chem., 22, 601 (1985).

SUMMARY OF THE INVENTION

In accordance with one aspect, the present invention provides novel compounds, pharmaceutical compositions and methods which may be used in the treatment of affective disorder, anxiety, depression, irritable bowel syndrome, post-traumatic stress disorder, supranuclear palsy, immune suppression, Alzheimer's disease, gastrointestinal disease, anorexia nervosa or other feeding disorder, drug or alcohol withdrawal symptoms, drug addiction, inflammatory disorder, fertility problems, disorders, the treatment of which can be effected or facilitated by antagonizing CRF, including but not limited to disorders induced or facilitated by CRF, or a disorder selected from inflammatory disorders such as rheumatoid arthritis and osteoarthritis, pain, asthma, psoriasis and allergies; generalized anxiety disorder; panic, phobias, obsessive-compulsive disorder; post-traumatic stress disorder; sleep disorders induced by stress; pain perception such as fibromyalgia; mood disorders such as depression, including major depression, single episode depression, recurrent depression, child abuse induced depression, and postpartum depression; dysthemia; bipolar disorders; cyclothymia; fatigue syndrome; stress-induced headache; cancer, human immunodeficiency virus (HIV) infections; neurodegenerative diseases such as Alzheimer's disease, Parkinson's disease and Huntington's disease; gastrointestinal diseases such as ulcers, irritable bowel syndrome, Crohn's disease, spastic colon, diarrhea, and post operative ilius and colonic hypersensitivity associated by psychopathological disturbances or stress; eating disorders such as anorexia and bulimia nervosa; hemorrhagic stress; stress-induced psychotic episodes; euthyroid sick syndrome; syndrome of inappropriate antidiarrhetic hormone (ADH); obesity; infertility; head traumas; spinal cord trauma; ischemic neuronal damage (e.g., cerebral ischemia such as cerebral hippocampal ischemia); excitotoxic neuronal damage; epilepsy; cardiovascular and hear related disorders including hypertension, tachycardia and congestive heart failure; stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependencies on alcohol, cocaine, heroin, benzodiazepines, or other drugs); drug and alcohol withdrawal symptoms; osteoporosis; psychosocial dwarfism and hypoglycemia in a mammal.

The present invention provides novel compounds which bind to corticotropin releasing factor receptors, thereby altering the anxiogenic effects of CRF secretion. The compounds of the present invention are useful for the treatment of psychiatric disorders and neurological diseases, anxiety-related disorders, post-traumatic stress disorder, supranuclear palsy and feeding disorders as well as treatment of immunological, cardiovascular or heart-related diseases and colonic hypersensitivity associated with psychopathological disturbance and stress in a mammal.

According to another aspect, the present invention provides novel compounds of Formulae (1) and (2) (described below) which are useful as antagonists of the corticotropin releasing factor. The compounds of the present invention exhibit activity as corticotropin releasing factor antagonists and appear to suppress CRF hypersecretion. The present invention also includes pharmaceutical compositions containing such compounds of Formulae (1) and (2), and methods of using such compounds for the suppression of CRF hypersecretion, and/or for the treatment of anxiogenic disorders.

According to yet another aspect of the invention, the compounds provided by this invention (and especially labelled compounds of this invention) are also useful as standards and reagents in determining the ability of a potential pharmaceutical to bind to the CRF receptor.

DETAILED DESCRIPTION OF INVENTION

The present invention comprises a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of Formulae (1) or (2):

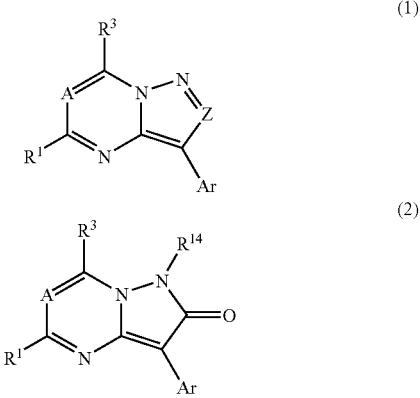

and isomers thereof, stereoisomeric forms thereof, or mixtures of stereoisomeric forms thereof, and pharmaceutically acceptable salt or pro-drug forms thereof, wherein:

A is N or CR;

Z is N or $CR^2$;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached to an unsaturated carbon atom;

R is independently selected at each occurrence from H, $C_1$–$C_4$ alkyl, $C_2$–$C_4$ alkenyl, $C_2$–$C_4$ alkynyl, $C_3$–$C_6$ cycloalkyl, $C_4$–$C_7$ cycloalkylalkyl, halo, CN, $C_1$–$C_4$ haloalkyl;

$R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from H, $C_1$–$C_4$ alkyl, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, halo, CN, —$NR^6R^7$, $NR^9COR^{10}$, —$NR^6S(O)_nR^7$, $S(O)_nNR^6R^7$, $C_1$–$C_4$ haloalkyl, —$OR^7$, SH or —$S(O)_nR^{12}$;

$R^3$ is selected from:
—H, $OR^7$, SH, $S(O)_nR^{13}$, $COR^7$, $CO_2R^7$, $OC(O)R^{13}$, $NR^8COR^7$, $N(COR^7)_2$, $NR^8CONR^6R^7$, $NR^8CO_2R^{13}$, $NR^6R^7$, $NR^{6a}R^{7a}$, $N(OR^7)R^6$, $CONR^6R^7$, aryl, heteroaryl and heterocyclyl, or
—$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from:
$C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, $NO_2$, halo, CN, $C_1$–$C_4$ haloalkyl, $NR^6R^7$, $NR^8COR^7$, $NR^8CO_2R^7$, $COR^7$, $OR^7$, $CONR^6R^7$, $CO(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^8COR^7$, $NR^8CO_2R^7$, $COR^7$ $OR^7$, $CONR^6R^7$, $CO_2R^7$, $CO(NOR^9)R^7$, or $S(O)_nR^7$;

$R^6$ and $R^7$, $R^{6a}$ and $R^{7a}$ are independently selected at each occurrence from:
—H,
—$C_1$–$C_{10}$ alkyl, $C_3$–$C_{10}$ alkenyl, $C_3$–$C_{10}$alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl;

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{14}$ is selected from $C_1$–$C_{10}$ alkyl, $C_3$–$C_{10}$ alkenyl, $C_3$–$C_{10}$ alkynyl, $C_3$–$C_8$ cycloalkyl, or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, $CONR^{16}R^{15}$, and $C_1$–$C_6$ alkylthio, $C_1$–$C_6$ alkylsulfinyl and $C_1$–$C_6$ alkylsulfonyl;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$; heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$;

n is independently at each occurrence 0, 1 or 2.

Preferred methods of the present invention are methods in wherein in the compound of Formulae (1) or (2), Ar is phenyl, pyridyl or 2,3-dihydrobenzofuranyl, each optionally substituted with 1 to 4 $R^4$ substituents.

Further preferred methods of the above invention are methods wherein, in the compound of Formulae (1) or (2), A is N, Z is $CR^2$, Ar is 2,4-dichlorophenyl, 2,4-dimethylphenyl or 2,4,6-trimethylphenyl, $R^1$ and $R^2$ are $CH_3$, and $R^3$ is $NR^{6a}R^{7a}$.

The present invention comprises compounds of Formulae (1) or (2):

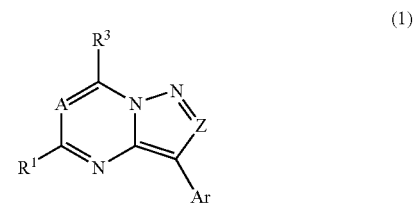

(1)

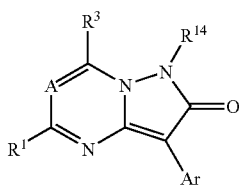

(2)

and isomers thereof, stereoisomeric forms thereof, or mixtures of stereoisomeric forms thereof, and pharmaceutically acceptable salt or pro-drug forms thereof wherein:

A is N or CR;

Z is N or $CR^2$;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached to an unsaturated carbon atom;

R is independently selected at each occurrence from H, $C_1$–$C_4$ alkyl, $C_2$–$C_4$ alkenyl, $C_2$–$C_4$ alkynyl, $C_3$–$C_6$ cycloalkyl, $C_4$–$C_7$ cycloalkylalkyl, halo, CN, $C_1$–$C_4$ haloalkyl;

$R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from H, $C_1$–$C_4$ alkyl, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, halo, CN, $-NR^6R^7$, $NR^9COR^{10}$, $-NR^6S(O)_nR^7$, $S(O)_nNR^6R^7$, $C_1$–$C_4$ haloalkyl, $-OR^7$, SH or $-S(O)_nR^{12}$;

$R^3$ is selected from:
- —H, $OR^7$, SH, $S(O)_nR^{13}$, $COR^7$, $CO_2R^7$, $OC(O)R^{13}$, $NR^8COR^7$, $N(COR^7)_2$, $NR^8CONR^6R^7$, $NR^8CO_2R^{13}$, $NR^6R^7$, $NR^{6a}R^{7a}$, $N(OR^7)R^6$, $CONR^6R^7$, aryl, heteroaryl and heterocyclyl, or
- —$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from: $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, $NO_2$, halo, CN, $C_1$–$C_4$ haloalkyl, $NR^6R^7$, $NR^8COR^7$, $NR^8CO_2R^7$, $COR^7$, $OR^7$, $CONR^6R^7$, $CO(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^8COR^7$, $NR^8CO_2R^7$, $COR^7$ $OR^7$, $CONR^6R^7$, $CO_2R^7$, $CO(NOR^9)R^7$, or $S(O)_nR^7$;

$R^6$ and $R^7$, $R^{6a}$ and $R^{7a}$ are independently selected at each occurrence from:
- —H,
- —$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
- -aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl;

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{14}$ is selected from $C_1$–$C_{10}$ alkyl, $C_3$–$C_{10}$ alkenyl, $C_3$–$C_{10}$ alkynyl, $C_3$–$C_8$ cycloalkyl, or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, $CONR^{16}R^{15}$, and $C_1$–$C_6$ alkylthio, $C_1$–$C_6$ alkylsulfinyl and $C_1$–$C_6$ alkylsulfonyl;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$;

n is independently at each occurrence 0, 1 or 2, with the provisos that:
(1) when A is N, Z is $CR^2$, $R^2$ is H, $R^3$ is —$OR^7$ or —$OCOR^{13}$, and $R^7$ is H, then $R^1$ is not H, OH or SH;
(2) when A is N, Z is $CR^2$, $R^1$ is $CH_3$ or $C_2H_5$, $R^2$ is H, and $R^3$ is OH, H, $CH_3$, $C_2H_5$, $C_6H_5$, n-$C_3H_7$, i-$C_3H_7$, SH, $SCH_3$, $NHC_4H_9$, or $N(C_2H_5)_2$, then Ar is not phenyl or m-$CH_3$-phenyl;
(3) when A is N, Z is $CR^2$, $R^2$ is H, and Ar is pyridyl, pyrimidinyl or pyrazinyl, and $R^3$ is $NR^{6a}R^{7a}$, then $R^{6a}$ and $R^{7a}$ are not H or alkyl;
(4) when A is N, Z is $CR^2$, and $R^2$ is $SO_2NR^6R^7$, then $R^3$ is not OH or SH;
(5) when A is CR and Z is $CR^2$, then $R^2$ is not —$NR^6SO_2R^7$ or —$SO_2NR^6R^7$;
(6) when A is N, Z is $CR^2$ and $R^2$ is —$NR^6SO_2R^7$ or —$SO_2NR^6R^7$, then $R^3$ is not OH or SH;
(7) when A is N, Z is $CR^2$, $R^1$ is methyl or ethyl, $R^2$ is H, and $R^3$ is H, OH, $CH_3$, $C_2H_5$, $C_6H_5$, n-$C_3H_7$, iso-$C_3H_7$, SH, $SCH_3$, NH(n-$C_4H_9$), or $N(C_2H_5)_2$, then Ar is not unsubstituted phenyl or m-methylphenyl;
(8) when A is CR, Z is $CR^2$, $R^2$ is H, phenyl or alkyl, $R^3$ is $NR^8COR^7$ and Ar is phenyl or phenyl substituted with phenylthio, then $R^7$ is not aryl, aryl($C_1$–$C_4$ alkyl), heteroaryl, heteroaryl($C_1$–$C_4$ alkyl), heterocyclyl or heterocyclyl($C_1$–$C_4$ alkyl);
(9) when A is CR, Z is $CR^2$, $R^2$ is H or alkyl, Ar is phenyl, and $R^3$ is $SR^{13}$ or $NR^{6a}R^{7a}$, then $R^{13}$ is not aryl or heteroaryl and $R^{6a}$ and $R^{7a}$ are not H or aryl; or
(10) when A is CH, Z is $CR^2$, $R^1$ is $OR^{11}$, $R^2$ is H, $R^3$ is $OR^7$, and $R^7$ and $R^{11}$ are both H, then Ar is not phenyl, p-Br-phenyl, p-Cl-phenyl, p-$NHCOCH_3$-phenyl, p-$CH_3$-phenyl, pyridyl or naphthyl;
(11) when A is CH, Z is $CR^2$, $R^2$ is H, Ar is unsubstituted phenyl, and $R^3$ is $CH_3$, $C_2H_5$, $CF_3$ or $C_6H_4F$, then $R_1$, is not $CF_3$ or $C_2F_5$;
(12) when A is CR, R is H, Z is $CR^2$, $R^2$ is OH, and $R^1$ and $R^3$ are H, then Ar is not phenyl;
(13) when A is CR, R is H, Z is $CR^2$, $R^2$ is OH or $NH_2$, $R^1$ and $R^3$ are $CH_3$, then Ar is not 4-phenyl-3-cyano-2-aminopyrid-2-yl.

Preferred compounds of the above invention are compounds of Formulae (1) and (2) and isomers thereof, stereoisomeric forms thereof, or mixtures of stereoisomeric forms thereof, and pharmaceutically acceptable salt or pro-drug forms thereof with the additional provisos that: (1) when A is N, $R^1$ is H, $C_1$–$C_4$ alkyl, halo, CN, $C_1$–$C_{12}$ hydroxyalkyl, $C_1$–$C_4$ alkoxyalkyl or $SO_2(C_1$–$C_4$ alkyl), $R^3$ is $NR^{6a}R^{7a}$ and $R^{6a}$ is unsubstituted $C_1$–$C_4$ alkyl, then $R^{7a}$ is not phenyl, naphthyl, thienyl, benzothienyl, pyridyl, quinolyl, pyrazinyl, furanyl, benzofuranyl, benzothiazolyl, indolyl or $C_3$–$C_6$ cycloalkyl; and (2) A is N, $R^1$ is H, $C_1$–$C_4$ alkyl, halo, CN, $C_1$–$C_{12}$ hydroxyalkyl, $C_1$–$C_4$ alkoxyalkyl or $SO_2(C_1$–$C_4$ alkyl), $R^3$ is $NR^{6a}R^{7a}$ and $R^{7a}$ is unsubstituted $C_1$–$C_4$ alkyl, then $R^{6a}$ is not phenyl, naphthyl, thienyl, benzothienyl, pyridyl, quinolyl, pyrazinyl, furanyl, benzofuranyl, benzothiazolyl, indolyl or $C_3$–$C_6$ cycloalkyl.

Preferred compounds of the above invention also include compounds of Formulae (1) and (2) and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl, each optionally substituted with 1 to 4 $R^4$ substituents.

Preferred compounds of the above invention also include compounds of Formulae (1) and (2) and isomers thereof, stereoisomeric forms thereof, or mixtures of stereoisomeric forms thereof, and pharmaceutically acceptable salt or pro-drug forms thereof wherein A is N, Z is $CR^2$, Ar is 2,4-dichlorophenyl, 2,4-dimethylphenyl or 2,4,6-trimethylphenyl, $R^1$ and $R^2$ are $CH_3$, and $R^3$ is $NR^{6a}R^{7a}$.

More preferred compounds of the above invention are compounds and isomers thereof, stereoisomeric forms thereof, or mixtures of stereoisomeric forms thereof, and pharmaceutically acceptable salt or pro-drug forms thereof wherein A is N.

More preferred compounds of the above invention also include compounds and isomers thereof, stereoisomeric forms thereof, or mixtures of stereoisomeric forms thereof, and pharmaceutically acceptable salt or pro-drug forms thereof.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl and each Ar is optionally substituted with 1 to 4 $R^4$ substituents.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl, and each Ar is optionally substituted with 1 to 4 $R^4$ substituents, and $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein Z is $CR^2$.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl and each Ar is optionally substituted with 1 to 4 $R^4$ substituents.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ is independently selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, -aryl, aryl($C_1$–$C_4$ alkyl), heteroaryl, heteroaryl($C_1$–$C_4$ alkyl), heterocyclyl or heterocyclyl($C_1$–$C_4$ alkyl); and
$R^{7a}$ is independently selected at each occurrence from:
—H,
—$C_5$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are identical and are selected from:
—$C_1$–$C_4$ alkyl or $C_3$–$C_6$ cycloalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, —$COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, and -aryl or heteroaryl.

More preferred compounds of the above invention also include compounds and isomers thereof, stereoisomeric forms thereof, or mixtures of stereoisomeric forms thereof, and pharmaceutically acceptable salt or pro-drug forms thereof wherein
$R^{6a}$ is selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);
$R^{7a}$ is selected from:
—$C_1$–$C_4$ alkyl and each such $C_1$–$C_4$ alkyl is substituted with 1–3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein one of $R^{6a}$ and $R^{7a}$ is selected from:
—$C_3$–$C_6$ cycloalkyl, each such $C_3$–$C_6$ cycloalkyl optionally substituted with 1–3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl,
-heteroaryl or
-heterocyclyl, and the other of $R^{6a}$ and $R^{7a}$ is unsubstituted $C_1$–$C_4$ alkyl.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are independently H or $C_1$–$C_{10}$ alkyl, each such $C_1$–$C_{10}$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $R^8CONR^{16}R^{15}$, $NR^8CO_2R^{13}$, $NR^{16}R^{15}$, $CONR^{16}R^{15}$, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl, and each Ar is optionally substituted with 1 to 4 $R^4$ substituents, and $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein
$R^{6a}$ is independently selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);
$R^{7a}$ is independently selected at each occurrence from:
—H,
—$C_5$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are identical and are selected from:
— $C_1$–$C_4$ alkyl or $C_3$–$C_6$ cycloalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, —$COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, and -aryl or heteroaryl.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are identical and are
— $C_1$–$C_4$ alkyl, each such $C_1$–$C_4$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$— $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ is selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);
$R^{7a}$ is:
— $C_1$–$C_4$ alkyl and each such $C_1$–$C_4$ alkyl is substituted with 1–3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein one of $R^{6a}$ and $R^{7a}$ is selected from:
— $C_3$–$C_6$ cycloalkyl, each such $C_3$–$C_6$ cycloalkyl optionally substituted with 1–3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl,
-heteroaryl or
-heterocyclyl, and the other of $R^{6a}$ and $R^{7a}$ is unsubstituted $C_1$–$C_4$ alkyl.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are independently H or $C_1$–$C_{10}$ alkyl, each such $C_1$–$C_{10}$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $R^8CONR^{16}R^{15}$, $NR^8CO_2R^{13}$, $NR^{16}R^{15}$, $CONR^{16}R^{15}$, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein
—Ar is phenyl, pyridyl or 2,3-dihydrobenzofuranyl, and each Ar is optionally substituted with 1 to 4 $R^4$ substituents,
—$R^3$ is $NR^{6a}R^{7a}$ or $OR^7$ and
—$R^1$ and $R^2$ are independently selected from H, $C_1$–$C_4$ alkyl, $C_3$–$C_6$ cycloalkyl, $C_4$–$C_{10}$ cycloalkylalkyl.

More preferred compounds of the above invention also include compounds and isomers thereof, stereoisomeric forms thereof, or mixtures of stereoisomeric forms thereof, and pharmaceutically acceptable salt or pro-drug forms thereof wherein
$R^{6a}$ is independently selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);
$R^{7a}$ is independently selected at each occurrence from:
—H,
—$C_5$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, NR⁶R⁷ and NR⁶ᵃR⁷ᵃ are independently piperidine, pyrrolidine, piperazine, N-methylpiperazine, morpholine or thiomorpholine, each optionally substituted with 1–3 $C_1$–$C_4$ alkyl groups.

More preferred compounds of the above invention also include compounds and isomers thereof, stereoisomeric forms thereof, or mixtures of stereoisomeric forms thereof, and pharmaceutically acceptable salt or pro-drug forms thereof wherein R⁶ᵃ and R⁷ᵃ are identical and are selected from:
- $C_1$–$C_4$ alkyl or $C_3$–$C_6$ cycloalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, OR¹⁵, SH, S(O)ₙR¹³, —COR¹⁵, CO₂R¹⁵, OC(O)R¹³, NR⁸COR¹⁵, N(COR¹⁵)₂, NR⁸CONR¹⁶R¹⁵, NR⁸CO₂R¹³, NR¹⁶R¹⁵, CONR¹⁶R¹⁵, aryl, heteroaryl or heterocyclyl, and -aryl or heteroaryl.

More preferred compounds of the above invention also include compounds and isomers thereof, stereoisomeric forms thereof, or mixtures of stereoisomeric forms thereof, and pharmaceutically acceptable salt or pro-drug forms thereof wherein R⁶ᵃ and R⁷ᵃ are identical and are
- $C_1$–$C_4$ alkyl, each such $C_1$–$C_4$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, OR¹⁵, SH, S(O)ₙR¹³, —COR¹⁵, CO₂R¹⁵, OC(O)R¹³, NR⁸COR¹⁵, N(COR¹⁵)₂, NR⁸CONR¹⁶R¹⁵, NR⁸CO₂R¹³, NR¹⁶R¹⁵, CONR¹⁶R¹⁵, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein R⁶ᵃ is selected from:
- —H,
- —$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, OR¹⁵, SH, S(O)ₙR¹³, COR¹⁵, CO₂R¹⁵, OC(O)R¹³, NR⁸COR¹⁵, N(COR¹⁵)₂, NR⁸CONR¹⁶R¹⁵, NR⁸CO₂R¹³, NR¹⁶R¹⁵, CONR¹⁶R¹⁵, aryl, heteroaryl or heterocyclyl,
- -aryl, aryl($C_1$–$C_4$ alkyl), heteroaryl, heteroaryl($C_1$–$C_4$ alkyl), heterocyclyl or heterocyclyl($C_1$–$C_4$ alkyl);

R⁷ᵃ is:
- —$C_1$–$C_4$ alkyl and each such $C_1$–$C_4$ alkyl is substituted with 1–3 substituents independently selected at each occurrence from $C_1$–$C_6$ alkyl, $C_3$–$C_6$ cycloalkyl, halo, $C_1$–$C_4$ haloalkyl, cyano, OR¹⁵, SH, S(O)ₙR¹³, COR¹⁵, CO₂R¹⁵, OC(O)R¹³, NR⁸COR¹⁵, N(COR¹⁵)₂, NR⁸CONR¹⁶R¹⁵, NR⁸CO₂R¹³, NR¹⁶R¹⁵, CONR¹⁶R¹⁵, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein one of R⁶ᵃ and R⁷ᵃ is selected from:
- —$C_3$–$C_6$ cycloalkyl, each such $C_3$–$C_6$ cycloalkyl optionally substituted with 1–3 substituents independently selected at each occurrence from $C_1$–$C_6$ alkyl, $C_3$–$C_6$ cycloalkyl, halo, $C_1$–$C_4$ haloalkyl, cyano, OR¹⁵, SH, S(O)ₙR¹³, COR¹⁵, CO₂R¹⁵, OC(O)R¹³, NR⁸COR¹⁵, N(COR¹⁵)₂, NR⁸CONR¹⁶R¹⁵, NR⁸CO₂R¹³, NR¹⁶R¹⁵, CONR¹⁶R¹⁵, aryl, heteroaryl or heterocyclyl,
- -aryl,
- -heteroaryl or
- -heterocyclyl, and the other of R⁶ᵃ and R⁷ᵃ is unsubstituted $C_1$–$C_4$ alkyl.

More preferred compounds of the above invention also include compounds and isomers thereof, stereoisomeric forms thereof, or mixtures of stereoisomeric forms thereof, and pharmaceutically acceptable salt or pro-drug forms thereof wherein R⁶ᵃ and R⁷ᵃ are independently H or $C_1$–$C_{10}$ alkyl, each such $C_1$–$C_{10}$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, OR¹⁵, SH, S(O)ₙR¹³, COR¹⁵, CO₂R¹⁵, OC(O)R¹³, NR⁸COR¹⁵, N(COR¹⁵)₂, R⁸CONR¹⁶R¹⁵, NR⁸CO₂R¹³, NR¹⁶R¹⁵, CONR¹⁶R¹⁵, aryl, heteroaryl or heterocyclyl.

Specifically preferred compounds of the above invention are compounds of Formula (50)

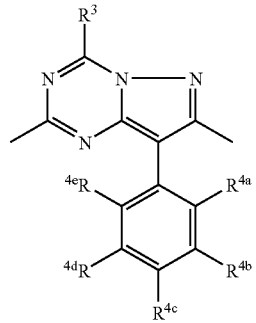

FORMULA (50)

and isomers thereof, stereoisomeric forms thereof, or mixtures of stereoisomeric forms thereof, and pharmaceutically acceptable salt or pro-drug forms thereof, selected from the group consisting of:

a compound of Formula (50) wherein R³ is —NHCH(n-Pr)₂, R⁴ᵃ is Cl, R⁴ᵇ is H, R⁴ᶜ is Cl, R⁴ᵈ is H and R⁴ᵉ is H;

a compound of Formula (50) wherein R³ is —N(Et)(n-Bu), R⁴ᵃ is Cl, R⁴ᵇ is H, R⁴ᶜ is Cl, R⁴ᵈ is H and R⁴ᵉ is H;

a compound of Formula (50) wherein R³ is -(n-Pr)(CH₂cPr), R⁴ᵃ is Cl, R⁴ᵇ is H, R⁴ᶜ is Cl, R⁴ᵈ is H and R⁴ᵉ is H;

a compound of Formula (50) wherein R³ is —N(CH₂CH₂OMe)₂, R⁴ᵃ is Cl, R⁴ᵇ is H, R⁴ᶜ is Cl, R⁴ᵈ is H and R⁴ᵉ is H;

a compound of Formula (50) wherein R³ is —NHCH(Et)(n-Bu), R⁴ᵃ is Cl, R⁴ᵇ is H, R⁴ᶜ is Cl, R⁴ᵈ is H and R⁴ᵉ is H;

a compound of Formula (50) wherein R³ is —NHCH(Et)(CH₂OMe), R⁴ᵃ is Cl, R⁴ᵇ is H, R⁴ᶜ is Cl, R⁴ᵈ is H and R⁴ᵉ is H;

a compound of Formula (50) wherein R³ is —NHCH(CH₂OMe)₂, R⁴ᵃ is Cl, R⁴ᵇ is H, R⁴ᶜ is Cl, R⁴ᵈ is H and R⁴ᵉ is H;

a compound of Formula (50) wherein R³ is —N(Et)₂, R⁴ᵃ is Cl, R⁴ᵇ is H, R⁴ᶜ is Cl, R⁴ᵈ is H and R⁴ᵉ is H;

a compound of Formula (50) wherein R³ is —NHCH(CH₂OEt)₂, R⁴ᵃ is Cl, R⁴ᵇ is H, R⁴ᶜ is Cl, R⁴ᵈ is H and R⁴ᵉ is H;

a compound of Formula (50) wherein R³ is —NHCH(Et)₂, R⁴ᵃ is Cl, R⁴ᵇ is H, R⁴ᶜ is Cl, R⁴ᵈ is H and R⁴ᵉ is H;

a compound of Formula (50) wherein $R^3$ is —N(Me)(Ph), $R^{4a}$ is $C^1$, $R^{4b}$ is H, $R^{4c}$ is $C^1$, $R^{4d}$ is H and $R^{4e}$ is H;

a compound of Formula (50) wherein $R^3$ is —N(n-Pr)$_2$, $R^{4a}$ is $C^1$, $R^{4b}$ is H, $R^{4c}$ is $C^1$, $R^{4d}$ is H and $R^{4e}$ is H;

a compound of Formula (50) wherein $R^3$ is —NHCH(Et)(n-Pr), $R^{4a}$ is $C^1$, $R^{4b}$ is H, $R^{4c}$ is Cl, $R^{4d}$ is H and $R^{4e}$ is H;

a compound of Formula (50) wherein $R^3$ is —NHCH(CH$_2$OMe)$_2$, $R^{4a}$ is Me, $R^{4b}$ is H, $R^{4c}$ is Me, $R^{4d}$ is H and $R^{4e}$ is Me;

a compound of Formula (50) wherein $R^3$ is —NHCH(CH$_2$OMe)$_2$, $R^{4a}$ is Me, $R^{4b}$ is H, $R^{4c}$ is Me, $R^{4d}$ is H and $R^{4e}$ is H;

a compound of Formula (50) wherein $R^3$ is —N(CH$_2$CH$_2$OMe)$_2$, $R^{4a}$ is Me, $R^{4b}$ is H, $R^{4c}$ is Me, $R^{4d}$ is H and $R^{4e}$ is H;

a compound of Formula (50) wherein $R^3$ is —NHCH(Et)(CH$_2$OMe), $R^{4a}$ is Me, $R^{4b}$ is H, $R^{4c}$ is Me, $R^{4d}$ is H and $R^{4e}$ is H;

a compound of Formula (50) wherein $R^3$ is —NHCH(Et)$_2$, $R^{4a}$ is Me, $R^{4b}$ is H, $R^{4c}$ is Me, $R^{4d}$ is H and $R^{4e}$ is H;

a compound of Formula (50) wherein $R^3$ is —OEt, $R^{4a}$ is $C^1$, $R^{4b}$ is H, $R^{4c}$ is Cl, $R^{4d}$ is H and $R^{4e}$ is H;

a compound of Formula (50) wherein $R^3$ is —N(Et)$_2$, $R^{4a}$ is Me, $R^{4b}$ is H, $R^{4c}$ is Me, $R^{4d}$ is H and $R^{4e}$ is H;

a compound of Formula (50) wherein $R^3$ is —N(CH$_2$CN)$_2$, $R^{4a}$ is Me, $R^{4b}$ is H, $R^{4c}$ is Me, $R^{4d}$ is H and $R^{4e}$ is H;

a compound of Formula (50) wherein $R^3$ is —NHCH(Me)(CH$_2$OMe), $R^{4a}$ is Me, $R^{4b}$ is H, $R^{4c}$ is Me, $R^{4d}$ is H and $R^{4e}$ is H;

a compound of Formula (50) wherein $R^3$ is —OCH(Et)(CH$_2$OMe), $R^{4a}$ is Me, $R^{4b}$ is H, $R^{4c}$ is Me, $R^{4d}$ is H and $R^{4e}$ is H;

a compound of Formula (50) wherein $R^3$ is —N(n-Pr)(CH$_2$c-Pr), $R^{4a}$ is Me, $R^{4b}$ is H, $R^{4c}$ is Me, $R^{4d}$ is H and $R^{4e}$ is H;

a compound of Formula (50) wherein $R^3$ is —NHCH(Me)(CH$_2$N(Me)$_2$), $R^{4a}$ is Me, $R^{4b}$ is H, $R^{4c}$ is Me, $R^{4d}$ is H and $R^{4e}$ is H;

a compound of Formula (50) wherein $R^3$ is —N(cPr)(CH$_2$CH$_2$CN), $R^{4a}$ is Me, $R^{4b}$ is H, $R^{4c}$ is Me, $R^{4d}$ is H and $R^{4e}$ is H;

a compound of Formula (50) wherein $R^3$ is —N(n-Pr)(CH$_2$CH$_2$CN), $R^{4a}$ is Me, $R^{4b}$ is H, $R^{4c}$ is Me, $R^{4d}$ is H and $R^{4e}$ is H;

a compound of Formula (50) wherein $R^3$ is —N(n-Bu)(CH$_2$CN), $R^{4a}$ is Me, $R^{4b}$ is H, $R^{4c}$ is Me, $R^{4d}$ is H and $R^{4e}$ is H;

a compound of Formula (50) wherein $R^3$ is NHCH(Et)(CH$_2$OMe), $R^{4a}$ is Me, $R^{4b}$ is H, $R^{4c}$ is Me, $R^{4d}$ is H and $R^{4e}$ is Me;

a compound of Formula (50) wherein $R^3$ is —NHCH(Et)$_2$, $R^{4a}$ is Me, $R^{4b}$ is H, $R^{4c}$ is Me, $R^{4d}$ is H and $R^{4e}$ is Me;

a compound of Formula (50) wherein $R^3$ is —N(CH$_2$CH$_2$OMe)$_2$, $R^{4a}$ is Me, $R^{4b}$ is H, $R^{4c}$ is Me, $R^{4d}$ is H and $R^{4e}$ is Me;

a compound of Formula (50) wherein $R^3$ is —NHCH(CH$_2$OMe)$_2$, $R^{4a}$ is Br, $R^{4b}$ is H, $R^{4c}$ is OMe, $R^{4d}$ is H and $R^{4e}$ is H;

a compound of Formula (50) wherein $R^3$ is —NHCH(Et)(CH$_2$OMe), $R^{4a}$ is Br, $R^{4b}$ is H $R^{4c}$ is OMe, $R^{4d}$ is H and $R^{4e}$ is H;

a compound of Formula (50) wherein $R^3$ is —N(Et)$_2$, $R^{4a}$ is Me, $R^{4b}$ is H, $R^{4c}$ is Me, $R^{4d}$ is H and $R^{4e}$ is Me;

a compound of Formula (50) wherein $R^3$ is —NHCH(CH$_2$OEt)$_2$, $R^{4a}$ is Me, $R^{4b}$ is H, $R^{4c}$ is Me, $R^{4d}$ is H and $R^{4e}$ is Me;

a compound of Formula (50) wherein $R^3$ is —NHCH(CH$_2$CH$_2$OMe)(CH$_2$OMe)$_2$, $R^{4a}$ is Me, $R^{4b}$ is H, $R^{4c}$ is Me, $R^{4d}$ is H and $R^{4e}$ is Me;

a compound of Formula (50) wherein $R^3$ is morpholino, $R^{4a}$ is Me, $R^{4b}$ is H, $R^{4c}$ is Me, $R^{4d}$ is H and $R^{4e}$ is H;

a compound of Formula (50) wherein $R^3$ is —N(CH$_2$CH$_2$OMe)$_2$, $R^{4a}$ is Br, $R^{4b}$ is H, $R^{4c}$ is OMe, $R^{4d}$ is H and $R^{4c}$ is H;

a compound of Formula (50) wherein $R^3$ is —NHCH(Et)$_2$, $R^{4a}$ is Br, $R^{4b}$ is H, $R^{4c}$ is OMe, $R^{4d}$ is H and $R^{4e}$ is H;

a compound of Formula (50) wherein $R^3$ is —N(Et)$_2$, $R^{4a}$ is Br, $R^{4b}$ is H, $R^{4c}$ is OMe, $R^{4d}$ is H and $R^{4e}$ is H;

a compound of Formula (50) wherein $R^3$ is —NH(c-Pr), $R^{4a}$ is Me, $R^{4b}$ is H, $R^{4c}$ is Me, $R^{4d}$ is H and $R^{4e}$ is H;

a compound of Formula (50) wherein $R^3$ is NHCH(CH$_2$OMe)$_2$, $R^{4a}$ is CN, $R^{4b}$ is H, $R^{4c}$ is OMe, $R^{4d}$ is H and $R^{4e}$ is H;

a compound of Formula (50) wherein $R^3$ is —N(c-Pr)(CH$_2$CH$_2$CN), $R^{4a}$ is Me, $R^{4b}$ is H, $R^{4c}$ is Me, $R^{4d}$ is H and $R^{4e}$ is Me;

a compound of Formula (50) wherein $R^3$ is —NCH(CH$_2$OMe)$_2$, $R^{4a}$ is Me, $R^{4b}$ is H, $R^{4c}$ is Br, $R^{4d}$ is H and $R^{4e}$ is H;

a compound of Formula (50) wherein $R^3$ is —NHCH(CH$_2$OMe)(CH$_2$CH$_2$OMe), $R^{4a}$ is Me, $R^{4b}$ is H, $R^{4c}$ is Br, $R^{4d}$ is H and $R^{4e}$ is H;

a compound of Formula (50) wherein $R^3$ is —NHCH(CH$_2$OMe)$_2$, $R^{4a}$ is Me, $R^{4b}$ is H, $R^{4c}$ is OMe, $R^{4d}$ is Me and $R^{4e}$ is H;

a compound of Formula (50) wherein $R^3$ is —N(CH$_2$CH$_2$OMe)$_2$, $R^{4a}$ is Me, $R^{4b}$ is H, $R^{4c}$ is OMe, $R^{4d}$ is Me and $R^{4e}$ is H;

a compound of Formula (50) wherein $R^3$ is —NHCH(Et)$_2$, $R^{4a}$ is Me, $R^{4b}$ is H, $R^{4c}$ is OMe, $R^{4d}$ is Me and $R^{4e}$ is H;

a compound of Formula (50) wherein a compound of Formula (50) wherein $R^3$ is —N(Et)$_2$, $R^{4a}$ is Me, $R^{4b}$ is H, $R^{4c}$ is OMe, $R^{4d}$ is Me and $R^{4e}$ is H;

a compound of Formula (50) wherein $R^3$ is —NHCH(CH$_2$OMe)$_2$, $R^{4a}$ is Cl, $R^{4b}$ is H, $R^{4c}$ is Me, $R^{4d}$ is H and $R^{4e}$ is H;

a compound of Formula (50) wherein $R^3$ is —NHCH(Et)(CH$_2$OMe), $R^{4a}$ is $C^1$, $R^{4b}$ is H, $R^{4c}$ is Me, $R^{4d}$ is H and $R^{4e}$ is H;

a compound of Formula (50) wherein $R^3$ is —N(CH$_2$CH$_2$OMe)$_2$, $R^{4a}$ is $C^1$, $R^{4b}$ is H, $R^{4c}$ is Me, $R^{4d}$ is H and $R^{4e}$ is H;

a compound of Formula (50) wherein $R^3$ is —NHCH(CH$_2$OMe)(CH$_2$CH$_2$OMe), $R^{4a}$ is $C^1$, $R^{4b}$ is H, $R^{4c}$ is Me, $R^{4d}$ is H and $R^{4e}$ is H;

a compound of Formula (50) wherein $R^3$ is —N(c-Pr)(CH$_2$CH$_2$CN), $R^{4a}$ is Me, $R^{4b}$ is H, $R^{4c}$ is OMe, $R^{4d}$ is Me and $R^{4e}$ is H;

a compound of Formula (50) wherein $R^3$ is —N(cPr)(CH$_2$CH$_2$CN), $R^{4a}$ is $C^1$, $R^{4b}$ is H, $R^{4c}$ is $C^1$, $R^{4d}$ is H and $R^{4e}$ is H;

a compound of Formula (50) wherein $R^3$ is (S)—NHCH(CH$_2$OMe)(CH$_2$CH$_2$OMe), $R^{4a}$ is Cl, $R^{4b}$ is H, $R^{4c}$ is $C^1$, $R^{4d}$ is H and $R^{4e}$ is H;

a compound of Formula (50) wherein $R^3$ is —NHCH(CH$_2$OMe)(CH$_2$CH$_2$OMe), $R^{4a}$ is Cl, $R^{4b}$ is H, $R^{4c}$ is Cl, $R^{4d}$ is H and $R^{4e}$ is H;

a compound of Formula (50) wherein $R^3$ is —NHCH(Et)$_2$, $R^{4a}$ is Me, $R^{4b}$ is H, $R^{4c}$ is Br, $R^{4d}$ is H and $R^{4e}$ is H;

a compound of Formula (50) wherein $R^3$ is —N(CH$_2$CH$_2$OMe)$_2$, $R^{4a}$ is Me, $R^{4b}$ is H, $R^{4c}$ is Br, $R^{4d}$ is H and $R^{4e}$ is H;

a compound of Formula (50) wherein $R^3$ is —NH(CH$_2$OMe)(CH$_2$-iPr), $R^{4a}$ is Me, $R^{4b}$ is H, $R^{4c}$ is Me, $R^{4d}$ is H and $R^{4e}$ is H;

a compound of Formula (50) wherein $R^3$ is —N(CH$_2$CH$_2$OMe)$_2$, $R^{4a}$ is Me, $R^{4b}$ is H, $R^{4c}$ is H, $R^{4d}$ is H and $R^{4e}$ is H;

a compound of Formula (50) wherein $R^3$ is —N(CH$_2$CH$_2$OMe)$_2$, $R^{4a}$ is Me, $R^{4b}$ is H, $R^{4c}$ is NMe$_2$, $R^{4d}$ is H and $R^{4e}$ is H;

a compound of Formula (50) wherein $R^3$ is —NHCH(CH$_2$OMe)(n-Pr), $R^{4a}$ is Me, $R^{4b}$ is H, $R^{4c}$ is Me, $R^{4d}$ is H and $R^{4e}$ is H;

a compound of Formula (50) wherein $R^3$ is —NHCH(CH$_2$OEt)(Et), $R^{4a}$ is Me, $R^{4b}$ is H, $R^{4c}$ is Me, $R^{4d}$ is H and $R^{4e}$ is H;

a compound of Formula (50) wherein $R^3$ is —NHCH(CH$_2$OMe)(CH$_2$CH$_2$OMe), $R^{4a}$ is Me, $R^{4b}$ is H, $R^{4c}$ is NMe2, $R^{4d}$ is H and $R^{4e}$ is H;

a compound of Formula (50) wherein $R^3$ is —N(Et)$_2$, $R^{4a}$ is Me, $R^{4b}$ is H, $R^{4c}$ is Cl, $R^{4d}$ is H and $R^{4e}$ is H;

a compound of Formula (50) wherein $R^3$ is —NHCH(Et)$_2$, $R^{4a}$ is Me, $R^{4b}$ is H, $R^{4c}$ is Cl, $R^{4d}$ is H and $R^{4e}$ is H;

a compound of Formula (50) wherein $R^3$ is —N(CH$_2$CH$_2$OMe)$_2$, $R^{4a}$ is Me, $R^{4b}$ is H, $R^{4c}$ is C$^1$, $R^{4d}$ is H and $R^{4e}$ is H;

a compound of Formula (50) wherein $R^3$ is —NHCH(CH$_2$OMe)$_2$, $R^{4a}$ is Me, $R^{4b}$ is H, $R^{4c}$ is C$^1$, $R^{4d}$ is H and $R^{4e}$ is H;

a compound of Formula (50) wherein $R^3$ is —N(Et)$_2$, $R^{4a}$ is Me, $R^{4b}$ is H, $R^{4c}$ is Br, $R^{4d}$ is H and $R^{4e}$ is H;

a compound of Formula (50) wherein $R^3$ is —N(Et)$_2$, $R^{4a}$ is Cl, $R^{4b}$ is H, $R^{4c}$ is Me, $R^{4d}$ is H and $R^{4e}$ is H;

a compound of Formula (50) wherein $R^3$ is —NHCH(Et)$_2$, $R^{4a}$ is C$^1$, $R^{4b}$ is H, $R^{4c}$ is Me, $R^{4d}$ is H and $R^{4e}$ is H;

a compound of Formula (50) wherein $R^3$ is —NHCH(Et)$_2$, $R^{4a}$ is Me, $R^{4b}$ is H, $R^{4c}$ is NMe2, $R^{4d}$ is H and $R^{4e}$ is H;

a compound of Formula (50) wherein $R^3$ is (S)—NHCH(CH$_2$OMe)(CH$_2$CH$_2$OMe), $R^{4a}$ is Me, $R^{4b}$ is H, $R^{4c}$ is Me, $R^{4d}$ is H and $R^{4e}$ is H;

a compound of Formula (50) wherein $R^3$ is —NHCH(CH$_2$OMe)(CH$_2$CH$_2$OMe), $R^{4a}$ is Me, $R^{4b}$ is H, $R^{4c}$ is Me, $R^{4d}$ is H and $R^{4e}$ is H;

a compound of Formula (50) wherein $R^3$ is (S)—NHCH(CH$_2$OMe)(CH$_2$CH$_2$OMe), $R^{4a}$ is Me, $R^{4b}$ is H, $R^{4c}$ is Cl, $R^{4d}$ is H and $R^{4e}$ is H;

a compound of Formula (50) wherein $R^3$ is —NHCH(CH$_2$OMe)(CH$_2$CH$_2$OMe), $R^{4a}$ is Me, $R^{4b}$ is H, $R^{4c}$ is Cl, $R^{4d}$ is H and $R^{4e}$ is H;

a compound of Formula (50) wherein $R^3$ is —N(c-Pr)(CH$_2$CH$_2$CN), $R^{4a}$ is Me, $R^{4b}$ is H, $R^{4c}$ is C$^1$, $R^{4d}$ is H and $R^{4e}$ is H;

a compound of Formula (50) wherein $R^3$ is —NH(Et)(CH$_2$CN), $R^{4a}$ is Me, $R^{4b}$ is H, $R^{4c}$ is C$^1$, $R^{4d}$ is H and $R^{4e}$ is H;

a compound of Formula (50) wherein $R^3$ is —N(Et)$_2$, $R^{4a}$ is Me, $R^{4b}$ is Me, $R^{4c}$ is OMe, $R^{4d}$ is H and $R^{4e}$ is H;

a compound of Formula (50) wherein $R^3$ is —N(CH$_2$CH$_2$OMe)(CH$_2$CH$_2$OH), $R^{4a}$ is Cl, $R^{4b}$ is H, $R^{4c}$ is C$^1$, $R^{4d}$ is H and $R^{4e}$ is H;

a compound of Formula (50) wherein $R^3$ is —N(CH$_2$CH$_2$OMe)$_2$, $R^{4a}$ is Me, $R^{4b}$ is Me, $R^{4c}$ is OMe, $R^{4d}$ is H and $R^{4e}$ is H;

a compound of Formula (50) wherein $R^3$ is —NHCH(Et)$_2$, $R^{4a}$ is Me, $R^{4b}$ is Me, $R^{4c}$ is OMe, $R^{4d}$ is H and $R^{4e}$ is H;

a compound of Formula (50) wherein $R^3$ is —N(CH$_2$c-Pr)(n-Pr), $R^{4a}$ is Me, $R^{4b}$ is H, $R^{4c}$ is C$^1$, $R^{4d}$ is H and $R^{4e}$ is H;

a compound of Formula (50) wherein $R^3$ is —N(c-Pr)(CH$_2$CH$_2$CN), $R^{4a}$ is Me, $R^{4b}$ is Me, $R^{4c}$ is OMe, $R^{4d}$ is H and $R^{4e}$ is H;

a compound of Formula (50) wherein $R^3$ is —NHCH(Et)$_2$, $R^{4a}$ is C$^1$, $R^{4b}$ is H, $R^{4c}$ is OMe, $R^{4d}$ is H and $R^{4e}$ is H;

a compound of Formula (50) wherein $R^3$ is —N(Et)$_2$, $R^{4a}$ is Cl, $R^{4b}$ is H, $R^{4c}$ is OMe, $R^{4d}$ is H and $R^{4e}$ is H;

a compound of Formula (50) wherein $R^3$ is —N(CH$_2$CH$_2$OMe)$_2$, $R^{4a}$ is C$^1$, $R^{4b}$ is H, $R^{4c}$ is OMe, $R^{4d}$ is H and $R^{4e}$ is H;

a compound of Formula (50) wherein $R^3$ is —NHCH(Et)(CH$_2$OMe), $R^{4a}$ is C$^1$, $R^{4b}$ is H, $R^{4c}$ is OMe, $R^{4d}$ is H and $R^{4e}$ is H;

a compound of Formula (50) wherein $R^3$ is —N(Et)$_2$, $R^{4a}$ is Cl, $R^{4b}$ is H, $R^{4c}$ is CN, $R^{4d}$ is H and $R^{4e}$ is H;

a compound of Formula (50) wherein $R^3$ is —N(c-Pr)(CH$_2$CH$_2$CN), $R^{4a}$ is C$^1$, $R^{4b}$ is H, $R^{4c}$ is OMe, $R^{4d}$ is H and $R^{4e}$ is H;

a compound of Formula (50) wherein $R^3$ is —NHCH(CH$_2$OH)$_2$, $R^{4a}$ is C$^1$, $R^{4b}$ is H, $R^{4c}$ is C$^1$, $R^{4d}$ is H and $R^{4e}$ is H; and a compound of Formula (50) wherein $R^3$ is N(CH$_2$CH$_2$OMe)$_2$, $R^{4a}$ is Me, $R^{4b}$ is H, $R^{4c}$ is OMe, $R^{4d}$ is H and $R^{4e}$ is H.

More specifically preferred is 4-(bis-(2-methoxyethyl)amino)-2,7-dimethyl-8-(2-methyl-4-methoxyphenyl)-[1,5-a]-pyrazolo-1,3,5-triazine and isomers thereof, stereoisomeric forms thereof, or mixtures of stereoisomeric forms thereof, and pharmaceutically acceptable salt or pro-drug forms thereof.

More specifically preferred is 4(bis-(2-methoxyethyl)amino)-2,7-dimethyl-8-(2,5-dimethyl-4-methoxyphenyl)-[1,5-a]-pyrazolo-1,3,5-triazine and isomers thereof, stereoisomeric forms thereof, or mixtures of stereoisomeric forms thereof, and pharmaceutically acceptable salt or pro-drug forms thereof.

More preferred are compounds of the above invention are compounds and isomers thereof, stereoisomeric forms thereof, or mixtures of stereoisomeric forms thereof, and pharmaceutically acceptable salt or pro-drug forms thereof wherein A is CR.

More preferred compounds of the above invention also include compounds and isomers thereof, stereoisomeric forms thereof, or mixtures of stereoisomeric forms thereof, and pharmaceutically acceptable salt or pro-drug forms thereof.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl and each Ar is optionally substituted with 1 to 4 $R^4$ substituents.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl, and each Ar is optionally substituted with 1 to 4 $R^4$ substituents, and $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein Z is $CR^2$.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl and each Ar is optionally substituted with 1 to 4 $R^4$ substituents.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein Ar is phenyl, pyridyl or 2,3-dihydrobenzofuranyl, and each Ar is optionally substituted with 1 to 4 $R^4$ substituents, and $R^3$ is $NR^{6a}R^{7a}$ or $OR^7$.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are independently H or $C_1$–$C_{10}$ alkyl, and each such $C_1$–$C_{10}$ alkyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $R^8CONR^{16}R^{15}$, $NR^8CO_2R^{13}$, $NR^{16}R^{15}$, $CONR^{16}R^{15}$, aryl, heteroaryl or heterocyclyl.

More preferred compounds of the above invention also include compounds and isomers thereof, stereoisomeric forms thereof, or mixtures of stereoisomeric forms thereof, and pharmaceutically acceptable salt or pro-drug forms thereof wherein —Ar is phenyl, pyridyl or 2,3-dihydrobenzofuranyl, and each Ar is optionally substituted with 1 to 4 $R^4$ substituents, —$R^3$ is $NR^{6a}R^{7a}$ or $OR^7$ and —$R^1$ and $R^2$ are independently selected from H, $C_1$–$C_4$ alkyl, $C_3$–$C_6$ cycloalkyl, $C_4$–$C_{10}$ cycloalkylalkyl.

More preferred compounds of the above invention also include compounds and isomers thereof, stereoisomeric forms thereof, or mixtures of stereoisomeric forms thereof, and pharmaceutically acceptable salt or pro-drug forms thereof wherein $R^{6a}$ and $R^{7a}$ are independently H or $C_1$–$C_{10}$ alkyl, and each such $C_1$–$C_{10}$ alkyl is optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $R^8CONR^{16}R^{15}$, $NR^8CO_2R^{13}$, $NR^{16}R^{15}$, $CONR^{16}R^{15}$, aryl, heteroaryl or heterocyclyl.

Specifically preferred compounds of the above invention are compounds of Formula (51)

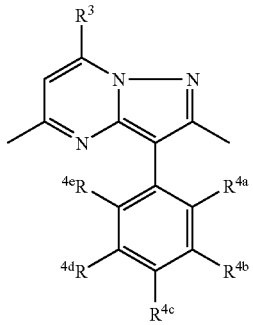

FORMULA (51)

and isomers thereof, stereoisomeric forms thereof, or mixtures of stereoisomeric forms thereof, and pharmaceutically acceptable salt or pro-drug forms thereof selected from the group consisting of:

a compound of Formula (51) wherein $R^3$ is —$NHCH(n-Pr)_2$, $R^{4a}$ is Me, $R^{4b}$ is H, $R^{4c}$ is Me, $R^{4d}$ is H and $R^{4e}$ is H;

a compound of Formula (51) wherein $R^3$ is —NHCH$(CH_2OMe)_2$, $R^{4a}$ is Me, $R^{4b}$ is H, $R^{4c}$ is Me, $R^{4d}$ is H and $R^{4e}$ is H;

a compound of Formula (51) wherein $R^3$ is $N(CH_2CH_2OMe)_2$, $R^{4a}$ is Me, $R^{4b}$ is H, $R^{4c}$ is Me, $R^{4d}$ is H and $R^{4e}$ is H;

a compound of Formula (51) wherein $R^3$ is —$N(c-Pr)(CH_2CH_2CN)$, $R^{4a}$ is Me, $R^{4b}$ is H, $R^{4c}$ is Me, $R^{4d}$ is H and $R^{4e}$ is H;

a compound of Formula (51) wherein $R^3$ is —$N(CH_2CH_2OMe)_2$, $R^{4a}$ is $C^1$, $R^{4b}$ is H, $R^{4c}$ is Me, $R^{4d}$ is H and $R^{4e}$ is H;

a compound of Formula (51) wherein $R^3$ is —NHCH$(CH_2OMe)_2$, $R^{4a}$ is Cl, $R^{4b}$ is H, $R^{4c}$ is Me, $R^{4d}$ is H and $R^{4e}$ is H;

a compound of Formula (51) wherein $R^3$ is —$NHCH(Et)_2$, $R^{4a}$ is Cl, $R^{4b}$ is H, $R^{4c}$ is Me, $R^{4d}$ is H and $R^{4e}$ is H;

a compound of Formula (51) wherein $R^3$ is —$N(Et)_2$, $R^{4a}$ is Me, $R^{4b}$ is H, $R^{4c}$ is Me, $R^{4d}$ is H and $R^{4e}$ is H;

a compound of Formula (51) wherein $R^3$ is —$N(n-Pr)(CH_2CH_2CN)$, $R^{4a}$ is Me, $R^{4b}$ is H, $R^{4c}$ is Me, $R^{4d}$ is H and $R^{4e}$ is H;

a compound of Formula (51) wherein $R^3$ is —$N(n-Bu)(CH_2CH_2CN)$, $R^{4a}$ is Me, $R^{4b}$ is H, $R^{4c}$ is Me, $R^{4d}$ is H and $R^{4e}$ is H;

a compound of Formula (51) wherein $R^3$ is —NHCH(n-Pr)$(CH_2OMe)$, $R^{4a}$ is Me, $R^{4b}$ is H, $R^{4c}$ is Me, $R^{4d}$ is H and $R^{4e}$ is H;

a compound of Formula (51) wherein $R^3$ is —$NHCH(Et)_2$, $R^{4a}$ is Me, $R^{4b}$ is H, $R^{4c}$ is OMe, $R^{4d}$ is H and $R^{4e}$ is H;

a compound of Formula (51) wherein $R^3$ is —NHCH$(CH_2OMe)_2$, $R^{4a}$ is Me, $R^{4b}$ is H, $R^{4c}$ is OMe, $R^{4d}$ is H and $R^{4e}$ is H;

a compound of Formula (51) wherein $R^3$ is (S)—NH$(CH_2CH_2OMe)CH_2OMe$, $R^{4a}$ is Me, $R^{4b}$ is H, $R^{4c}$ is Me, $R^{4d}$ is H and $R^{4e}$ is H;

a compound of Formula (51) wherein $R^3$ is —NH$(CH_2CH_2OMe)CH_2OMe$, $R^{4a}$ is Me, $R^{4b}$ is H, $R^{4c}$ is Me, $R^{4d}$ is H and $R^{4e}$ is H;

a compound of Formula (51) wherein $R^3$ is —$N(CH_2CH_2OMe)_2$, $R^{4a}$ is Me, $R^{4b}$ is H, $R^{4c}$ is Cl, $R^{4d}$ is H and $R^{4e}$ is H;

a compound of Formula (51) wherein $R^3$ is —NH(Et), $R^{4a}$ is Me, $R^{4b}$ is H, $R^{4c}$ is Me, $R^{4d}$ is H and $R^{4e}$ is H;

a compound of Formula (51) wherein $R^3$ is —NHCH(n-Pr)$_2$, $R^{4a}$ is Me, $R^{4b}$ is H, $R^{4c}$ is C$^1$, $R^{4d}$ is H and $R^{4e}$ is H;

a compound of Formula (51) wherein $R^3$ is —NHCH(CH$_2$OMe)$_2$, $R^{4a}$ is Me, $R^{4b}$ is H, $R^{4c}$ is C$^1$, $R^{4d}$ is H and $R^{4e}$ is H;

a compound of Formula (51) wherein $R^3$ is (S)—NH(CH$_2$CH$_2$OMe)CH$_2$OMe, $R^{4a}$ is Me, $R^{4b}$ is H, $R^{4c}$ is Cl, $R^{4d}$ is H and $R^{4e}$ is H;

a compound of Formula (51) wherein $R^3$ is —NH(CH$_2$CH$_2$OMe)CH$_2$OMe, $R^{4a}$ is Me, $R^{4b}$ is H, $R^{4c}$ is Cl, $R^{4d}$ is H and $R^{4e}$ is H;

a compound of Formula (51) wherein $R^3$ is —N(n-Pr)(CH$_2$CH$_2$CN), $R^{4a}$ is Me, $R^{4b}$ is H, $R^{4c}$ is OMe, $R^{4d}$ is H and $R^{4e}$ is H;

a compound of Formula (51) wherein $R^3$ is —N(Et)$_2$, $R^{4a}$ is Me, $R^{4b}$ is H, $R^{4c}$ is OMe, $R^{4d}$ is H and $R^{4e}$ is H;

a compound of Formula (51) wherein $R^3$ is (S)—NH(CH$_2$CH$_2$OMe)CH$_2$OMe, $R^{4a}$ is Cl, $R^{4b}$ is H, $R^{4c}$ is Me, $R^{4d}$ is H and $R^{4e}$ is H;

a compound of Formula (51) wherein $R^3$ is —NH(CH$_2$CH$_2$OMe)CH$_2$OMe, $R^{4a}$ is C$^1$, $R^{4b}$ is H, $R^{4c}$ is Me, $R^{4d}$ is H and $R^{4e}$ is H;

a compound of Formula (51) wherein $R^3$ is —N(Et)$_2$, $R^{4a}$ is Cl, $R^{4b}$ is H, $R^{4c}$ is Me, $R^{4d}$ is H and $R^{4e}$ is H;

a compound of Formula (51) wherein $R^3$ is —N(c-Pr)(CH$_2$CH$_2$CN), $R^{4a}$ is Me, $R^{4b}$ is H, $R^{4c}$ is OMe, $R^{4d}$ is H and $R^{4e}$ is H;

a compound of Formula (51) wherein $R^3$ is —N(c-Pr)(CH$_2$CH$_2$CN), $R^{4a}$ is C$^1$, $R^{4b}$ is H, $R^{4c}$ is Me, $R^{4d}$ is H and $R^{4e}$ is H;

a compound of Formula (51) wherein $R^3$ is —NHCH (n-Pr)(CH$_2$OMe), $R^{4a}$ is Me, $R^{4b}$ is H, $R^{4c}$ is OMe, $R^{4d}$ is H and $R^{4e}$ is H;

a compound of Formula (51) wherein $R^3$ is —NHCH (n-Pr)(CH$_2$OMe), $R^{4a}$ is C$^1$, $R^{4b}$ is H, $R^{4c}$ is Me, $R^{4d}$ is H and $R^{4e}$ is H;

a compound of Formula (51) wherein $R^3$ is —NHCH(Et)$_2$, $R^{4a}$ is Br, $R^{4b}$ is H, $R^{4c}$ is OMe, $R^{4d}$ is OMe and $R^{4e}$ is H;

a compound of Formula (51) wherein $R^3$ is —NHCH(Et)$_2$, $R^{4a}$ is Br, $R^{4b}$ is H, $R^{4c}$ is OMe, $R^{4d}$ is H and $R^{4e}$ is H;

a compound of Formula (51) wherein $R^3$ is —N(CH$_2$CH$_2$OMe)$_2$, $R^{4a}$ is Br, $R^{4b}$ is H, $R^{4c}$ is OMe, $R^{4d}$ is H and $R^{4e}$ is H;

a compound of Formula (51) wherein $R^3$ is —NHCH(CH$_2$OMe)$_2$, $R^{4a}$ is Br, $R^{4b}$ is H, $R^{4c}$ is OMe, $R^{4d}$ is H and $R^{4e}$ is H;

a compound of Formula (51) wherein $R^3$ is —N(Et)$_2$, $R^{4a}$ is Me, $R^{4b}$ is H, $R^{4c}$ is Cl, $R^{4d}$ is H and $R^{4e}$ is H;

a compound of Formula (51) wherein $R^3$ is —N(Et)$_2$, $R^{4a}$ is Cl, $R^{4b}$ is H, $R^{4c}$ is OMe, $R^{4d}$ is OMe and $R^{4e}$ is H;

a compound of Formula (51) wherein $R^3$ is —NHCH(Et)$_2$, $R^{4a}$ is Cl, $R^{4b}$ is H, $R^{4c}$ is OMe, $R^{4d}$ is OMe and $R^{4e}$ is H;

a compound of Formula (51) wherein $R^3$ is —N(CH$_2$CH$_2$OMe)$_2$, $R^{4a}$ is C$^1$, $R^{4b}$ is H, $R^{4c}$ is C$^1$, $R^{4d}$ is H and $R^{4e}$ is H;

a compound of Formula (51) wherein $R^3$ is —NHCH(CH$_2$OMe)$_2$, $R^{4a}$ is C$^1$, $R^{4b}$ is H, $R^{4c}$ is Cl, $R^{4d}$ is H and $R^{4e}$ is H;

a compound of Formula (51) wherein $R^3$ is —N(Pr)(CH$_2$CH$_2$CN), $R^{4a}$ is C$^1$, $R^{4b}$ is H, $R^{4c}$ is Cl, $R^{4d}$ is H and $R^{4e}$ is H;

a compound of Formula (51) wherein $R^3$ is —N(Bu)(Et), $R^{4a}$ is C$^1$, $R^{4b}$ is H, $R^{4c}$ is C$^1$, $R^{4d}$ is H and $R^{4e}$ is H;

a compound of Formula (51) wherein $R^3$ is —NHCH(Et)CH$_2$OMe, $R^{4a}$ is C$^1$, $R^{4b}$ is H, $R^{4c}$ is Cl, $R^{4d}$ is H and $R^{4e}$ is H;

a compound of Formula (51) wherein $R^3$ is —NHCH(Et)$_2$, $R^{4a}$ is C$^1$, $R^{4b}$ is H, $R^{4c}$ is C$^1$, $R^{4d}$ is H and $R^{4e}$ is H;

a compound of Formula (51) wherein $R^3$ is —NHCH(Et)$_2$, $R^{4a}$ is Me, $R^{4b}$ is H, $R^{4c}$ is Me, $R^{4d}$ is H and $R^{4e}$ is H;

a compound of Formula (51) wherein $R^3$ is —NHCH(Et)$_2$, $R^{4a}$ is C$^1$, $R^{4b}$ is H, $R^{4c}$ is Me, $R^{4d}$ is H and $R^{4e}$ is H;

a compound of Formula (51) wherein $R^3$ is —NHCH(Et)$_2$, $R^{4a}$ is Me, $R^{4b}$ is H, $R^{4c}$ is C$^1$, $R^{4d}$ is H and $R^{4e}$ is H;

a compound of Formula (51) wherein $R^3$ is —NEt$_2$, $R^{4a}$ is Me, $R^{4b}$ is H, $R^{4c}$ is OMe, $R^{4d}$ is H and $R^{4e}$ is H; and a compound of Formula (51) wherein $R^3$ is —N(Pr)(CH$_2$CH$_2$CN), $R^{4a}$ is Me, $R^{4b}$ is H, $R^{4c}$ is OMe, $R^{4d}$ is H and $R^{4e}$ is H.

More specifically preferred is 7-(3-pentylamino)-2,5-dimethyl-3-(2-methyl-4-methoxyphenyl)-[1,5-a]-pyrazolopyrimidine and isomers thereof, stereoisomeric forms thereof, or mixtures of stereoisomeric forms thereof, and pharmaceutically acceptable salt or pro-drug forms thereof.

More specifically preferred is 7-(Diethylamino)-2,5-dimethyl-3-(2-methyl-4-methoxyphenyl-[1,5-a]-pyrazolopyrimidine and isomers thereof, stereoisomeric forms thereof, or mixtures of stereoisomeric forms thereof, and pharmaceutically acceptable salt or pro-drug forms thereof.

More specifically preferred is 7-(N-(3-cyanopropyl)-N-propylamino)-2,5-dimethyl-3-(2,4-dimethylphenyl)-[1,5-a]-pyrazolopyrimidine and isomers thereof, stereoisomeric forms thereof, or mixtures of stereoisomeric forms thereof, and pharmaceutically acceptable salt or pro-drug forms thereof.

The present invention also provides pharmaceutical compositions comprising compounds of Formulae (1) and (2) and a pharmaceutically acceptable carrier.

The present invention still further comprises a method of treating affective disorder, anxiety, depression, headache, irritable bowel syndrome, post-traumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of Formulae (1) or (2):

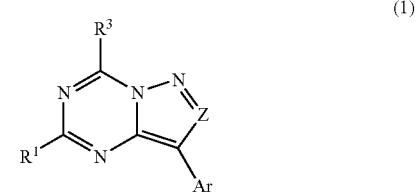

-continued

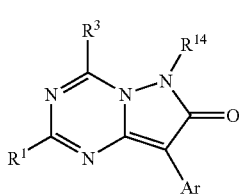

(2)

and isomers thereof, stereoisomeric forms thereof, or mixtures of stereoisomeric forms thereof, and pharmaceutically acceptable salt forms thereof, wherein:

Z is N or $CR^2$;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached to an unsaturated carbon atom;

$R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from H, $C_1$–$C_4$ alkyl, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, halo, CN, —$NR^6R^7$, $NR^9COR^{10}$, —$NR^6S(O)_nR^7$, $S(O)_nNR^6R^7$, $C_1$–$C_4$ haloalkyl, —$OR^7$, SH or —$S(O)_nR^{12}$;

$R^3$ is selected from:
—H, $OR^7$, SH, $S(O)_nR^{13}$, $COR^7$, $CO_2R^7$, $OC(O)R^{13}$, $NR^8COR^7$, $N(COR^7)_2$, $NR^8CONR^6R^7$, $NR^8CO_2R^{13}$, $NR^6R^7$, $NR^{6a}R^{7a}$, $N(OR^7)R^6$, $CONR^6R^7$, aryl, heteroaryl and heterocyclyl, or —$C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from:
$C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, $NO_2$, halo, CN, $C_1$–$C_4$ haloalkyl, $NR^6R^7$, $NR^8COR^7$, $NR^8CO_2R^7$, $COR^7$, $OR^7$, $CONR^6R^7$, $C(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^8COR^7$, $NR^8CO_2R^7$, $COR^7$ $OR^7$, $CONR^6R^7$, $CO_2R^7$, $CO(NOR^9)R^7$, or $S(O)_nR^7$;

$R^6$, $R^7$, $R^{6a}$ and $R^{7a}$ are independently selected at each occurrence from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, -aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl;

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{14}$ is selected from $C_1$–$C_{10}$ alkyl, $C_3$–$C_{10}$ alkenyl, $C_3$–$C_{10}$ alkynyl, $C_3$–$C_8$ cycloalkyl, or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, $CONR^{16}R^{15}$, and $C_1$–$C_6$ alkylthio, $C_1$–$C_6$ alkylsulfinyl and $C_1$–$C_6$ alkylsulfonyl;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$ $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$ $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$;

n is independently at each occurrence 0, 1 or 2;

with the proviso that when Z is $CR^2$, then $R^3$ is not $NR^6R^7$, $NR^{6a}R^{7a}$ or $OR^7$.

Further preferred methods of the present invention are methods wherein in the compound of Formulae (1) or (2), Ar is phenyl, pyridyl or 2,3-dihydrobenzofuranyl, each optionally substituted with 1 to 4 $R^4$ substituents.

Further preferred methods of the present invention are methods wherein in the compound of Formulae (1) or (2), A is N, Z is $CR^2$, Ar is 2,4-dichlorophenyl, 2,4-dimethylphenyl or 2,4,6-trimethylphenyl, $R^1$ and $R^2$ are $CH_3$, and $R^3$ is $NR^{6a}R^{7a}$.

The present invention further comprises compounds of Formulae (1) or (2):

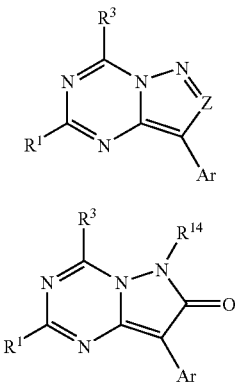

and isomers thereof, stereoisomeric forms thereof, or mixtures of stereoisomeric forms thereof, and pharmaceutically acceptable salt forms thereof wherein:

Z is N or $CR^2$;

Ar is selected from phenyl, naphthyl, pyridyl, pyrimidinyl, triazinyl, furanyl, thienyl, benzothienyl, benzofuranyl, 2,3-dihydrobenzofuranyl, 2,3-dihydrobenzothienyl, indanyl, 1,2-benzopyranyl, 3,4-dihydro-1,2-benzopyranyl, tetralinyl, each Ar optionally substituted with 1 to 5 $R^4$ groups and each Ar is attached to an unsaturated carbon atom;

$R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_2$–$C_{10}$ cyanoalkyl, $C_3$–$C_6$ cycloalkyl, $C_4$–$C_{10}$ cycloalkylalkyl, $NR^9R^{10}$, $C_1$–$C_4$ alkyl-$NR^9R^{10}$, $NR^9COR^{10}$, $OR^{11}$, SH or $S(O)_nR^{12}$;

$R^2$ is selected from H, $C_1$–$C_4$ alkyl, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, halo, CN, —$NR^6R^7$, $NR^9COR^{10}$, —$NR^6S(O)_nR^7$, $S(O)_nNR^6R^7$, $C_1$–$C_4$ haloalkyl, —$OR^7$, SH or —$S(O)_nR^{12}$;

$R^3$ is selected from:
— H, $OR^7$, SH, $S(O)_nR^{13}$, $COR^7$, $CO_2R^7$, $OC(O)R^{13}$, $NR^8COR^7$, $N(COR^7)_2$, $NR^8CONR^6R^7$, $NR^8CO_2R^{13}$, $NR^6R^7$, $NR^{6a}R^{7a}$, $N(OR^7)R^6$, $CONR^6R^7$, aryl, heteroaryl and heterocyclyl, or
— $C_1$–$C_{10}$ alkyl, $C_2$–$C_{10}$ alkenyl, $C_2$–$C_{10}$ alkynyl, $C_3$–$C_8$ cycloalkyl, $C_5$–$C_8$ cycloalkenyl, $C_4$–$C_{12}$ cycloalkylalkyl or $C_6$–$C_{10}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl and heterocyclyl;

$R^4$ is independently selected at each occurrence from: $C_1$–$C_{10}$ alkyl, $C_2$–$C_{10}$ alkenyl, $C_2$–$C_{10}$ alkynyl, $C_3$–$C_6$ cycloalkyl, $C_4$–$C_{12}$ cycloalkylalkyl, $NO_2$, halo, CN, $C_1$–$C_4$ haloalkyl, $NR^6R^7$, $NR^8COR^7$, $NR^8CO_2R^7$, $COR^7$, $OR^7$, $CONR^6R^7$, $CO(NOR^9)R^7$, $CO_2R^7$, or $S(O)_nR^7$, where each such $C_1$–$C_{10}$ alkyl, $C_2$–$C_{10}$ alkenyl, $C_2$–$C_{10}$ alkynyl, $C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NO_2$, halo, CN, $NR^6R^7$, $NR^8COR^7$, $NR^8CO_2R^7$, $COR^7$ $OR^7$, $CONR^6R^7$, $CO_2R^7$, $CO(NOR^9)R^7$, or $S(O)_nR^7$;

$R^6$, $R^7$, $R^{6a}$ and $R^{7a}$ are independently selected at each occurrence from:
— H,
— $C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups;

$R^8$ is independently selected at each occurrence from H or $C_1$–$C_4$ alkyl;

$R^9$ and $R^{10}$ are independently selected at each occurrence from H, $C_1$–$C_4$ alkyl, or $C_3$–$C_6$ cycloalkyl;

$R^{11}$ is selected from H, $C_1$–$C_4$ alkyl, $C_1$–$C_4$ haloalkyl, or $C_3$–$C_6$ cycloalkyl;

$R^{12}$ is $C_1$–$C_4$ alkyl or $C_1$–$C_4$ haloalkyl;

$R^{13}$ is selected from $C_1$–$C_4$ alkyl, $C_1$–$C_4$ haloalkyl, $C_2$–$C_8$ alkoxyalkyl, $C_3$–$C_6$ cycloalkyl, $C_4$–$C_{12}$ cycloalkylalkyl, aryl, aryl($C_1$–$C_4$ alkyl)-, heteroaryl or heteroaryl($C_1$–$C_4$ alkyl)-;

$R^{14}$ is selected from $C_1$–$C_{10}$ alkyl, $C_3$–$C_{10}$ alkenyl, $C_3$–$C_{10}$ alkynyl, $C_3$–$C_8$ cycloalkyl, or $C_4$–$C_{12}$ cycloalkylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, $CONR^{16}R^{15}$, and $C_1$–$C_6$ alkylthio, $C_1$–$C_6$ alkylsulfinyl and $C_1$–$C_6$ alkylsulfonyl;

$R^{15}$ and $R^{16}$ are independently selected at each occurrence from H, $C_1$–$C_6$ alkyl, $C_3$–$C_{10}$ cycloalkyl, $C_4$–$C_{16}$ cycloalkylalkyl, except that for $S(O)_nR^{15}$, $R^{15}$ cannot be H;

aryl is phenyl or naphthyl, each optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heteroaryl is pyridyl, pyrimidinyl, triazinyl, furanyl, pyranyl, quinolinyl, isoquinolinyl, thienyl, imidazolyl, thiazolyl, indolyl, pyrrolyl, oxazolyl, benzofuranyl, benzothienyl, benzothiazolyl, isoxazolyl, pyrazolyl, 2,3-dihydrobenzothienyl or 2,3-dihydrobenzofuranyl, each being optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, —$COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{16}R^{15}$, and $CONR^{16}R^{15}$;

heterocyclyl is saturated or partially saturated heteroaryl, optionally substituted with 1 to 5 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{15}$, $COR^{15}$, $CO_2R^{15}$, $OC(O)R^{15}$, $NR^8COR^{15}$, $N(COR^{15})_2$, $NR^8CONR^{16}R^{15}$, $NR^8CO_2R^{15}$, $NR^{15}R^{16}$, and $CONR^{16}R^{15}$;

n is independently at each occurrence 0, 1 or 2;

with the provisos that:
(1) when Z is $CR^2$ and $R^2$ is H and $R^3$ is $OCR^{13}$ and $R^7$ is H, then $R^1$ is not H, OH or SH;
(2) when Z is $CR^2$ and $R^1$ is $CH_3$ or $C_2H_5$ and $R^2$ is H, and $R^3$ is H, $CH_3$, $C_2H_5$, $C_6H_5$, n-$C_3H_7$, i-$C_3H_7$, SH or $SCH_3$, then Ar is not phenyl or m-$CH_3$-phenyl;
(3) when Z is $CR^2$ and $R^2$ is —$NR^6SO_2R^7$ or —$SO_2NR^6R^7$, then $R^3$ is not SH; and
(4) when Z is $CR_2$, then $R^3$ is not $NR^6R^7$, $NR^{6a}R^{7a}$ or $OR^7$.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein Ar is phenyl, pyridyl or 2,3-dihydrobenzofuranyl, each optionally substituted with 1 to 4 $R^4$ substituents.

The present invention further provides for a pharmaceutical composition comprising a pharmaceutically acceptable carrier and a therapeutically effective amount of a compound of formula (1) or 2.

Further preferred compounds of the present invention include compounds of Formula (2) and isomers thereof, stereoisomeric forms thereof, or mixtures of stereoisomeric forms thereof, and pharmaceutically acceptable salt forms thereof.

Further preferred compounds of the present invention include compounds of formula (2) and isomers thereof, stereoisomeric forms thereof, or mixtures of stereoisomeric forms thereof, and pharmaceutically acceptable salt forms thereof wherein Ar is phenyl, pyridyl or 2,3-dihydrobenzofuranyl and each Ar is optionally substituted with 1 to 4 $R^4$ substituents.

Further preferred compounds of the present invention include compounds of formula (2) and isomers thereof, stereoisomeric forms thereof, or mixtures of stereoisomeric forms thereof, and pharmaceutically acceptable salt forms thereof wherein $R^3$ is $NR^{6a}R^{7a}$ or $OR^7$.

Further preferred compounds of the present invention include compounds of formula (2) and isomers thereof, stereoisomeric forms thereof, or mixtures of stereoisomeric forms thereof, and pharmaceutically acceptable salt forms thereof wherein Ar is phenyl, pyridyl or 2,3-dihydrobenzofuranyl, and each Ar is optionally substituted with 1 to 4 $R^4$ substituents, and $R^3$ is $NR^{6a}R^{7a}$ or $OR^7$.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein Z is $CR^2$.

Further preferred compounds of the present invention include compounds of formula (1) and isomers thereof, stereoisomeric forms thereof, or mixtures of stereoisomeric forms thereof, and pharmaceutically acceptable salt forms thereof wherein Ar is phenyl, pyridyl or 2,3-dihydrobenzofuranyl and each Ar is optionally substituted with 1 to 4 $R^4$ substituents.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein:

$R^{6a}$ is independently selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_1$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl); and $R^{7a}$ is independently selected at each occurrence from:
—H,
—$C_5$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_5$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

alternatively, $NR^6R^7$ and $NR^{6a}R^{7a}$ are independently piperidine, pyrrolidine, piperazine, N-methylpiperazine, morpholine or thiomorpholine, each optionally substituted with 1–3 $C_1$–$C_4$ alkyl groups.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein:

$R^{6a}$ and $R^{7a}$ are identical and are selected from:
—$C_1$–$C_4$ alkyl or $C_3$–$C_6$ cycloalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, —$COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, and -aryl or heteroaryl.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein:

$R^{6a}$ is selected from:
—H,
—$C_1$–$C_{10}$ alkyl, $C_3$–$C_{10}$ alkenyl, $C_3$–$C_{10}$ alkynyl, $C_1$–$C_{10}$ haloalkyl with 1–10 halogens, $C_2$–$C_8$ alkoxyalkyl, $C_3$–$C_6$ cycloalkyl, $C_4$–$C_{12}$ cycloalkylalkyl, $C_1$–$C_{10}$ cycloalkenyl, or $C_6$–$C_{14}$ cycloalkenylalkyl, each optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, -aryl, aryl($C_1$–$C_4$ alkyl), heteroaryl, heteroaryl($C_1$–$C_4$ alkyl), heterocyclyl or heterocyclyl($C_1$–$C_4$ alkyl);

$R^{7a}$ is selected from:

—$C_1$–$C_4$ alkyl and each such $C_1$–$C_4$ alkyl is substituted with 1–3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein:

one of $R^{6a}$ and $R^{7a}$ is selected from:

—$C_3$–$C_6$ cycloalkyl, each such $C_3$–$C_6$ cycloalkyl optionally substituted with 1–3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl, -aryl, -heteroaryl or -heterocyclyl, and the other of $R^{6a}$ and $R^{7a}$ is unsubstituted $C_1$–$C_4$ alkyl.

Further preferred compounds of the present invention include compounds of formula (1) of (2) and isomers thereof, stereoisomeric forms thereof, or mixtures of stereoisomeric forms thereof, and pharmaceutically acceptable salt forms thereof wherein $R^{6a}$ and $R^{7a}$ are independently H or $C_1$–$C_{10}$ alkyl, each such $C_1$–$C_{10}$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $R^8CONR^{16}R^{15}$, $NR^8CO_2R^{13}$, $NR^{16}R^{15}$, $CONR^{16}R^{15}$, aryl, heteroaryl or heterocyclyl.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein Ar is phenyl, pyridyl or 2,3-dihydrobenzofuranyl, and each Ar is optionally substituted with 1 to 4 $R^4$ substituents.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein —Ar is phenyl, pyridyl or 2,3-dihydrobenzofuranyl, and each Ar is optionally substituted with 1 to 4 $R^4$ substituents, —$R^1$ and $R^2$ are independently selected from H, $C_1$–$C_4$ alkyl, $C_3$–$C_6$ cycloalkyl, $C_4$–$C_{10}$ cycloalkylalkyl.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein $R^{6a}$ and $R^{7a}$ are independently H or $C_1$–$C_{10}$ alkyl, each such $C_1$–$C_{10}$ alkyl optionally substituted with 1 to 3 substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $R^8CONR^{16}R^{15}$, $NR^8CO_2R^{13}$, $NR^{16}R^{15}$, $CONR^{16}R^{15}$, aryl, heteroaryl or heterocyclyl.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein $R^1$ is independently selected at each occurrence from H, $C_1$–$C_4$ alkyl, $C_2$–$C_4$ alkenyl, $C_2$–$C_4$ alkynyl, halo, CN, $C_1$–$C_4$ haloalkyl, $C_1$–$C_{12}$ hydroxyalkyl, $C_2$–$C_{12}$ alkoxyalkyl, $C_3$–$C_6$ cycloalkyl, $C_4$–$C_{10}$ cycloalkylalkyl.

Further preferred compounds of the present invention include compounds formula (1) or (2) and isomers thereof, stereoisomeric forms thereof, or mixtures of stereoisomeric forms thereof, and pharmaceutically acceptable salt forms thereof wherein $R^2$ is selected from H, $C_1$–$C_4$ alkyl, $C_2$–$C_4$ alkenyl, $C_2$–$C_4$ alkynyl, $C_3$–$C_6$ cycloalkyl, $C_4$–$C_{10}$ cycloalkylalkyl, $C_1$–$C_4$ hydroxyalkyl, halo, CN, —$NR^6R^7$, $C_1$–$C_4$ haloalkyl, —$OR^7$.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein $R^4$ is independently selected at each occurrence from: $C_1$–$C_{10}$ alkyl, $C_2$–$C_{10}$ alkenyl, $C_3$–$C_6$ cycloalkyl, $C_4$–$C_{12}$ cycloalkylalkyl, halo, CN, $C_1$–$C_4$ haloalkyl, $NR^6R^7$, $COR^7$, $OR^7$, where each such $C_1$–$C_{10}$ alkyl, $C_2$–$C_{10}$ alkenyl, $C_2$–$C_3$–$C_6$ cycloalkyl and $C_4$–$C_{12}$ cycloalkylalkyl are optionally substituted with 1 to 3 substituents independently selected at each occurrence from $C_1$–$C_4$ alkyl, $NR^6R^7$, $COR^7$ $OR^7$, $CO_2R^7$.

Further preferred compounds of the present invention include compounds of formula (1) or (2) and isomers thereof, stereoisomeric forms thereof, or mixtures of stereoisomeric forms thereof, and pharmaceutically acceptable salt forms thereof wherein $R^4$ is independently selected at each occurrence from: H, $C_1$–$C_{10}$ alkyl, $C_1$–$C_4$ alkoxy, halo, CN and —$NR^6R^7$.

The present invention further provides for a pharmaceutical composition comprising a pharmaceutically acceptable carrier and a therapeutically effective amount of a compound of formula (1) or (2).

The present invention further provides for a method of treating affective disorder, anxiety, depression, headache, irritable bowel syndrome, posttraumatic stress disorder, supranuclear palsy, immune suppression, Alzheimer's disease, gastrointestinal diseases, anorexia nervosa or other feeding disorder, drug addiction, drug or alcohol withdrawal symptoms, inflammatory diseases, cardiovascular or heart-related diseases, fertility problems, human immunodeficiency virus infections, hemorrhagic stress, obesity, infertility, head and spinal cord traumas, epilepsy, stroke, ulcers, amyotrophic lateral sclerosis, hypoglycemia or a disorder the treatment of which can be effected or facilitated by antagonizing CRF, including but not limited to disorders induced or facilitated by CRF, in mammals comprising administering to the mammal a therapeutically effective amount of a compound of formula (1) or (2).

Many compounds of this invention have one or more asymmetric centers or planes. Unless otherwise indicated, all chiral (enantiomeric and diastereomeric) and racemic forms are included in the present invention. Many geometric isomers of olefins, C=N double bonds, and the like can also be present in the compounds, and all such stable isomers are contemplated in the present invention. The compounds may be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated.

The term "alkyl" includes both branched and straight-chain alkyl having the specified number of carbon atoms. Commonly used abbreviations have the following meanings: Me is methyl, Et is ethyl, Pr is propyl, Bu is butyl. As is conventional, in a chemical structure drawing, a straight single bond attached to an atom at one end but with no atom designation at the other end indicates the presence of a methyl group at the unattached end of the bond. The prefix "n" means a straight chain alkyl. The prefix "c" means a cycloalkyl. The prefix "(S)" means the S enantiomer and the prefix "(R)" means the R enantiomer. Alkenyl" includes hydrocarbon chains of either a straight or branched configuration and one or more unsaturated carbon—carbon bonds which may occur in any stable point along the chain, such as ethenyl, propenyl, and the like. "Alkynyl" includes hydrocarbon chains of either a straight or branched configuration and one or more triple carbon—carbon bonds which may occur in any stable point along the chain, such as ethynyl, propynyl and the like. "Haloalkyl" is intended to include both branched and straight-chain alkyl having the specified number of carbon atoms, substituted with 1 or more halogen; "alkoxy" represents an alkyl group of indicated number of carbon atoms attached through an oxygen bridge; "cycloalkyl" is intended to include saturated ring groups, including mono-,bi- or poly-cyclic ring systems, such as cyclopropyl, cyclobutyl, cyclopentyl, cyclohexyl, and so forth. "Halo" or "halogen" includes fluoro, chloro, bromo, and iodo.

The term "substituted", as used herein, means that one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "appropriate amino acid protecting group" means any group known in the art of organic synthesis for the protection of amine or carboxylic acid groups. Such amine protecting groups include those listed in Greene and Wuts, "Protective Groups in Organic Synthesis" John Wiley & Sons, New York (1991) and "The Peptides: Analysis, Synthesis, Biology, Vol. 3, Academic Press, New York (1981), the disclosure of which is hereby incorporated by reference. Any amine protecting group known in the art can be used. Examples of amine protecting groups include, but are not limited to, the following: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl.

The term "pharmaceutically acceptable salts" includes acid or base salts of the compounds of Formulae (1) and (2). Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are considered to be any covalently bonded carriers which release the active parent drug of formula (I) or (II) in vivo when such prodrug is administered to a mammalian subject. Prodrugs of the compounds of formula (I) and (II) are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups in the compounds of formulas (I) and (II); and the like.

The term "therapeutically effective amount" of a compound of this invention means an amount effective to antagonize abnormal level of CRF or treat the symptoms of affective disorder, anxiety or depression in a host.

Syntheses

Some compounds of Formula (1) may be prepared from intermediate compounds of Formula (7), using the procedures outlined in Scheme 1:

SCHEME 1

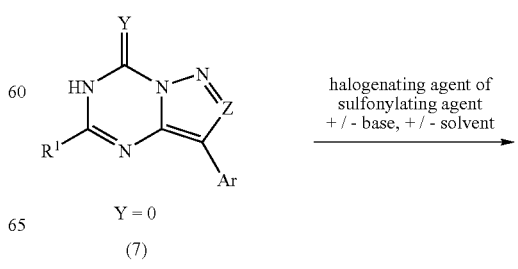

Y = 0

(7)

halogenating agent of sulfonylating agent
+ / − base, + / − solvent

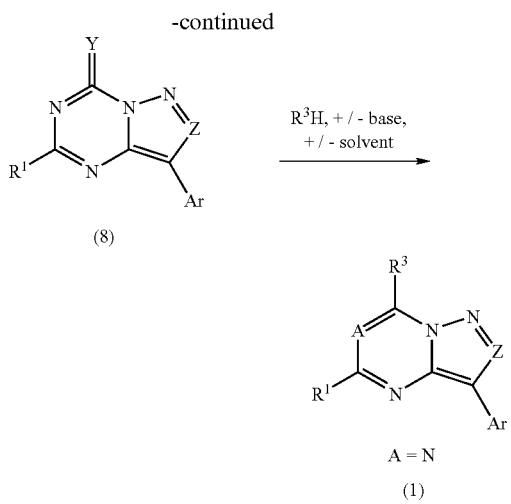

Compounds of Formula (7) (where Y is O) may be treated with a halogenating agent or sulfonylating agent in the presence or absence of a base in the presence or absence of an inert solvent at reaction temperatures ranging from −80° C. to 250° C. to give products of Formula (8) (where X is halogen, alkanesulfonyloxy, arylsulfonyloxy or haloalkanesulfonyloxy). Halogenating agents include, but are not limited to, $SOCl_2$, $POCl_3$, $PCl_3$, $PCl_5$, $POBr_3$, $PBr_3$ or $PBr_5$. Sulfonylating agents include, but are not limited to, alkanesulfonyl halides or anhydrides (such as methanesulfonyl chloride or methanesulfonic acid anhydride), arylsulfonyl halides or anhydrides (such as p-toluenesulfonyl chloride or anhydride) or haloalkylsulfonyl halides or anhydrides (preferably trifluoromethanesulfonic anhydride). Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20° C. to 100° C.

Compounds of Formula (8) may be reacted with compounds of Formula $R^3H$ (where $R^3$ is defined as above except $R^3$ is not SH, $COR^7$, $CO_2R^7$, aryl or heteroaryl) in the presence or absence of a base in the presence or absence of an inert solvent at reaction temperatures ranging from −80 to 250° C. to generate compounds of Formula (1). Bases may include, but are not limited to, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal carbonates, alkali metal bicarbonates, alkali metal bis(trialkylsilyl)amides (preferably sodium bis(trimethylsilyl)amide), trialkyl amines (preferably N,N-di-isopropyl-N-ethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from 0° C. to 140° C.

Scheme 2 delineates the procedures for converting intermediate compounds of Formula (7) (where Y is S) to some compounds of Formula (1).

SCHEME 2

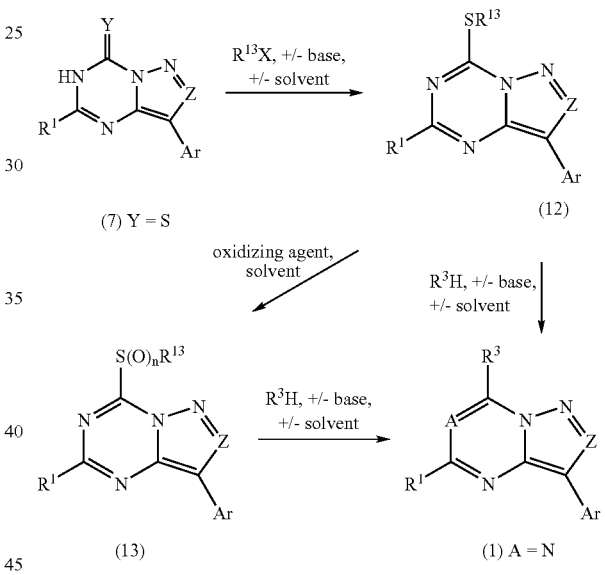

Compounds of Formula (7) (where Y is S) may be treated with an alkylating agent $R^{13}X$ (where $R^{13}$ is defined as above, except $R^{13}$ is not aryl or heteroaryl) in the presence or absence of a base in the presence or absence of an inert solvent at reaction temperatures ranging from −80° C. to 250° C. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal hydroxides, alkali metal bis (trialkylsilyl)amides (preferably sodium bis(trimethylsilyl) amide), trialkyl amines (prefereably N,N-di-isopropyl-N-ethyl amine or triethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −80° C. to 100° C.

Compounds of Formula (12) (Formula (1) where $R^3$ is $SR^{13}$) may then be reacted with compounds of Formula $R^3H$ to give compounds of Formula (1), using the same conditions and reagents as were used for the conversion of compounds of Formula (8) to compounds of Formula (1) as outlined for Scheme 1 above. Alternatively, compounds of Formula (12) (Formula (1) where $R^3$ is $SR^{13}$) may be oxidized to compounds of Formula (13) (Formula (1) where $R^3$ is $S(O)_nR^{13}$, n is 1,2) by treatment with an oxidizing agent in the presence of an inert solvent at temperatures ranging from −80° C. to 250° C. Oxidizing agents include, but are not limited to, hydrogen peroxide, alkane or aryl peracids (preferably peracetic acid or m-chloroperbenzoic acid), dioxirane, oxone, or sodium periodate. Inert solvents may include, but are not limited to, alkanones (3 to 10 carbons, preferably acetone), water, alkyl alcohols (1 to 6 carbons), aromatic hydrocarbons (preferably benzene or toluene) or haloalkanes of 1 to 10 carbons and 1 to 10 halogens (preferably dichloromethane) or combinations thereof. The choices of oxidant and solvent are known to those skilled in the art (cf. Uemura, S., Oxidation of Sulfur, Selenium and Tellurium, in *Comprehensive Organic Synthesis*, Trost, B. M. ed., (Elmsford, N.Y.: Pergamon Press, 1991), 7, 762–769). Preferred reaction temperatures range from −20° C. to 100° C. Compounds of Formula (13) (Formula (1) where $R^3$ is $S(O)_nR^{13}$ n is 1,2) may then be reacted with compounds of Formula $R^3H$ to give compounds of Formula (1), using the same conditions and reagents as were used for the conversion of compounds of Formula (8) to compounds of Formula (1) as outlined for Scheme (1) above.

Compounds of Formula (1), where $R^3$ may be $-NR^8COR^7$, $-N(COR^7)_2$, $-NR^8CONR^6R^7$, $-NR^8CO_2R^{13}$, $-NR^6R^7$, $NR^8SO_2R^7$, may be prepared from compounds of Formula (7), where Y is NH, by the procedures depicted in Scheme 3.

SCHEME 3

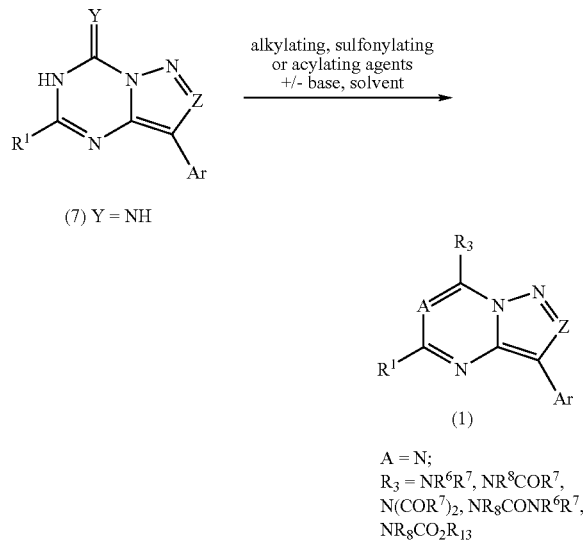

(7) Y = NH

A = N;
$R_3$ = $NR^6R^7$, $NR^8COR^7$,
$N(COR^7)_2$, $NR_8CONR^6R^7$,
$NR_8CO_2R_{13}$

Reaction of compounds of Formula (7), where Y is NH, with alkylating agents, sulfonylating agents or acylating agents or sequential reactions with combinations thereof, in the presence or absence of a base in an inert solvent at reaction temperatures ranging from −80° C. to 250° C. may afford compounds of Formula (1), where $R^3$ may be $-NR^8COR^7$, $-N(COR^7)_2$, $-NR^8CONR^6R^7$, $-NR^8CO_2R^{13}$, $-NR^6R^7$, $-NR^8SO_2R^7$. Alkylating agents may include, but are not limited to, $C_1-C_{10}$ alkyl -halides, -tosylates, -mesylates or -triflates; $C_1-C_{10}$ haloalkyl(1–10 halogens)-halides, -tosylates, -mesylates or -triflates; $C_2-C_8$ alkoxyalkyl-halides, -tosylates, -mesylates or -triflates; $C_3-C_6$ cycloalkyl-halides, -tosylates, -mesylates or -triflates; $C_4-C_{12}$ cycloalkylalkyl-halides, -tosylates, -mesylates or -triflates; aryl($C_1-C_4$ alkyl)-halides, -tosylates, -mesylates or -triflates; heteroaryl($C_1-C_4$ alkyl)-halides, -tosylates, -mesylates or -triflates; or heterocyclyl($C_1-C_4$ alkyl)-halides, -tosylates, -mesylates or -triflates. Acylating agents may include, but are not limited to, $C_1-C_{10}$ alkanoyl halides or anhydrides, $C_1-C_{10}$ haloalkanoyl halides or anhydrides with 1–10 halogens, $C_2-C_8$ alkoxyalkanoyl halides or anhydrides, $C_3-C_6$ cycloalkanoyl halides or anhydrides, $C_4-C_{12}$ cycloalkylalkanoyl halides or anhydrides, aroyl halides or anhydrides, aryl($C_1-C_4$) alkanoyl halides or anhydrides, heteroaroyl halides or anhydrides, heteroaryl($C_1-C_4$) alkanoyl halides or anhydrides, heterocyclylcarboxylic acid halides or anhydrides or heterocyclyl($C_1-C_4$) alkanoyl halides or anhydrides. Sulfonylating agents include, but are not limited to, $C_1-C_{10}$ alkylsulfonyl halides or anhydrides, $C_1-C_{10}$ haloalkylsulfonyl halides or anhydrides with 1–10 halogens, $C_2-C_8$ alkoxyalkylsulfonyl halides or anhydrides, $C_3-C_6$ cycloalkylsulfonyl halides or anhydrides, $C_4-C_{12}$ cycloalkylalkylsulfonyl halides or anhydrides, arylsulfonyl halides or anhydrides, aryl($C_1-C_4$ alkyl)-, heteroarylsulfonyl halides or anhydrides, heteroaryl($C_1-C_4$ alkyl)sulfonyl halides or anhydrides, heterocyclylsulfonyl halides or anhydrides or heterocyclyl($C_1-C_4$ alkyl)sulfonyl halides or anhydrides. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C.

Scheme 4 delineates procedures, which may be employed to prepare intermediate compounds of Formula (7), where Y is O, S and Z is $CR^2$.

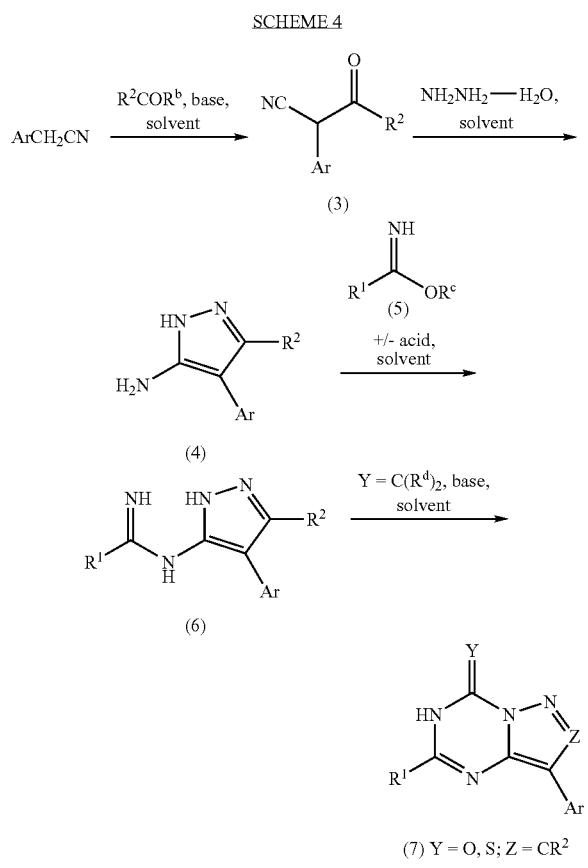

Compounds of the formula ArCH$_2$CN are reacted with compounds of the formula R$^2$COR$^b$, where R$^2$ is defined above and R$^b$ is halogen, cyano, lower alkoxy (1 to 6 carbons) or lower alkanoyloxy (1 to 6 carbons), in the presence of a base in an inert solvent at reaction temperatures ranging from −78° C. to 200° C. to afford compounds of Formula (3). Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal hydroxides, alkali metal bis(trialkylsilyl)amides (preferably sodium bis(trimethylsilyl)amide), trialkyl amines (preferably N,N-di-isopropyl-N-ethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), water, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C.

Compounds of Formula (3) may be treated with hydrazine-hydrate in the presence of an inert solvent at temperatures ranging from 0° C. to 200° C., preferably 70° C. to 150° C., to produce compounds of Formula (4). Inert solvents may include, but are not limited to, water, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Compounds of Formula (4) may be reacted with compounds of Formula (5) (where R$^c$ is alkyl (1–6 carbons)) in the presence or absence of an acid in the presence of an inert solvent at temperatures ranging from 0° C. to 200° C. to produce compounds of Formula (6). Acids may include, but are not limited to alkanoic acids of 2 to 10 carbons (preferably acetic acid), haloalkanoic acids (2–10 carbons, 1–10 halogens, such as trifluoroacetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Inert solvents may include, but are not limited to, water, alkanenitriles (1 to 6 carbons, preferably acetonitrile), halocarbons of 1 to 6 carbons and 1 to 6 halogens (preferably dichloromethane or chloroform), alkyl alcohols of 1 to 10 carbons (preferably ethanol), dialkyl ethers (4 to 12 carbons, preferably diethyl ether or di-isopropylether) or cyclic ethers such as dioxan or tetrahydrofuran. Preferred temperatures range from ambient temperature to 100° C.

Compounds of Formula (6) may be converted to intermediate compounds of Formula (7) by treatment with compounds C=Y(R$^d$)$_2$ (where Y is O or S and R$^d$ is halogen (preferably chlorine), alkoxy (1 to 4 carbons) or alkylthio (1 to 4 carbons)) in the presence or absence of a base in an inert solvent at reaction temperatures from −50° C. to 200° C. Bases may include, but are not limited to, alkali metal hydrides (preferably sodium hydride), alkali metal alkoxides (1 to 6 carbons)(preferably sodium methoxide or sodium ethoxide), alkali metal carbonates, alkali metal hydroxides, trialkyl amines (preferably N,N-diisopropyl-N-ethyl amine or triethylamine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred temperatures are 0° C. to 150° C.

Intermediate compounds of Formula (7), where Z is N, may be synthesized according the methods

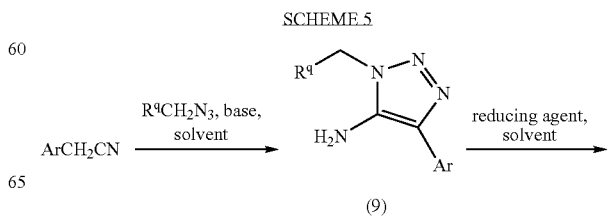

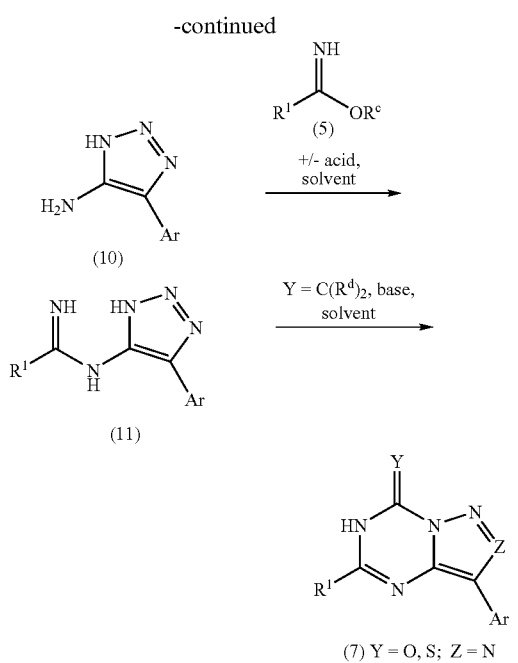

erably acetonitrile), water, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). The preferred reaction temperatures are −50° C. to 60° C. Compounds of Formula (9) are then converted to compounds of Formula (7) (where Z is N) via intermediates of Formula (11) using the reagents and reaction conditions outlined in Scheme 4 for the conversion of compounds of Formula (4) to compounds of Formula (7) (where Z is $CR^2$).

Compounds of Formula (1) may also be prepared from compounds of Formula (7) (where Y is O, S and Z is defined above) as outlined in Scheme 6:

SCHEME 6

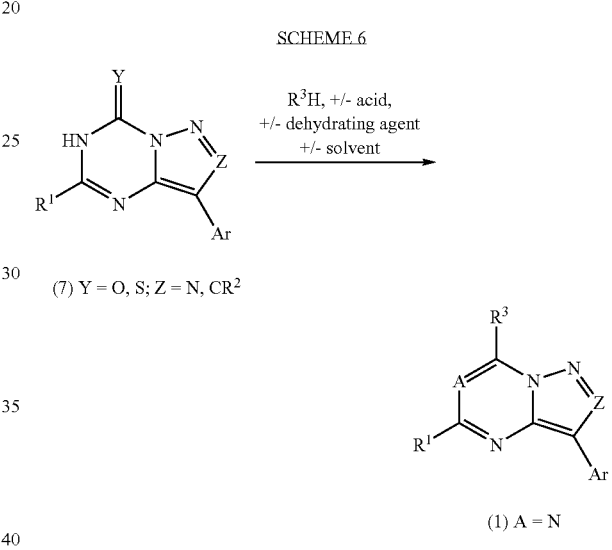

Compounds of Formula (7) may be reacted with compounds of Formula $R^3H$ in the presence of a dehydrating agent in an inert solvent at reaction temperatures ranging from 0° C. to 250° C. Dehydrating agents include, but are not limited to, $P_2O_5$, molecular sieves or inorganic or organic acids. Acids may include, but are not limited to alkanoic acids of 2 to 10 carbons (preferably acetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Inert solvents may include, but are not limited to, alkyl alcohols (1 to 8 carbons, preferably methanol or ethanol), lower alkanenitriles (1 to 6 carbons, preferably acetonitrile), dialkyl ethers (preferably glyme or diglyme), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or halocarbons of 1 to 10 carbons and 1 to 10 halogens (preferably chloroform). Preferred reaction temperatures range from ambient temperature to 150° C.

Compounds of ArCH$_2$CN are reacted with compounds of Formula $R^qCH_2N_3$ (where $R^q$ is a phenyl group optionally substituted by H, alkyl (1 to 6 carbons) or alkoxy (1 to 6 carbons) in the presence or absence of a base in an inert solvent at temperatures ranging from 0° C. to 200° C. to generate compounds of Formula (9). Bases may include, but are not limited to, alkali metal hydrides (preferably sodium hydride), alkali metal alkoxides (1 to 6 carbons)(preferably sodium methoxide, sodium ethoxide or potassium t-butoxide), alkaline earth metal hydrides, alkali metal dialkylamides (preferably lithium di-isopropylamide), alkali metal carbonates, alkali metal hydroxides, alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from ambient temperature to 100° C. Compounds of Formula (9) may be treated with a reducing agent in an inert solvent at 100° C. to 100° C. to afford products of Formula (10). Reducing agents include, but are not limited to, (a) hydrogen gas in combination with noble metal catalysts such as Pd-on-carbon, $PtO_2$, Pt-on-carbon, Rh-on-alumina or Raney nickel, (b) alkali metals (preferably sodium) in combination with liquid ammonia or (c) ceric ammonium nitrate. Inert solvents may include, but are not limited to, alkyl alcohols (1 to 8 carbons, preferably methanol or ethanol), lower alkanenitriles (1 to 6 carbons, pref- Some compounds of Formula (1) (where A is N) may also be prepared by the methods shown in Scheme 7:

SCHEME 7

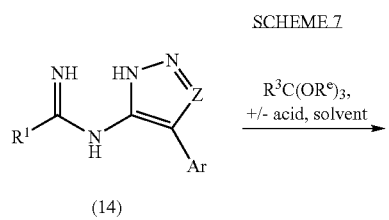

(14)

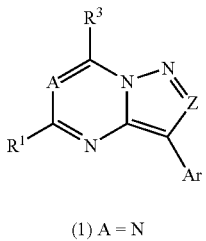

(1) A = N

Intermediate compounds of Formula (14), where Z is defined above, may be reacted with compounds of Formula $R^3C(OR^e)_3$, where $R^e$ may be alkyl (1 to 6 carbons) in the presence or absence of an acid in an inert solvent at temperatures ranging from 0° C. to 250° C. Acids may include, but are not limited to alkanoic acids of 2 to 10 carbons (preferably acetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from 50° C. to 150° C.

Intermediate compounds of Formula (7) may also be synthesized by the reactions displayed in Scheme 8.

SCHEME 8

![structure with Y, A, R¹, N-N, Z, X] ArM, +/- catalyst, solvent →

(15) Y = OH, SH NR⁶R⁷;
Z = N, CR²,
X = Br, Cl, I, B(OR'''')2

![structure] (7) A = N

Compounds of Formula (15), (where Y is OH, SH, $NR^6R^7$; Z is defined above, X is Br, Cl, I, $O_3SCF_3$ or $B(OR'''')_2$ and R'''' is H or alkyl (1 to 6 carbons)) may be reacted with a compound of Formula ArM (where M is halogen, alkali metal, ZnCl, ZnBr, ZnI, MgBr, MgCl, MgI, $CeCl_2$, $CeBr_2$ or copper halides) in the presence or absence of an organometallic catalyst in the presence or absence of a base in an inert solvents at temperatures ranging from –100° C. to 200° C. Those skilled in the art will recognize that the reagents ArM may be generated in situ. Organometallic catalysts include, but are not limited to, palladium phosphine complexes (such as $Pd(PPh_3)_4$), palladium halides or alkanoates (such as $PdCl_2(PPh_3)_2$ or $Pd(OAc)_2$) or nickel complexes (such as $NiCl_2(PPh_3)_2$). Bases may include, but are not limited to, alkali metal carbonates or trialkyl amines (preferably N,N-di-isopropyl-N-ethyl amine or triethylamine). Inert solvents may include, but are not limited to, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or water. Preferred reaction temperatures range from 80° C. to 100° C.

The choices of M and X are known to those skilled in the art (of Imamoto, T., Organocerium Reagents in *Comprehensive Organic Synthesis*, Trost, B. M. ed., (Elmsford, N.Y.: Pergamon Press, 1991), 1, 231–250; Knochel, P., Organozinc, Organocadmium and Organomercury Reagents in *Comprehensive Organic Synthesis*, Trost, B. M. ed., (Elmsford, N.Y.: Pergamon Press, 1991), 1, 211–230; Knight, D. W., Coupling Reactions between sp² Carbon Centers, in *Comprehensive Organic Synthesis*, Trost, B. M. ed., (Elmsford, N.Y.: Pergamon Press, 1991), 3, 481–520).

Compounds of Formula (1) may also be prepared using the methods shown in Scheme 9.

SCHEME 9

![structure] ArM, +/- catalyst, solvent →

(16) X = Br, Cl, I,
B(OR'''')₂, O₃SCF₃

-continued

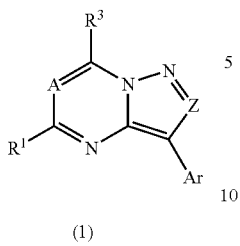

(1)

-continued

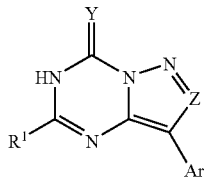

(7) Y = O, S, NH; Z = CR²,

Compounds of Formula (16), where A, Z, R¹ and R³ are defined above and X is Br, Cl, I, O₃SCF₃ or B(OR'''')₂ and R'''' is H or alkyl (1 to 6 carbons)) may be reacted with a compound of Formula ArM (where M is halogen, alkali metal, ZnCl, ZnBr, ZnI, MgBr, MgCl, MgI, CeCl₂, CeBr₂ or copper halides) in the presence or absence of an organometallic catalyst in the presence or absence of a base in an inert solvents at temperatures ranging from −100° C. to 200° C. Those skilled in the art will recognize that the reagents ArM may be generated in situ (see the above references in *Comprehensive Organic Synthesis*). Organometallic catalysts include, but are not limited to, palladium phosphine complexes (such as Pd(PPh₃)₄), palladium halides or alkanoates (such as PdCl₂(PPh₃)₂ or Pd(OAc)₂) or nickel complexes (such as NiCl₂(PPh₃)₂). Bases may include, but are not limited to, alkali metal carbonates or trialkyl amines (preferably N,N-diisopropyl-N-ethyl amine or triethylamine). Inert solvents may include, but are not limited to, dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or water. Preferred reaction temperatures range from 80° C. to 100° C.

Intermediate compounds of Formula (7)(where Y is O, S, NH, Z is CR² and R¹, R² and Ar are defined as above) may be prepared as illustrated in Scheme 10.

SCHEME 10

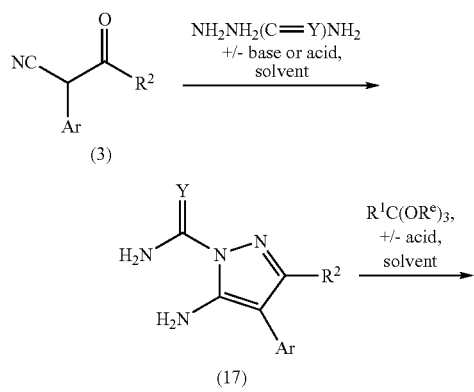

Compounds of Formula (3) may be reacted with compounds of Formula H₂NNH(C=Y)NH₂, where Y is O, S or NH, in the presence or absence of a base or acid in an inert solvent at temperatures from 0° C. to 250° C. to produce compounds of Formula (17). Acids may include, but are not limited to alkanoic acids of 2 to 10 carbons (preferably acetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, alkyl alcohols (1 to 6 carbons), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane).

Preferred reaction temperatures range from 0° C. to 150° C. Compounds of Formula (17) may then be reacted with compounds of Formula R³C(ORᵉ)₃, where Rᵉ may be alkyl (1 to 6 carbons) in the presence or absence of an acid in an inert solvent at temperatures ranging from 0° C. to 250° C. Acids may include, but are not limited to alkanoic acids of 2 to 10 carbons (preferably acetic acid), arylsulfonic acids (preferably p-toluenesulfonic acid or benzenesulfonic acid), alkanesulfonic acids of 1 to 10 carbons (preferably methanesulfonic acid), hydrochloric acid, sulfuric acid or phosphoric acid. Stoichiometric or catalytic amounts of such acids may be used. Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from 50° C. to 150° C.

In Scheme 11, the procedures which may be used to convert compounds of Formula (1), where $R^3$ is $COR^7$, $CO_2R^7$, $NR^8COR^7$ and $CONR^6R^7$, to other compounds of Formula (1), where $R^3$ is $CH(OH)R^7$, $CH_2OH$, $NR^8CH_2R^7$ and $CH_2NR^6R^7$ by treatment with a reducing agent in an inert solvent at temperatures ranging from −80° C. to 250° C.

SCHEME 11

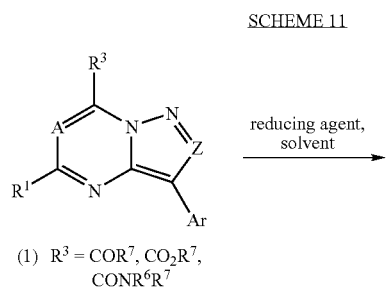

(1) $R^3 = COR^7, CO_2R^7,$
$CONR^6R^7$

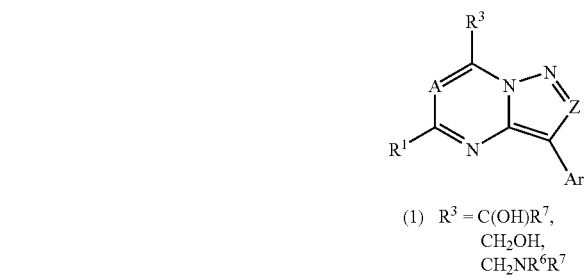

(1) $R^3 = C(OH)R^7,$
$CH_2OH,$
$CH_2NR^6R^7$

Reducing agents include, but are not limited to, alkali metal or alkaline earth metal borohydrides (preferably lithium or sodium borohydride), borane, dialkylboranes (such as di-isoamylborane), alkali metal aluminum hydrides (preferably lithium aluminum hydride), alkali metal (trialkoxy)aluminum hydrides, or dialkyl aluminum hydrides (such as di-isobutylaluminum hydride). Inert solvents may include, but are not limited to, alkyl alcohols (1 to 6 carbons), dialkyl ethers (preferably diethyl ether), cyclic ethers (preferably tetrahydrofuran or 1,4-dioxane), aromatic hydrocarbons (preferably benzene or toluene). Preferred reaction temperatures range from −80° C. to 100° C.

In Scheme 12, the procedures are shown which may be used to convert compounds of Formula (1), where $R^3$ is $COR^7$ or $CO_2R^7$, to other compounds of Formula (1), where $R^3$ is $C(OH)(R^7)_2$ by treatment with a reagent of Formula $R^7M$ in an inert solvent at temperatures ranging from −80° C. to 250° C.

SCHEME 12

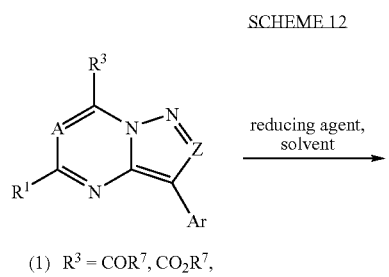

(1) $R^3 = COR^7, CO_2R^7,$

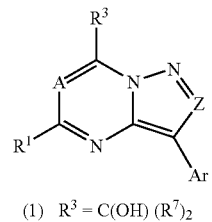

(1) $R^3 = C(OH) (R^7)_2$

M is halogen, alkali metal, $ZnCl$, $ZnBr$, $ZnI$, $MgBr$, $MgCl$, $MgI$, $CeCl_2$, $CeBr_2$ or copper halides. Inert solvents may include, but are not limited to, dialkyl ethers (preferably diethyl ether), cyclic ethers (preferably tetrahydrofuran) or aromatic hydrocarbons (preferably benzene or toluene). Preferred reaction temperatures range from −80° C. to 100° C.

Compounds of Formula (1), where $R^3$ may be $-NR^8COR^7$, $-N(COR^7)_2$, $-NR^8CONR^6R^7$, $-NR^8CO_2R^{13}$, $-NR^6R^7$, $-NR^8SO_2R^7$, may be synthesized as depicted in Scheme 13.

SCHEME 13

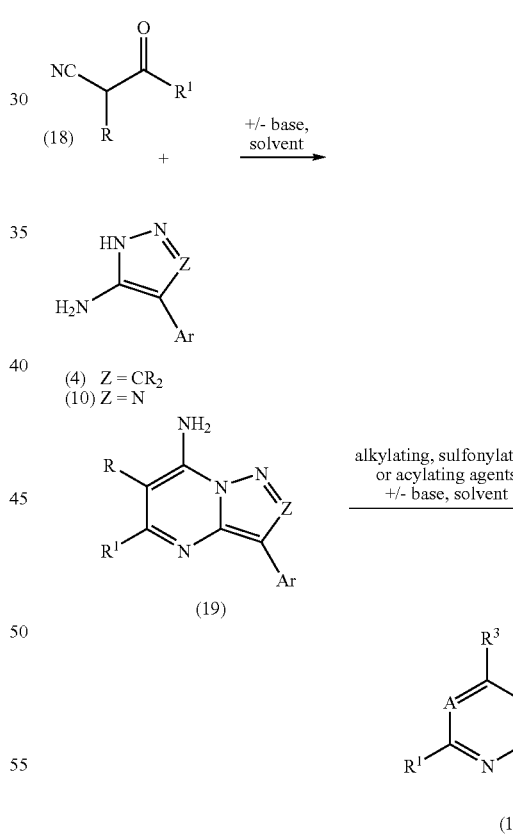

$A = CR$
$R_3 = NR^6R^7, NR^8COR^7,$
$N(COR^7)_2,$
$NR_8CONR^6R^7,$
$NR_8CO_2R_{13}$

Reaction of compounds of Formula (18), where R and $R^1$ are defined above, with compounds of Formula (4) or (10) in the presence or absence of base in an inert solvent may produce compounds of Formula (19) at temperatures ranging from −50° C. to 250° C. Bases may include, but are not limited to, alkali metal hydrides (preferably sodium hydride), alkali metal alkoxides (1 to 6 carbons) (preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C.

Compounds of Formula (19) may then be reacted with alkylating agents, sulfonylating agents or acylating agents or sequential reactions with combinations thereof, in the presence or absence of a base in an inert solvent at reaction temperatures ranging from −80° C. to 250° C. may afford compounds of Formula (1), where $R^3$ may be —$NR^8COR^7$, —$N(COR^7)_2$, —$NR^8CONR^6R^7$, —$NR^8CO_2R^{13}$, —$NR^6R^7$, —$NR^8SO_2R^7$. Alkylating agents may include, but are not limited to, $C_1$–$C_{10}$ alkyl -halides, -tosylates, -mesylates or -triflates; $C_1$–$C_{10}$ haloalkyl(1–10 halogens)-halides, -tosylates, -mesylates or -triflates; $C_2$–$C_8$ alkoxyalkyl-halides, -tosylates, -mesylates or -triflates; $C_3$–$C_6$ cycloalkyl-halides, -tosylates, -mesylates or -triflates; $C_4$–$C_{12}$ cycloalkylalkyl-halides, -tosylates, -mesylates or -triflates; aryl($C_1$–$C_4$ alkyl)-halides, -tosylates, -mesylates or -triflates; heteroaryl ($C_1$–$C_4$ alkyl)-halides, -tosylates, -mesylates or -triflates; or heterocyclyl($C_1$–$C_4$ alkyl)-halides, -tosylates, mesylates or -triflates. Acylating agents may include, but are not limited to, $C_1$–$C_{10}$ alkanoyl halides or anhydrides, $C_1$–$C_{10}$ haloalkanoyl halides or anhydrides with 1–10 halogens, $C_2$–$C_8$ alkoxyalkanoyl halides or anhydrides, $C_3$–$C_6$ cycloalkanoyl halides or anhydrides, $C_4$–$C_{12}$ cycloalkylalkanoyl halides or anhydrides, aroyl halides or anhydrides, aryl($C_1$–$C_4$) alkanoyl halides or anhydrides, heteroaroyl halides or anhydrides, heteroaryl($C_1$–$C_4$) alkanoyl halides or anhydrides, heterocyclylcarboxylic acid halides or anhydrides or heterocyclyl($C_1$–$C_4$) alkanoyl halides or anhydrides. Sulfonylating agents include, but are not limited to, $C_1$–$C_{10}$ alkylsulfonyl halides or anhydrides, $C_1$–$C_{10}$ haloalkylsulfonyl halides or anhydrides with 1–10 halogens, $C_2$–$C_8$ alkoxyalkylsulfonyl halides or anhydrides, $C_3$–$C_6$ cycloalkylsulfonyl halides or anhydrides, $C_4$–$C_{12}$ cycloalkylalkylsulfonyl halides or anhydrides, arylsulfonyl halides or anhydrides, aryl($C_1$–$C_4$ alkyl)-, heteroarylsulfonyl halides or anhydrides, heteroaryl ($C_1$–$C_4$ alkyl)sulfonyl halides or anhydrides, heterocyclylsulfonyl halides or anhydrides or heterocyclyl($C_1$–$C_4$ alkyl) sulfonyl halides or anhydrides. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic-ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C.

Compounds of Formula (1), where A is CR and R is defined above, may be synthesized by the methods depicted in Scheme 14.

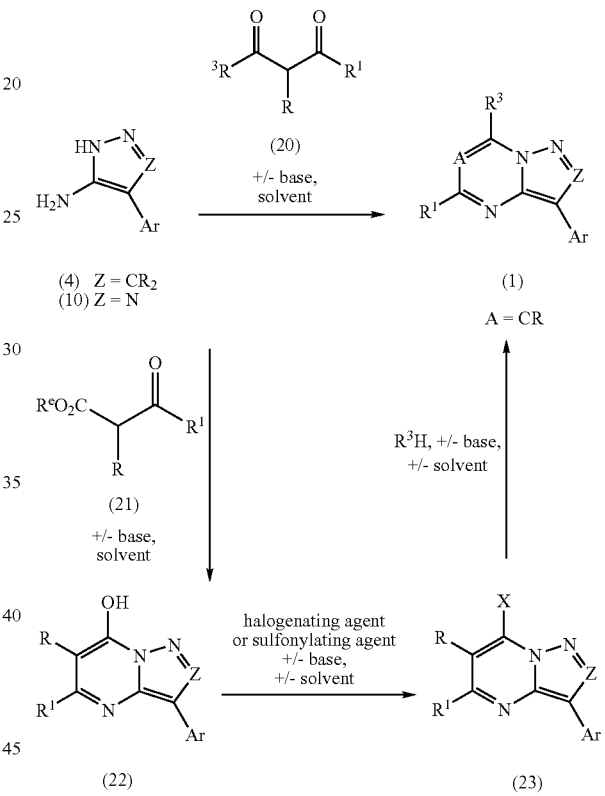

SCHEME 14

Compounds of Formula (4) or (10) may be treated with compounds of Formula (20), where $R^1$ and $R^3$ are defined above in the presence or absence of base in an inert solvent at temperatures ranging from 0° C. to 250° C. to give compounds of Formula (1), where A is CR and R is defined above. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (preferably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C. Alternatively, compounds of Formula (1) where A is CR and R is defined above, may be synthesized through intermediates (22) and (23).

Compounds of Formula (4) or (10) may be treated with compounds of Formula (21), where $R^1$ is defined above and Re is alkyl (1–6 carbons), in the presence or absence of base in an inert solvent at temperatures ranging from 0° C. to 250° C. to give compounds of Formula (1), where A is CR and R is defined above. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bis(trialkylsilyl)amides (preferably sodium bis(trimethylsilyl)amide), trialkyl amines (prefereably di-isopropylethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide) or aromatic hydrocarbons (preferably benzene or toluene). Preferred reaction temperatures range from 0° C. to 100° C. Compounds of Formula (22) may be treated with a halogenating agent or sulfonylating agent in the presence or absence of a base in the presence or absence of an inert solvent at reaction temperatures ranging from –80° C. to 250° C. to give products of Formula (23) (where X is halogen, alkanesulfonyloxy, arylsulfonyloxy or haloalkane-sulfonyloxy). Halogenating agents include, but are not limited to, $SOCl_2$, $POCl_3$, $PCl_3$, $PCl_5$, $POBr_3$, $PBr_3$ or $PBr_5$. Sulfonylating agents include, but are not limited to, alkanesulfonyl halides or anhydrides (such as methanesulfonyl chloride or methanesulfonic acid anhydride), arylsulfonyl halides or anhydrides (such as p-toluenesulfonyl chloride or anhydride) or haloalkylsulfonyl halides or anhydrides (preferably trifluoromethanesulfonic anhydride). Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from –20° C. to 100° C.

Compounds of Formula (23) may be reacted with compounds of Formula $R^3H$ (where $R^3$ is defined as above except $R^3$ is not SH, $COR^7$, $CO_2R^7$, aryl or heteroaryl) in the presence or absence of a base in the presence or absence of an inert solvent at reaction temperatures ranging from –80° C. to 250° C. to generate compounds of Formula (1). Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal carbonates, alkali metal bicarbonates, alkali metal bis(trialkylsilyl)amides (preferably sodium bis(trimethylsilyl)amide), trialkyl amines (preferably N,N-di-isopropyl-N-ethyl amine) or aromatic amines (preferably pyridine). Inert solvents may include, but are not limited to, alkyl alcohols (1 to 8 carbons, preferably methanol or ethanol), lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from 0° C. to 140° C.

Some compounds of Formula (1) may also be prepared using the methods shown in Scheme 15.

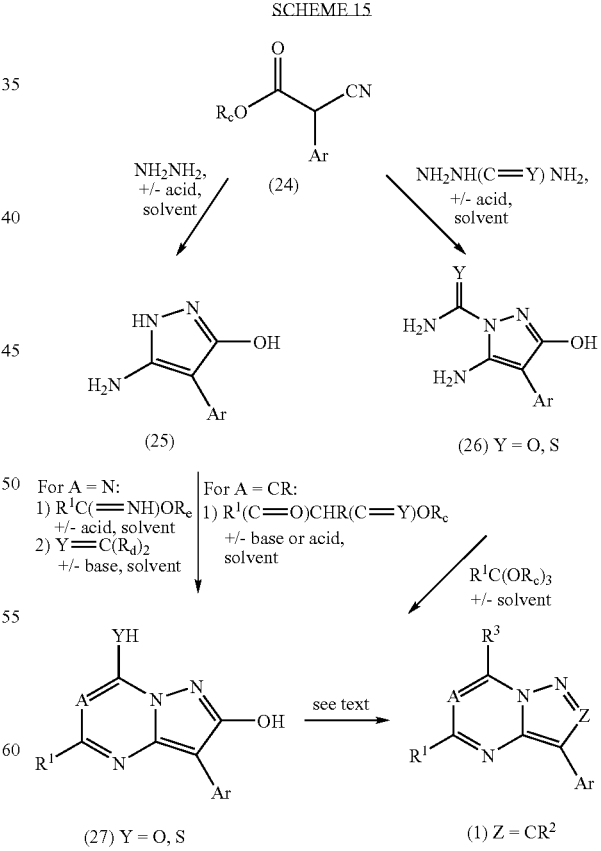

SCHEME 15

A compound of Formula (24) ($R_c$ is a lower alkyl group and Ar is defined as above) may be reacted with hydrazine in the presence or absence of an inert solvent to afford an intermediate of Formula (25), where Ar is defined as above. The conditions employed are similar to those used for the preparation of intermediate of Formula (4) from compound of Formula (3) in Scheme 4. Compounds of Formula (25), where A is N, may be reacted with reagents of the formula $R^1C(=NH)OR_e$, where $R^1$ is defined above and $R_e$ is a lower alkyl group) in the presence or absence of an acid in an inert solvent, followed by reaction with a compound of formula $YisC(R_d)2$ (where Y is O or S and $R^d$ is halogen (preferably chlorine), alkoxy (1 to 4 carbons) or alkylthio (1 to 4 carbons)) in the presence or absence of a base in an inert solvent to give compounds of Formula (27) (where A is N and Y is O, S). The conditions for these transformations are the same as those employed for the conversions of compound of Formula (4) to compound of Formula (7) in Scheme 4.

Alternatively, compounds of Formula (25), where A is CR, may be reacted with compounds of the formula $R_1(C=O)CHR(C=Y)OR_c$ (where $R^1$ and R are defined as above and $R_c$ is a lower alkyl group) to give a compound of Formula (27) (where A is CR) using conditions similar to those employed for the conversion of compounds of Formula (21) to compounds of Formula (22) in Scheme 14. Intermediates of Formula (27) (where Y is O) may be treated with halogenating agents or sulfonylating agents in the presence or absence of a base in an inert solvent, followed by reaction with $R^3H$ or $R^2H$ in the presence or absence of a base in an inert solvent to give compounds of Formula (1) (where Z is $CR^2$).

It will be recognized by those skilled in the art that various combinations of halogenating agents, sulfonylating agents, $R^3H$ or $R^2H$ may be used in different orders of reaction sequences in Scheme 15 to afford compounds of Formula (1). For example, in some cases, it may be desirable to react compounds with stoichiometric amounts of halogenating agents or sulfonylating agents, react with $R^2H$ (or $R^3H$), then repeat the reaction with halogenating agents or sulfonylating agents and react with $R^3H$ (or $R^2H$) to give compounds of Formula (1). The reaction conditions and reagents used for these conversions are similar to the ones employed for the conversion of intermediate compounds of Formulae (22) to (23) to (1) in Scheme 14 (for A is CR) or the conversion of intermediate compounds of Formulae (7) to (8) to (1) in Scheme 1 (where A is N).

Alternatively, compounds of Formula (27) (where Y is S) may be converted to compounds of Formula (1) in Scheme 15. Intermediate compounds of Formula (27) may be alkylated with a compound $R^fX$ (where $R^f$ is lower alkyl and X is halogen, alkanesulfonyloxy or haloalkanesulfonyloxy) in an inert solvent, (then optionally oxidized with an oxidizing agent in an inert solvent) and then reacted with $R^3H$ in the presence or absence of a base in an inert solvent to give a compound of Formula (1). The conditions and reagents employed are similar to those used in the conversion of intermediate compounds of Formulae (7) to (12) (or to (13)) to compounds of Formula (1) in Scheme 2.

Compounds of Formula (1) may be prepared from compounds of Formula (24), using an alternate route as depicted in Scheme 15. Compounds of Formula (24) may be converted to compounds of Formula (27) via reaction with compounds of formula $NH_2NH(C=NH)NH_2$ in the presence or absence of an acid in an inert solvent, followed by reaction with compounds $R^1C(OR_c)_3$ (where $R_c$ is lower alkyl and $R^1$ is defined as above), using the conditions employed for the conversion of compounds of Formulae (3) to (17) to (7) in Scheme 10.

Some compounds of Formula (2) may be prepared by the methods illustrated in Scheme 16.

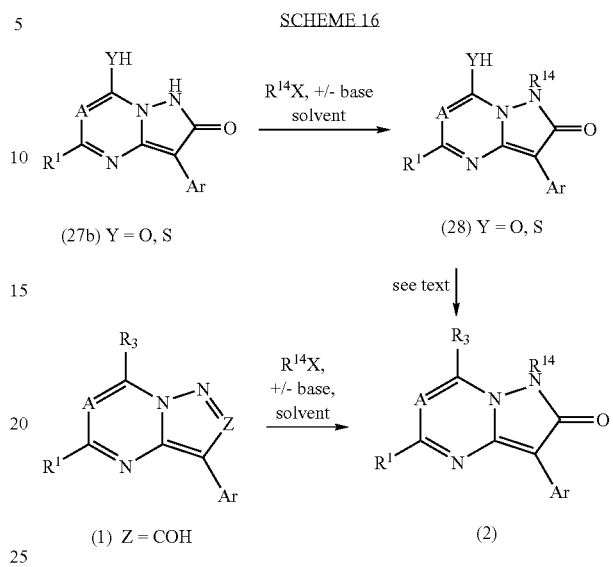

Compounds of Formula (27b) may be treated with various alkylating agents $R^{14}X$ (where $R^{14}$ is defined above and X is halogen, alkanesulfonyloxy or haloalkanesulfonyloxy) in the presence or absence of a base in an inert solvent to afford structures of Formula (28). Compounds of Formula (28) (Y is O) may then be converted to compounds of Formula (2) by treatment with halogenating agents or sulfonylating agents in the presence or absence of a base in an inert solvent, followed by reaction with $R^3H$ in the presence or absence of a base in an inert solvent to give compounds of Formula (2). The reaction conditions used for these conversions are similar to the ones employed for the conversion of intermediate compounds (22) to (23) to (1) in Scheme 14 (for A is CR) or the conversion of intermediate compounds of Formulae (7) to (8) to (1) in Scheme 1 (where A is N). Alternatively, compounds of Formula (28) (Y is S) may be alkylated with a compound $R^fX$ (where $R^f$ is lower alkyl and X is halogen, alkanesulfonyloxy or haloalkanesulfonyloxy) in an inert solvent, (then optionally oxidized with an oxidizing agent in an inert solvent) and then reacted with $R^3H$ in the presence or absence of a base in an inert solvent to give a compound of Formula (1). The conditions and reagents employed are similar to those used in the conversion of intermediate compounds of Formulae (7) to (12) (or to (13)) to compounds of Formula (1) in Scheme 2.

Compounds of Formula (1), where Z is COH, may be converted to compounds of Formula (2) as illustrated in Scheme 16. Treatment with various alkylating agents $R^{14}X$ (where $R^{14}$ is defined above and X is halogen, alkanesulfonyloxy or haloalkanesulfonyloxy) in the presence or absence of a base in an inert solvent to afford structures (2). It will be recognized by one skilled in the art that the methods used in Scheme 16 may also be used to prepare compounds of Formula (1) where Z is $COR^7$.

For Scheme 16, the terms "base" and "inert solvent" may have the meanings given below. Bases may include, but are not limited to, alkali metal hydrides (preferably sodium hydride), alkali metal alkoxides (1 to 6 carbons)(preferably sodium methoxide or sodium ethoxide), alkaline earth metal hydrides, alkali metal dialkylamides (preferably lithium di-isopropylamide), alkali metal bis(trialkylsilyl)amides (preferably sodium bis(trimethylsilyl)amide), trialkyl amines (preferably N,N-di-isopropyl-N-ethyl amine or triethylamine) or aromatic amines (preferably pyridine). Inert solvents may include, but are not limited to, lower alkanenitriles (1 to 6 carbons, preferably acetonitrile), dialkyl ethers (preferably diethyl ether), cyclic ethers (preferably tetrahydrofuran or 1,4-dioxane), N,N-dialkylformamides (preferably dimethylformamide), N,N-dialkylacetamides (preferably dimethylacetamide), cyclic amides (preferably N-methylpyrrolidin-2-one), dialkylsulfoxides (preferably dimethylsulfoxide), aromatic hydrocarbons (preferably benzene or toluene) or haloalkanes of 1 to 10 carbons and 1 to 10 halogens (preferably dichloromethane). Preferred reaction temperatures range from −20° C. to 100° C.

EXAMPLES

Analytical data were recorded for the compounds described below using the following general procedures. Proton NMR spectra were recorded on an IBM-Bruker FT-NMR (300 MHz); chemical shifts were recorded in ppm (δ) from an internal tetramethysilane standard in deuterochloroform or deuterodimethylsulfoxide as specified below. Mass spectra (MS) or high resolution mass spectra (HRMS) were recorded on a Finnegan MAT 8230 spectrometer (using chemi-ionization (CI) with $NH_3$ as the carrier gas or gas chromatography (GC) as specified below) or a Hewlett Packard 5988A model spectrometer. Melting points were recorded on a Buchi Model 510 melting point apparatus and are uncorrected. Boiling points are uncorrected. All pH determinations during workup were made with indicator paper.

Reagents were purchased from commercial sources and, where necessary, purified prior to use according to the general procedures outlined by D. Perrin and W. L. F. Armarego, *Purification of Laboratory Chemicals*, 3rd ed., (New York: Pergamon Press, 1988). Chromatography was performed on silica gel using the solvent systems indicated below. For mixed solvent systems, the volume ratios are given. Otherwise, parts and percentages are by weight.

The following examples are provided to describe the invention in further detail. These examples, which set forth the best mode presently contemplated for carrying out the invention, are intended to illustrate and not to limit the invention.

Example 1

Preparation of 2,7-dimethyl-8-(2,4-dimethylphenyl)[1,5-a]-pyrazolo-[1,3,5]-triazin-4(3H)-one (Formula 7, where Y is O, $R_1$ is $CH_3$, Z is C—$CH_3$, Ar is 2,4-dimethylphenyl)

A.1-Cyano-1-(2,4-dimethylphenyl)propan-2-one

Sodium pellets (9.8 g, 0.43 mol) were added portionwise to a solution of 2,4-dimethylphenylacetonitrile (48 g, 0.33 mol) in ethyl acetate (150 mL) at ambient temperature. The reaction mixture was heated to reflux temperature and stirred for 16 hours. The resulting suspension was cooled to room temperature and filtered. The collected precipitate was washed with copious amounts of ether and then air-dried. The solid was dissolved in water and a 1N HCl solution was added until the pH=5–6. The mixture was extracted with ethyl acetate (3×200 mL); the combined organic layers were dried over $MgSO_4$ and filtered. Solvent was removed in vacuo to afford a white solid (45.7 g, 74% yield): NMR ($CDCl_3$, 300 MHz):; CI-MS: 188 (M+H).

B.5-Amino-4-(2,4-dimethylphenyl)-3-methylpyrazole

A mixture of 1-cyano-1-(2,4-dimethylphenyl)propan-2-one (43.8 g, 0.23 mol), hydrazine-hydrate (22 mL, 0.46 mol), glacial acetic acid (45 mL, 0.78 mol) and toluene (500 mL) were stirred at reflux temperature for 18 hours in an apparatus fitted with a Dean-Stark trap. The reaction mixture was cooled to ambient temperature and solvent was removed in vacuo. The residue was dissolved in 6N HCl and the resulting solution was extracted with ether three times. A concentrated ammonium hydroxide solution was added to the aqueous layer until pH=11. The resulting semi-solution was extracted three times with ethyl acetate. The combined organic layers were dried over $MgSO_4$ and filtered. Solvent was removed in vacuo to give a pale brown viscous oil (34.6 g, 75% yield): NMR ($CDCl_3$, 300 MHz): 7.10 (s, 1H), 7.05 (d, 2H, J=1), 2.37 (s, 3H), 2.10 (s, 3H); CI-MS: 202 (M+H).

C.5-Acetamidino-4-(2,4-dimethylphenyl)-3-methylpyrazole, Acetic Acid Salt

Ethyl acetamidate hydrochloride (60 g, 0.48 mol) was added quickly to a rapidly stirred mixture of potassium carbonate (69.5 g, 0.50 mol), dichloromethane (120 mL) and water (350 mL). The layers were separated and the aqueous layer was extracted with dichloromethane (2×120 mL). The combined organic layers were dried over $MgSO_4$ and filtered. Solvent was removed by simple distillation and the pot residue, a clear pale yellow liquid, (35.0 g) was used without further purification.

Glacial acetic acid (9.7 mL, 0.17 mol) was added to a stirred mixture of 5-amino-4-(2,4-dimethylphenyl)-3-methylpyrazole (34 g, 0.17 mol), ethyl acetamidate (22 g, 0.25 mol) and acetonitrile (500 mL). The resulting reaction mixture was stirred at room temperature for 3 days; at the end of which time, it was concentrated in vacuo to about one-third of its original volume. The resulting suspension was filtered and the collected solid was washed with copious amounts of ether. The white solid was dried in vacuo (31.4 g, 61% yield): NMR (DMSO-$d_6$, 300 MHz): 7.00 (s, 1H), 6.90 (dd, 2H, J=7, 1), 2.28 (s, 3H), 2.08 (s, 3H), 2.00 (s, 3H), 1.90 (s, 3H), 1.81 (s, 3H); CI-MS: 243 (M+H).

D.2,7-dimethyl-8-(2,4-dimethylphenyl)[1,5-a]pyrazolo-[1,3,5]-triazin-4(3H)-one

Sodium pellets (23 g, 1 mol) were added portionwise to ethanol (500 mL) with vigorous stirring. After all the sodium reacted, 5-acetamidino-4-(2,4-dimethylphenyl)-3-methylpyrazole, acetic acid salt (31.2 g, 0.1 mol) and diethyl carbonate (97 mL, 0.8 mol) were added. The resulting reaction mixture was heated to reflux temperature and stirred for 18 hours. The mix was cooled to room temperature and solvent was removed in vacuo. The residue was dissolved in water and a 1N HCl solution was added slowly until pH=5–6. The aqueous layer was extracted with ethyl acetate three times; the combined organic layers were dried over $MgSO_4$ and filtered. Solvent was removed in vacuo to give a pale tan solid (26 g, 98% yield): NMR ($CDCl_3$, 300 MHz): 7.15(s, 1H), 7.09 (s, 2H), 2.45 (s, 3H), 2.39 (s, 3H), 2.30 (s, 3H); CI-MS: 269 (M+H).

Example 2

Preparation of 5-methyl-3-(2,4,6-trimethylphenyl)[1,5-a]-[1,2,3]-triazolo-[1,3,5]-triazin-7(6H)-one (Formula 7, where Y is O, $R_1$ is $CH_3$, Z is N, Ar is 2,4,6-trimethylphenyl)

A. 1-Phenylmethyl-4-(2,4,6-trimethylphenyl)-5-aminotriazole

A mixture of 2,4,6-trimethylbenzyl cyanide (1.0 g, 6.3 mmol), benzyl azide (0.92 g, 6.9 mmol) and potassium t-butoxide (0.78 g, 6.9 mmol) in tetrahydrofuran (10 mL) was stirred at ambient temperature for 2.5 days. The resulting suspension was diluted with water and extracted three times with ethyl acetate. The combined organic layers were dried over $MgSO_4$ and filtered. Solvent was removed in vacuo to give a brown oil. Trituration with ether and filtration afforded a yellow solid (1.12 g, 61% yield): NMR ($CDCl_3$, 300 MHz):7.60–7.30 (m, 5H), 7.30–7.20 (m, 2H), 5.50 (s, 2H), 3.18 (br s, 2H), 2.30 (s, 3H), 2.10 (s, 6H); CI-MS: 293 (M+H).

B. 4-(2,4,6-Trimethylphenyl)-5-aminotriazole

Sodium (500 mg, 22 mmol) was added with stirring to a mixture of liquid ammonia (30 mL) and 1-phenylmethyl-4-(2,4,6-trimethylphenyl)-5-aminotriazole (1.1 g, 3.8 mmol). The reaction mixture was stirred until a dark green color persisted. An ammonium chloride solution (mL) was added and the mixture was stirred while warming to ambient temperature over 16 hours. The residue was treated with a 1M HCl solution and filtered. The aqueous layer was basified with a concentrated ammonium hydroxide solution (pH=9) and then extracted with ethyl acetate three times. The combined organic layers were dried over $MgSO_4$ and filtered. Solvent was removed in vacuo to give a yellow solid (520 mg), which was homogeneous by thin layer chromatography (ethyl acetate):
NMR ($CDCl_3$, 300 MHz): 6.97 (s, 2H), 3.68–3.50 (br.s, 2H), 2.32 (s, 3H), 2.10 (s, 6H); CI-MS: 203 (M+H).

C. 4-(2,4,6-Trimethylphenyl)-5-acetamidinotriazole, Acetic Acid Salt

A mixture of 4-(2,4,6-trimethylphenyl)-5-aminotriazole (400 mg, 1.98 mmol), ethyl acetamidate 261 mg, 3 mmol) and glacial acetic acid (0.1 mL, 1.98 mmol) in acetonitrile (6 mL) was stirred at ambient temperature for 4 hours. The resulting suspension was filtered and the collected solid was washed with copious amounts of ether. Drying in vacuo afforded a white solid (490 mg, 82% yield): NMR (DMSO-$d_6$, 300 MHz):7.90–7.70 (br s, 0.5H), 7.50–7.20 (br. s, 0.5H), 6.90 (s, 2H), 6.90 (s, 2H), 3.50–3.10 (br s, 3H), 2.30–2.20 (br s, 3H), 2.05 (d, 1H, J=7), 1.96 (s, 6H), 1.87 (s, 6H); CI-MS: 244 (M+H).

D. 5-methyl-3-(2,4,6-trimethylphenyl)[1,5-a][1,2,3]-triazolo-[1,3,5]-triazin-7(4H)-one Sodium (368 mg, 16.2 mmol) was added with stirring to ethanol (10 mL) at room temperature. After the sodium had reacted, 4-(2,4,6-trimethylphenyl)-5-acetamidino-triazole, acetic acid salt (490 mg, 1.6 mmol) and diethyl carbonate (1.6 mL, 13 mmol) were added. The reaction mixture was stirred at reflux temperature for 5 hours, then cooled to room temperature. The reaction mixture was diluted with water; a 1N HCl solution was added until pH=5–6 and three extractions with ethyl acetate were performed. The combined organic layers were dried over $MgSO_4$ and filtered. Solvent was removed in vacuo to give a yellow residue. Trituration with ether and filtration afforded a yellow solid (300 mg, 69% yield): NMR ($CDCl_3$, 300 MHz): 6.98 (s, 2H), 2.55 (s, 3H), 2.35 (s, 3H), 2.10 (s, 6H); CI-MS: 270 (M+H).

Example 3

Preparation of 4-(di(carbomethoxy)methyl)-2,7-dimethyl-8-(2,4-dimethylphenyl)[1,5-a]-pyrazolo 1,3,5-triazine (Formula 1, where $R^3$ is $CH(CHCO_2CH_3)_2$, $R_1$ is $CH_3$, Z is C—$CH_3$, Ar is 2,4-dimethylphenyl)

A. 4-chloro-2,7-dimethyl-8-(2,4-dichlorophenyl)[1,5-a]-pyrazolo-triazine

A mixture of 2,7-dimethyl-8-(2,4-dimethylphenyl)[1,5-a]-pyrazolo-1,3,5-triazin-4-one (Example 1, 1.38 g, 4.5 mmol), N,N-dimethylaniline (1 mL, 8 mmol) and phosphorus oxychloride (10 mL) was stirred at reflux temperature for 48 hours. The excess phosphorus oxychloride was removed in vacuo. The residue was poured onto ice-water, stirred briefly and extracted quickly with ethyl acetate three times. The combined organic layers were washed with ice water, then dried over $MgSO_4$ and filtered. Solvent was removed in vacuo to give a brown oil. Flash column chromatography (ethyl acetate:hexanes::1:4) gave one fraction ($R_f$=0.5) Solvent was removed in vacuo to afford a yellow oil (1.0 g, 68% yield): NMR ($CDCl_3$, 300 MHz): 7.55 (d, 1H, J=1), 7.38 (dd, 1H, J=7,1), 7.30 (d, 1H, J=7), 2.68 (s, 3H), 2.45 (s, 3H); CI-MS: 327 (M+H).

B. 4-(di(carbomethoxy)methyl)-2,7-dimethyl-8-(2,4-dimethylphenyl)[1,5-a]-pyrazolo-1,3,5-triazine Sodium hydride (60% in oil, 80 mg, 2 mmol) was washed with hexanes twice, decanted after each washing and taken up in anhydrous tetrahydrofuran (THF, 1 mL). A solution of diethyl malonate (0.32 g, 2 mmol) in THF (2 mL) was added dropwise over 5 min, during which time vigorous gas evolution ensued. A solution of 4-chloro-2,7-dimethyl-8-(2,4-dichlorophenyl)[1,5-a]pyrazolotriazine (0.5 g, 1.75 mmol) in THF (2 mL) was added and the reaction mixture was then stirred under a nitrogen atmosphere for 48 hours. The resulting suspension was poured onto water and extracted three times with ethyl acetate. The combined organic layers were washed once with brine, dried over $MgSO_4$ and filtered. Solvent was removed in vacuo to give a brown oil. Column chromatography (ethyl acetate:hexanes::1:9) afforded, after removal of solvent in vacuo, a pale yellow solid (Rf=0.2, 250 mg, 35% yield): mp 50–52° C.; NMR ($CDCl_3$, 300 MHz): 12.35 (br.s, 1H, 7.15–7.00 (m, 3H), 4.40 (q, 2H, J=7), 4.30 (q, 2H, J=7), 2.4, 2.35, 2.3, 2.2, 2.1 (5 s, 12H), 1.4 (t, 3H, J=7), 1.35–1.25 (m, 3H); CI-HRMS: Calcd: 411.2032, Found: 411.2023.

Example 6

Preparation of 4-(1,3-dimethoxy-2-propylamino)-2,7-dimethyl-8-(2,4-dichlorophenyl)[1,5-a]-pyrazolo 1,3,5-triazine (Formula 1, where $R^3$ is NHCH($CH_2OCH_3$)$_2$, $R_1$ is $CH_3$, Z is C—$CH_3$, Ar is 2,4-dichlorophenyl)

A. 4-chloro-2,7-dimethyl-8-(2,4-dichlorophenyl)[1,5-a]-pyrazolotriazine

A mixture of 2,7-dimethyl-8-(2,4 dimethylphenyl)[1,5-a]-pyrazolo-1,3,5-triazin-4-one (Example 1, 1.38 g, 4.5 mmol), N,N-dimethylaniline (1 mL, 8 mmol) and phosphorus oxychloride (10 mL) was stirred at reflux temperature for 48 hours. The excess phosphorus oxychloride was removed in vacuo. The residue was poured onto ice-water, stirred briefly and extracted quickly with ethyl acetate three times. The combined organic layers were washed with ice water, then dried over $MgSO_4$ and filtered. Solvent was removed in vacuo to give a brown oil. Flash column chromatography (ethyl acetate:hexanes::1:4) gave one fraction (Rf=0.5) Solvent was removed in vacuo to afford a yellow oil (1.0 g, 68% yield): NMR ($CDCl_3$,300 MHz): 7.55 (d, 1H, J=1), 7.38 (dd, 1H, J=7,1), 7.30 (d, 1H, J=7), 2.68 (s, 3H), 2.45 (s, 3H); CI-MS: 327 (M+H).

B. 4-(1,3-dimethoxy-2-propylamino)-2,7-dimethyl-8-(2,4-dichlorophenyl)[1,5-a]-pyrazolo-1,3,5-triazine A mixture of 4-chloro-2,7-dimethyl-8-(2,4-dichlorophenyl)[1,5-a]-pyrazolo-1,3,5-triazine (Part A, 570 mg, 1.74 mmol), 1,3-dimethoxypropyl-2-aminopropane (25 mg, 2.08 mmol) and ethanol (10 mL) was stirred at ambient temperature for 18 hours. The reaction mixture was poured onto water (25 mL) and extracted three times with ethyl acetate. The combined organic layers were dried over $MgSO_4$ and filtered. Solvent was removed in vacuo. Column chromatography ($CH_2Cl_2$:$CH_3OH$::50:1) afforded one fraction. Removal of solvent in vacuo gave a solid (250 mg, 35% yield): mp 118–120° C.; NMR ($CDCl_3$,300 MHz): 7.50 (s, 1H), 7.28 (dd, 2H, J=8,1), 6.75 (d, 1H, J=8), 4.70–4.58 (m, 1H), 3.70–3.55 (m, 4H), 3.43 (s, 6H), 2.50 (s, 3H), 2.35 (s, 3H); CI-HRMS: Calcd: 409.1072, Found: 409.1085; Analysis Calcd. for $C_{18}H_{21}Cl_2N_5O_2$: C, 52.69, H, 5.17, N, 17.07, Cl, 17.28; Found: C, 52.82, H, 5.06, N, 16.77, Cl, 17.50.

Using the above procedures and modifications known to one skilled in the art of organic synthesis, the following additional examples of Tables 1–4 may be prepared.

The examples delineated in TABLE 1 may be prepared by the methods outlined in Examples 1, 2, 3 or 6. Commonly used abbreviations are: Ph is phenyl, Pr is propyl, Me is methyl, Et is ethyl, Bu is butyl, Ex is Example.

TABLE 1

| Ex. | Z | $R_3$ | Ar | mp(° C.) |
|---|---|---|---|---|
| 6[a] | C—Me | $NHCH(CH_2OMe)_2$ | 2,4-$Cl_2$—Ph | 118–120 |
| 7[b] | C—Me | $NHCHPr_2$ | 2,4-$Cl_2$—Ph | 114–116 |
| 8[c] | C—Me | NEtBu | 2,4-$Cl_2$—Ph | oil |
| 9[d] | C—Me | $NPr(CH_2$-c-$C_3H_5)$ | 2,4-$Cl_2$—Ph | oil |
| 10[e] | C—Me | $N(CH_2CH_2OMe)_2$ | 2,4-$Cl_2$—Ph | oil |
| 11[f] | C—Me | NH-3-heptyl | 2,4-$Cl_2$—Ph | 90–92 |
| 12[g] | C—Me | $NHCH(Et)CH_2OMe$ | 2,4-$Cl_2$—Ph | 179–181 |
| 13[h] | C—Me | $NEt_2$ | 2,4-$Cl_2$—Ph | 133–134 |
| 14[i] | C—Me | $NHCH(CH_2OEt)_2$ | 2,4-$Cl_2$—Ph | oil |
| 15[j] | C—Me | NH-3-pentyl | 2,4-$Cl_2$—Ph | 139–140 |
| 16[k] | C—Me | NMePh | 2,4-$Cl_2$—Ph | 60–62 |
| 17[l] | C—Me | $NPr_2$ | 2,4-$Cl_2$—Ph | oil |
| 18[m] | C—Me | NH-3-hexyl | 2,4-$Cl_2$—Ph | 130–132 |
| 19 | C—Me | morpholino | 2,4-$Cl_2$—Ph | |
| 20 | C—Me | $N(CH_2Ph)CH_2CH_2OMe$ | 2,4-$Cl_2$—Ph | |
| 21 | C—Me | $NHCH(CH_2Ph)CH_2OMe$ | 2,4-$Cl_2$—Ph | |
| 22 | C—Me | NH-4-tetrahydropyranyl | 2,4-$Cl_2$—Ph | |
| 23 | C—Me | NH-cyclopentyl | 2,4-$Cl_2$—Ph | |
| 24 | C—Me | 1,2,3,4-tetrahydro-isoquinolinyl | 2,4-$Cl_2$—Ph | |
| 25 | C—Me | $CH_2$-(1,2,3,4-tetrahydro-isoquinolinyl) | 2,4-$Cl_2$—Ph | |
| 26[n] | C—Me | OEt | 2,4-$Cl_2$—Ph | 141–143 |
| 27 | C—Me | $OCH(Et)CH_2OMe$ | 2,4-$Cl_2$—Ph | |
| 28 | C—Me | $OCH_2Ph$ | 2,4-$Cl_2$—Ph | |
| 29 | C—Me | O-3-pentyl | 2,4-$Cl_2$—Ph | |
| 30 | C—Me | SEt | 2,4-$Cl_2$—Ph | |
| 31 | C—Me | S(O)Et | 2,4-$Cl_2$—Ph | |
| 32 | C—Me | $SO_2Et$ | 2,4-$Cl_2$—Ph | |
| 33 | C—Me | $CH(CO_2Et)_2$ | 2,4-$Cl_2$—Ph | |
| 34 | C—Me | $C(Et)(CO_2Et)_2$ | 2,4-$Cl_2$—Ph | |
| 35 | C—Me | $CH(Et)CH_2OH$ | 2,4-$Cl_2$—Ph | |
| 36 | C—Me | $CH(Et)CH_2OMe$ | 2,4-$Cl_2$—Ph | |
| 37 | C—Me | $CONMe_2$ | 2,4-$Cl_2$—Ph | |
| 38 | C—Me | $COCH_3$ | 2,4-$Cl_2$—Ph | |
| 39 | C—Me | $CH(OH)CH_3$ | 2,4-$Cl_2$—Ph | |
| 40 | C—Me | C(OH)Ph-3-pyridyl | 2,4-$Cl_2$—Ph | |
| 41 | C—Me | Ph | 2,4-$Cl_2$—Ph | |
| 42 | C—Me | 2-$CF_3$—Ph | 2,4-$Cl_2$—Ph | |
| 43 | C—Me | 2-Ph—Ph | 2,4-$Cl_2$—Ph | |
| 44 | C—Me | 3-pentyl | 2,4-$Cl_2$—Ph | |
| 45 | C—Me | cyclobutyl | 2,4-$Cl_2$—Ph | |

TABLE 1-continued

[Structure: methyl-substituted triazine fused with triazole bearing R3 and Ar groups, with Z position]

| Ex. | Z | R₃ | Ar | mp(° C.) |
|---|---|---|---|---|
| 46 | C—Me | 3-pyridyl | 2,4-Cl₂—Ph | |
| 47 | C—Me | CH(Et)CH₂CONMe₂ | 2,4-Cl₂—Ph | |
| 48 | C—Me | CH(Et)CH₂CH₂NMe₂ | 2,4-Cl₂—Ph | |
| 49[o] | C—Me | NHCH(CH₂OMe)₂ | 2,4,6-Me₃—Ph | 125–127 |
| 50 | C—Me | NHCHPr₂ | 2,4,6-Me₃—Ph | |
| 51 | C—Me | NEtBu | 2,4,6-Me₃—Ph | |
| 52 | C—Me | NPr(CH₂-c-C₃H₅) | 2,4,6-Me₃—Ph | |
| 53[ae] | C—Me | N(CH₂CH₂OMe)₂ | 2,4,6-Me₃—Ph | 123–124 |
| 54 | C—Me | NH-3-heptyl | 2,4,6-Me₃—Ph | |
| 55[ac] | C—Me | NHCH(Et)CH₂OMe | 2,4,6-Me₃—Ph | 145–146 |
| 56[ah] | C—Me | NEt₂ | 2,4,6-Me₃—Ph | 88–90 |
| 57[ai] | C—Me | NHCH(CH₂OEt)₂ | 2,4,6-Me₃—Ph | 132–134 |
| 58[ad] | C—Me | NH-3-pentyl | 2,4,6-Me₃—Ph | 134–135 |
| 59 | C—Me | NMePh | 2,4,6-Me₃—Ph | |
| 60 | C—Me | NPr₂ | 2,4,6-Me₃—Ph | |
| 61 | C—Me | NH-3-hexyl | 2,4,6-Me₃—Ph | |
| 62 | C—Me | morpholino | 2,4,6-Me₃—Ph | |
| 63 | C—Me | N(CH₂Ph)CH₂CH₂OMe | 2,4,6-Me₃—Ph | |
| 64 | C—Me | NHCH(CH₂Ph)CH₂OMe | 2,4,6-Me₃—Ph | |
| 65 | C—Me | NH-4-tetrahydropyranyl | 2,4,6-Me₃—Ph | |
| 66 | C—Me | NH-cyclopentyl | 2,4,6-Me₃—Ph | |
| 67 | C—Me | 1,2,3,4-tetrahydro-isoquinolinyl | 2,4,6-Me₃—Ph | |
| 68 | C—Me | CH₂-(1,2,3,4-tetrahydro-isoquinolinyl) | 2,4,6-Me₃—Ph | |
| 69 | C—Me | OEt | 2,4,6-Me₃—Ph | |
| 70 | C—Me | OCH(Et)CH₂OMe | 2,4,6-Me₃—Ph | |
| 71 | C—Me | OCH₂Ph | 2,4,6-Me₃—Ph | |
| 72 | C—Me | O-3-pentyl | 2,4,6-Me₃—Ph | |
| 73 | C—Me | SEt | 2,4,6-Me₃—Ph | |
| 74 | C—Me | S(O)Et | 2,4,6-Me₃—Ph | |
| 75 | C—Me | SO₂Et | 2,4,6-Me₃—Ph | |
| 76 | C—Me | CH(CO₂Et)2 | 2,4,6-Me₃—Ph | |
| 77 | C—Me | C(Et)(CO₂Et)₂ | 2,4,6-Me₃—Ph | |
| 78 | C—Me | CH(Et)CH₂OH | 2,4,6-Me₃—Ph | |
| 79 | C—Me | CH(Et)CH₂OMe | 2,4,6-Me₃—Ph | |
| 80 | C—Me | CONMe₂ | 2,4,6-Me₃—Ph | |
| 81 | C—Me | COCH₃ | 2,4,6-Me₃—Ph | |
| 82 | C—Me | CH(OH)CH₃ | 2,4,6-Me₃—Ph | |
| 83 | C—Me | C(OH)Ph-3-pyridyl | 2,4,6-Me₃—Ph | |
| 84 | C—Me | Ph | 2,4,6-Me₃—Ph | |
| 85 | C—Me | 2-CF₃—Ph | 2,4,6-Me₃—Ph | |
| 86 | C—Me | 2-Ph-Ph | 2,4,6-Me₃—Ph | |
| 87 | C—Me | 3-pentyl | 2,4,6-Me₃—Ph | |
| 88 | C—Me | cyclobutyl | 2,4,6-Me₃—Ph | |
| 89 | C—Me | 3-pyridyl | 2,4,6-Me₃—Ph | |
| 90 | C—Me | CH(Et)CH₂CONMe₂ | 2,4,6-Me₃—Ph | |
| 91 | C—Me | CH(Et)CH₂CH₂NMe₂ | 2,4,6-Me₃—Ph | |
| 92[p] | C—Me | NHCH(CH₂OMe)₂ | 2,4-Me₂—Ph | 44–45 |
| 93[q] | C—Me | N(CH₂CH₂OMe)₂ | 2,4-Me₂—Ph | oil |
| 94[r] | C—Me | NHCH(Et)CH₂OMe | 2,4-Me₂—Ph | 102–104 |
| 95[s] | C—Me | NH-3-pentyl | 2,4-Me₂—Ph | 102–104 |
| 96[t] | C—Me | NEt₂ | 2,4-Me₂—Ph | oil |
| 97[u] | C—Me | N(CH₂CN)₂ | 2,4-Me₂—Ph | 148–150 |
| 98[v] | C—Me | NHCH(Me)CH₂OMe | 2,4-Me₂—Ph | 102–104 |
| 99[w] | C—Me | OCH(Et)CH₂OMe | 2,4-Me₂—Ph | oil |
| 100[x] | C—Me | NPr-c-C₃H₅ | 2,4-Me₂—Ph | oil |
| 101[y] | C—Me | NHCH(Me)CH₂NMe₂ | 2,4-Me₂—Ph | 47–48 |
| 202[z] | C—Me | N(c-C₃H₅)CH₂CH₂CN | 2,4-Me₂—Ph | 117–118 |
| 103[aa] | C—Me | N(Pr)CH₂CH₂CN | 2,4-Me₂—Ph | oil |
| 104[ab] | C—Me | N(Bu)CH₂CH₂CN | 2,4-Me₂—Ph | oil |
| 105 | C—Me | NHCHPr₂ | 2,4-Me₂—Ph | |
| 106 | C—Me | NEtBu | 2,4-Me₂—Ph | |
| 107 | C—Me | NPr(CH₂-c-C₃H₅) | 2,4-Me₂—Ph | |
| 108 | C—Me | NH-3-heptyl | 2,4-Me₂—Ph | |
| 109 | C—Me | NEt₂ | 2,4-Me₂—Ph | |
| 110 | C—Me | NHCH(CH₂OEt)₂ | 2,4-Me₂—Ph | |
| 111 | C—Me | NH-3-pentyl | 2,4-Me₂—Ph | |

TABLE 1-continued

[Structure: pyrazolo-triazine core with R3, Z, and Ar substituents]

| Ex. | Z | R₃ | Ar | mp(° C.) |
|---|---|---|---|---|
| 112 | C—Me | NMePh | 2,4-Me₂—Ph | |
| 113 | C—Me | NPr₂ | 2,4-Me₂—Ph | |
| 114 | C—Me | NH-3-hexyl | 2,4-Me₂—Ph | |
| 115 | C—Me | morpholino | 2,4-Me₂—Ph | |
| 116 | C—Me | N(CH₂Ph)CH₂CH₂OMe | 2,4-Me₂—Ph | |
| 117 | C—Me | NHCH(CH₂Ph)CH₂OMe | 2,4-Me₂—Ph | |
| 118 | C—Me | NH-4-tetrahydropyranyl | 2,4-Me₂—Ph | |
| 119 | C—Me | NH-cyclopentyl | 2,4-Me₂—Ph | |
| 120 | C—Me | 1,2,3,4-tetrahydro-isoquinolinyl | 2,4-Me₂—Ph | |
| 121 | C—Me | CH₂-(1,2,3,4-tetrahydro-isoquinolinyl) | 2,4-Me₂—Ph | |
| 122 | C—Me | OEt | 2,4-Me₂—Ph | |
| 123 | C—Me | OCH(Et)CH₂OMe | 2,4-Me₂—Ph | |
| 124 | C—Me | OCH₂Ph | 2,4-Me₂—Ph | |
| 125 | C—Me | O-3-pentyl | 2,4-Me₂—Ph | |
| 126 | C—Me | SEt | 2,4-Me₂—Ph | |
| 127 | C—Me | S(O)Et | 2,4-Me₂—Ph | |
| 128 | C—Me | SO₂Et | 2,4-Me₂—Ph | |
| 3 | C—Me | CH(CO₂Et)₂ | 2,4-Me₂—Ph | 50–52 |
| 129 | C—Me | C(Et)(CO₂Et)₂ | 2,4-Me₂—Ph | |
| 130 | C—Me | CH(Et)CH₂OH | 2,4-Me₂—Ph | |
| 131 | C—Me | CH(Et)CH₂OMe | 2,4-Me₂—Ph | |
| 132 | C—Me | CH(Et)CH₂OEt | 2,4-Me₂—Ph | |
| 133 | C—Me | CONMe₂ | 2,4-Me₂—Ph | |
| 134 | C—Me | COCH₃ | 2,4-Me₂—Ph | |
| 135 | C—Me | CH(OH)CH₃ | 2,4-Me₂—Ph | |
| 136 | C—Me | C(OH)Ph-3-pyridyl | 2,4-Me₂—Ph | |
| 137 | C—Me | Ph | 2,4-Me₂—Ph | |
| 138 | C—Me | 2-CF₃—Ph | 2,4-Me₂—Ph | |
| 139 | C—Me | 2-Ph—Ph | 2,4-Me₂—Ph | |
| 140 | C—Me | 3-pentyl | 2,4-Me₂—Ph | |
| 141 | C—Me | cyclobutyl | 2,4-Me₂—Ph | |
| 142 | C—Me | 3-pyridyl | 2,4-Me₂—Ph | |
| 143 | C—Me | CH(Et)CH₂CONMe₂ | 2,4-Me₂—Ph | |
| 144 | C—Me | CH(Et)CH₂CH₂NMe₂ | 2,4-Me₂—Ph | |
| 145[bc] | C—Me | NHCH(CH₂OMe)₂ | 2-Me-4-MeO—Ph | 45–46 |
| 146[bd] | C—Me | N(CH₂CH₂OMe)₂ | 2-Me-4-MeO—Ph | oil |
| 147[be] | C—Me | NHCH(Et)CH₂OMe | 2-Me-4-MeO—Ph | 86–88 |
| 148[bf] | C—Me | N(Pr)CH₂CH₂CN | 2-Me-4-MeO—Ph | oil |
| 149 | C—Me | OCH(Et)CH₂OMe | 2-Me-4-MeO—Ph | |
| 150[af] | C—Me | NHCH(CH₂OMe)₂ | 2-Br-4-MeO—Ph | 88–90 |
| 151[al] | C—Me | N(CH₂CH₂OMe)₂ | 2-Br-4-MeO—Ph | oil |
| 152[ag] | C—Me | NHCH(Et)CH₂OMe | 2-Br-4-MeO—Ph | 95–97 |
| 153 | C—Me | N(Pr)CH₂CH₂CN | 2-Br-4-MeO—Ph | |
| 154 | C—Me | OCH(Et)CH₂OMe | 2-Br-4-MeO—Ph | |
| 155 | C—Me | NHCH(CH₂OMe)₂ | 2-Me-4-NMe₂—Ph | |
| 156 | C—Me | N(CH₂CH₂OMe)₂ | 2-Me-4-NMe₂—Ph | oil |
| 157 | C—Me | NHCH(Et)CH₂OMe | 2-Me-4-NMe₂—Ph | |
| 158 | C—Me | N(Pr)CH₂CH₂CN | 2-Me-4-NMe₂—Ph | |
| 159 | C—Me | OCH(Et)CH₂OMe | 2-Me-4-NMe₂—Ph | |
| 160 | C—Me | NHCH(CH₂OMe)₂ | 2-Br-4-NMe₂—Ph | |
| 161 | C—Me | N(CH₂CH₂OMe)₂ | 2-Br-4-NMe₂—Ph | |
| 162 | C—Me | NHCH(Et)CH₂OMe | 2-Br-4-NMe₂—Ph | |
| 163 | C—Me | N(Pr)CH₂CH₂CN | 2-Br-4-NMe₂—Ph | |
| 164 | C—Me | OCH(Et)CH₂OMe | 2-Br-4-NMe₂—Ph | |
| 165 | C—Me | NHCH(CH₂OMe)₂ | 2-Br-4-i-Pr—Ph | |
| 166 | C—Me | N(CH₂CH₂OMe)₂ | 2-Br-4-i-Pr—Ph | |
| 167 | C—Me | NHCH(Et)CH₂OMe | 2-Br-4-i-Pr—Ph | |
| 168 | C—Me | N(Pr)CH₂CH₂CN | 2-Br-4-i-Pr—Ph | |
| 169 | C—Me | OCH(Et)CH₂OMe | 2-Br-4-i-Pr—Ph | |
| 170 | C—Me | NHCH(CH₂OMe)₂ | 2-Br-4-Me—Ph | |
| 171 | C—Me | N(CH₂CH₂OMe)₂ | 2-Br-4-Me—Ph | |
| 172 | C—Me | NHCH(Et)CH₂OMe | 2-Br-4-Me—Ph | |
| 173 | C—Me | N(Pr)CH₂CH₂CN | 2-Br-4-Me—Ph | |
| 174 | C—Me | OCH(Et)CH₂OMe | 2-Br-4-Me—Ph | |
| 175[ar] | C—Me | NHCH(CH₂OMe)₂ | 2-Me-4-Br—Ph | 108–109 |
| 176 | C—Me | N(CH₂CH₂OMe)₂ | 2-Me-4-Br—Ph | |

TABLE 1-continued

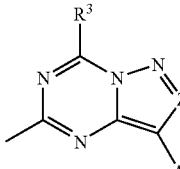

| Ex. | Z | R₃ | Ar | mp(° C.) |
|---|---|---|---|---|
| 177 | C—Me | NHCH(Et)CH₂OMe | 2-Me-4-Br—Ph | |
| 178 | C—Me | N(Pr)CH₂CH₂CN | 2-Me-4-Br—Ph | |
| 179 | C—Me | OCH(Et)CH₂OMe | 2-Me-4-Br—Ph | |
| 180 | C—Me | NHCH(CH₂OMe)₂ | 2-Cl-4,6-Me₂—Ph | |
| 181 | C—Me | N(CH₂CH₂OMe)₂ | 2-Cl-4,6-Me₂—Ph | |
| 182 | C—Me | NHCH(CH₂OMe)₂ | 4-Br-2,6-(Me)₂—Ph | |
| 183 | C—Me | N(CH₂CH₂OMe)₂ | 4-Br-2,6-(Me)₂—Ph | |
| 184 | C—Me | NHCH(CH₂OMe)₂ | 4-i-Pr-2-SMe—Ph | |
| 185 | C—Me | N(CH₂CH₂OMe)₂ | 4-i-Pr-2-SMe—Ph | |
| 186 | C—Me | NHCH(CH₂OMe)₂ | 2-Br-4-CF₃—Ph | |
| 187 | C—Me | N(CH₂CH₂OMe)₂ | 2-Br-4-CF₃—Ph | |
| 188 | C—Me | NHCH(CH₂OMe)₂ | 2-Br-4,6-(MeO)₂—Ph | |
| 189 | C—Me | N(CH₂CH₂OMe)₂ | 2-Br-4,6-(MeO)₂—Ph | |
| 190 | C—Me | NHCH(CH₂OMe)₂ | 2-Cl-4,6-(MeO)₂—Ph | |
| 191 | C—Me | N(CH₂CH₂OMe)₂ | 2-Cl-4,6-(MeO)₂—Ph | |
| 192 | C—Me | NHCH(CH₂OMe)₂ | 2,6-(Me)₂-4-SMe—Ph | |
| 193 | C—Me | N(CH₂CH₂OMe)₂ | 2,6-(Me)₂-4-SMe—Ph | |
| 194 | C—Me | NHCH(CH₂OMe)₂ | 4-(COMe)-2-Br—Ph | |
| 195 | C—Me | N(CH₂CH₂OMe)₂ | 4-(COMe)-2-Br—Ph | |
| 196 | C—Me | NHCH(CH₂OMe)₂ | 2,4,6-Me₃-pyrid-3-yl | |
| 197 | C—Me | N(CH₂CH₂OMe)₂ | 2,4,6-Me₃-pyrid-3-yl | |
| 198 | C—Me | NHCH(CH₂OMe)₂ | 2,4-(Br)₂—Ph | |
| 199 | C—Me | N(CH₂CH₂OMe)₂ | 2,4-(Br)₂—Ph | |
| 200 | C—Me | NHCH(CH₂OMe)₂ | 4-i-Pr-2-SMe—Ph | |
| 201 | C—Me | N(CH₂CH₂OMe)₂ | 4-i-Pr-2-SMe—Ph | |
| 202 | C—Me | NHCH(CH₂OMe)₂ | 4-i-Pr-2-SO₂Me—Ph | |
| 203 | C—Me | N(CH₂CH₂OMe)₂ | 4-i-Pr-2-SO₂Me—Ph | |
| 204 | C—Me | NHCH(CH₂OMe)₂ | 2,6-(Me)₂-4-SMe—Ph | |
| 205 | C—Me | N(CH₂CH₂OMe)₂ | 2,6-(Me)₂-4-SMe—Ph | |
| 206 | C—Me | NHCH(CH₂OMe)₂ | 2,6-(Me)₂-4-SO₂Me—Ph | |
| 207 | C—Me | N(CH₂CH₂OMe)₂ | 2,6-(Me)₂-4-SO₂Me—Ph | |
| 208 | C—Me | NHCH(CH₂OMe)₂ | 2-I-4-i-Pr—Ph | |
| 209 | C—Me | N(CH₂CH₂OMe)₂ | 2-I-4-i-Pr—Ph | |
| 210 | C—Me | NHCH(CH₂OMe)₂ | 2-Br-4-N(Me)₂-6-MeO—Ph | |
| 211 | C—Me | N(CH₂CH₂OMe)₂ | 2-Br-4-N(Me)₂-6-MeO—Ph | |
| 212 | C—Me | NHCH(CH₂OMe)₂ | 2,4-[SMe]2-Ph | |
| 213 | C—Me | N(CH₂CH₂OMe)₂ | 2,4-[SMe]2-Ph | |
| 214 | C—Me | NHCH(CH₂OMe)₂ | 2,4-[SO₂Me]2-Ph | |
| 215 | C—Me | N(CH₂CH₂OMe)₂ | 2,4-[SO₂Me 2-Ph | |
| 216 | C—Me | NHCH(CH₂OMe)₂ | 4-i-Pr-2-SMe—Ph | |
| 217 | C—Me | N(CH₂CH₂OMe)₂ | 4-i-Pr-2-SMe—Ph | |
| 218 | C—Me | NHCH(CH₂OMe)₂ | 4-i-Pr-2-SO₂Me—Ph | |
| 219 | C—Me | N(CH₂CH₂OMe)₂ | 4-i-Pr-2-SO₂Me—Ph | |
| 220 | C—Me | NHCH(CH₂OMe)₂ | 2-N(Me)₂-4-Me—Ph | |
| 221 | C—Me | N(CH₂CH₂OMe)₂ | 2-N(Me)₂-4-Me—Ph | |
| 222 | C—Me | NHCH(CH₂OMe)₂ | 2-MeS-4,6-(Me)₂—Ph | |
| 223 | C—Me | N(CH₂CH₂OMe)₂ | 2-MeS-4,6-(Me)₂—Ph | |
| 224 | C—Me | NHCH(CH₂OMe)₂ | 2-(CH₃CO)-4,6-(Me)₂—Ph | |
| 225 | C—Me | N(CH₂CH₂OMe)₂ | 2-(CH₃CO)-4,6-(Me)₂—Ph | |
| 226 | H | NHCH(CH₂OMe)₂ | 2,4-Me₂—Ph | |
| 227 | H | NHCH(CH₂OMe)₂ | 2,4-Me₂—Ph | |
| 228 | CF3 | N(CH₂CH₂OMe)₂ | 2,4-Me₂—Ph | |
| 229 | CF3 | N(CH₂CH₂OMe)₂ | 2,4-Me₂—Ph | |
| 230 | N | NHCH(CH₂OMe)₂ | 2,4,6-Me₃—Ph | |
| 231 | N | NHCHPr₂ | 2,4,6-Me₃—Ph | |
| 232 | N | NEtBu | 2,4,6-Me₃—Ph | |
| 233 | N | NPr(CH₂-c-C₃H₅) | 2,4,6-Me₃—Ph | |
| 234 | N | N(CH₂CH₂OMe)₂ | 2,4,6-Me₃—Ph | |
| 235 | N | NH-3-heptyl | 2,4,6-Me₃—Ph | |
| 236 | N | NHCH(Et)CH₂OMe | 2,4,6-Me₃—Ph | |
| 237 | N | NEt₂ | 2,4,6-Me₃—Ph | |
| 238 | N | NHCH(CH₂OEt)₂ | 2,4,6-Me₃—Ph | |
| 239 | N | NH-3-pentyl | 2,4,6-Me₃—Ph | |
| 240 | N | NMePh | 2,4,6-Me₃—Ph | |
| 241 | N | NPr₂ | 2,4,6-Me₃—Ph | |
| 242 | N | NH-3-hexyl | 2,4,6-Me₃—Ph | |
| 243 | N | morpholino | 2,4,6-Me₃—Ph | |
| 244 | N | N(CH₂Ph)CH₂CH₂OMe | 2,4,6-Me₃—Ph | |

TABLE 1-continued

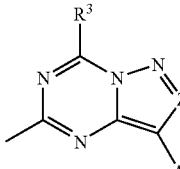

| Ex. | Z | R₃ | Ar | mp(° C.) |
|---|---|---|---|---|
| 245 | N | NHCH(CH₂Ph)CH₂OMe | 2,4,6-Me₃—Ph | |
| 246 | N | NH-4-tetrahydropyranyl | 2,4,6-Me₃—Ph | |
| 247 | N | NH-cyclopentyl | 2,4,6-Me₃—Ph | |
| 248 | N | 1,2,3,4-tetrahydro-isoquinolinyl | 2,4,6-Me₃—Ph | |
| 249 | N | CH₂-(1,2,3,4-tetrahydro-isoquinolinyl) | 2,4,6-Me₃—Ph | |
| 250 | N | OEt | 2,4,6-Me₃—Ph | |
| 251 | N | OCH(Et)CH₂OMe | 2,4,6-Me₃—Ph | |
| 252 | N | OCH₂Ph | 2,4,6-Me₃—Ph | |
| 253 | N | O-3-pentyl | 2,4,6-Me₃—Ph | |
| 254 | N | SEt | 2,4,6-Me₃—Ph | |
| 255 | N | S(O)Et | 2,4,6-Me₃—Ph | |
| 256 | N | SO₂Et | 2,4,6-Me₃—Ph | |
| 257 | N | CH(CO₂Et)₂ | 2,4,6-Me₃—Ph | |
| 258 | N | C(Et)(CO₂Et)₂ | 2,4,6-Me₃—Ph | |
| 259 | N | CH(Et)CH₂OH | 2,4,6-Me₃—Ph | |
| 260 | N | CH(Et)CH₂OMe | 2,4,6-Me₃—Ph | |
| 261 | N | CONMe₂ | 2,4,6-Me₃—Ph | |
| 262 | N | COCH₃ | 2,4,6-Me₃—Ph | |
| 263 | N | CH(OH)CH₃ | 2,4,6-Me₃—Ph | |
| 264 | N | C(OH)Ph-3-pyridyl | 2,4,6-Me₃—Ph | |
| 265 | N | Ph | 2,4,6-Me₃—Ph | |
| 266 | N | 2-CF₃—Ph | 2,4,6-Me₃—Ph | |
| 267 | N | 2-Ph—Ph | 2,4,6-Me₃—Ph | |
| 268 | N | 3-pentyl | 2,4,6-Me₃—Ph | |
| 269 | N | cyclobutyl | 2,4,6-Me₃—Ph | |
| 270 | N | 3-pyridyl | 2,4,6-Me₃—Ph | |
| 271 | N | CH(Et)CH₂CONMe₂ | 2,4,6-Me₃—Ph | |
| 272 | N | CH(Et)CH₂CH₂NMe₂ | 2,4,6-Me₃—Ph | |
| 273 | N | NHCH(CH₂OMe)₂ | 2,4-Me₂—Ph | |
| 274 | N | NHCHPr₂ | 2,4-Me₂—Ph | |
| 275 | N | NEtBu | 2,4-Me₂—Ph | |
| 276 | N | NPr(CH₂-c-C₃H₅) | 2,4-Me₂—Ph | |
| 277 | N | N(CH₂CH₂OMe)₂ | 2,4-Me₂—Ph | |
| 278 | N | NH-3-heptyl | 2,4-Me₂—Ph | |
| 279 | N | NHCH(Et)CH₂OMe | 2,4-Me₂—Ph | |
| 280 | N | NEt₂ | 2,4-Me₂—Ph | |
| 281 | N | NHCH(CH₂OEt)₂ | 2,4-Me₂—Ph | |
| 282 | N | NH-3-pentyl | 2,4-Me₂—Ph | |
| 283 | N | NMePh | 2,4-Me₂—Ph | |
| 284 | N | NPr₂ | 2,4-Me₂—Ph | |
| 285 | N | NH-3-hexyl | 2,4-Me₂—Ph | |
| 286 | N | morpholino | 2,4-Me₂—Ph | |
| 287 | N | N(CH₂Ph)CH₂CH₂OMe | 2,4-Me₂—Ph | |
| 288 | N | NHCH(CH₂Ph)CH₂OMe | 2,4-Me₂—Ph | |
| 289 | N | NH-4-tetrahydropyranyl | 2,4-Me₂—Ph | |
| 290 | N | NH-cyclopentyl | 2,4-Me₂—Ph | |
| 291 | N | 1,2,3,4-tetrahydro-isoquinolinyl | 2,4-Me₂—Ph | |
| 292 | N | CH₂-(1,2,3,4-tetrahydro-isoquinolinyl) | 2,4-Me₂—Ph | |
| 293 | N | OEt | 2,4-Me₂—Ph | |
| 294 | N | OCH(Et)CH₂OMe | 2,4-Me₂—Ph | |
| 295 | N | OCH₂Ph | 2,4-Me₂—Ph | |
| 296 | N | O-3-pentyl | 2,4-Me₂—Ph | |
| 297 | N | SEt | 2,4-Me₂—Ph | |
| 298 | N | S(O)Et | 2,4-Me₂—Ph | |
| 299 | N | SO₂Et | 2,4-Me₂—Ph | |
| 300 | N | CH(CO₂Et)₂ | 2,4-Me₂—Ph | |
| 301 | N | C(Et)(CO₂Et)₂ | 2,4-Me₂—Ph | |
| 302 | N | CH(Et)CH₂OH | 2,4-Me₂—Ph | |
| 303 | N | CH(Et)CH₂OMe | 2,4-Me₂—Ph | |
| 304 | N | CONMe₂ | 2,4-Me₂—Ph | |
| 305 | N | COCH₃ | 2,4-Me₂—Ph | |
| 306 | N | CH(OH)CH₃ | 2,4-Me₂—Ph | |
| 307 | N | C(OH)Ph-3-pyridyl | 2,4-Me₂—Ph | |
| 308 | N | Ph | 2,4-Me₂—Ph | |

TABLE 1-continued

| Ex. | Z | R₃ | Ar | mp(° C.) |
|---|---|---|---|---|
| 309 | N | 2-CF₃—Ph | 2,4-Me₂—Ph | |
| 310 | N | 2-Ph—Ph | 2,4-Me₂—Ph | |
| 311 | N | 3-pentyl | 2,4-Me₂—Ph | |
| 312 | N | cyclobutyl | 2,4-Me₂—Ph | |
| 313 | N | 3-pyridyl | 2,4-Me₂—Ph | |
| 314 | N | CH(Et)CH₂CONMe₂ | 2,4-Me₂—Ph | |
| 315 | N | CH(Et)CH₂CH₂NMe₂ | 2,4-Me₂—Ph | |
| 316[an] | C—Me | NEt₂ | 2-Br-4-MeO—Ph | oil |
| 317[am] | C—Me | NH-3-pentyl | 2-Br-4-MeO—Ph | oil |
| 318[aj] | C—Me | NHCH(CH₂CH₂OMe)CH₂OMe | 2,4,6-Me₃—Ph | 101–103 |
| 319[ao] | C—Me | NH(c-C₃H₅) | 2,4-Me₂—Ph | oil |
| 320[ak] | C—Me | morpholino | 2,4,6-Me₃—Ph | 139–141 |
| 321[ap] | C—Me | NHCH(CH₂OMe)₂ | 2-CN-4-Me—Ph | 152–153 |
| 322[aq] | C—Me | N(c-C₃H₅)CH₂CH₂CN | 2,4,6-Me₃—Ph | 149–151 |
| 324[as] | C—Me | NHCH(CH₂CH₂OMe)CH₂OMe | 2-Me-4-Br—Ph | 115–117 |
| 325[at] | C—Me | NHCH(CH₂OMe)₂ | 2,5-Me₂-4-MeO—Ph | 55–57 |
| 326[au] | C—Me | N(CH₂CH₂OMe)₂ | 2,5-Me₂-4-MeO—Ph | 72 |
| 327[av] | C—Me | NH-3-pentyl | 2,5-Me₂-4-MeO—Ph | 45–47 |
| 328[aw] | C—Me | NEt₂ | 2,5-Me₂-4-MeO—Ph | oil |
| 329[ax] | C—Me | NHCH(CH₂OMe)₂ | 2-Cl-4-MePh | 80–81 |
| 330[ay] | C—Me | NCH(Et)CH₂OMe | 2-Cl-4-MePh | 77–79 |
| 331[az] | C—Me | N(CH₂CH₂OMe)₂ | 2-Cl-4-MePh | oil |
| 332[ba] | C—Me | (S)-NHCH(CH₂CH₂OMe)CH₂OMe | 2-Cl-4-MePh | 139–140 |
| 333[bb] | C—Me | N(c-C₃H₅)CH₂CH₂CN | 2,5-Me₂-4-MeOPh | 120–122 |
| 334[bg] | C—Me | NEt₂ | 2-Me-4-MeOPh | oil |
| 335[bh] | C—Me | OEt | 2-Me-4-MeOPh | oil |
| 336[bi] | C—Me | (S)-NHCH(CH₂CH₂OMe)CH₂OMe | 2-Me-4-MeOPh | oil |
| 337[bj] | C—Me | N(c-C₃H₅)CH₂CH₂CN | 2-Me-4-MeOPh | 129 |
| 338[bk] | C—Me | NHCH(CH₂OEt)₂ | 2-Me-4-MeOPh | amorph. |
| 339 | C—Me | N(c-C₃H₅)CH₂CH₂CN | 2,4-Cl₂—Ph | 109–110 |
| 340 | C—Me | (S)-NHCH(CH₂CH₂OMe)CH₂OMe | 2,4-Cl₂—Ph | 93–94 |
| 341 | C—Me | NH-3-pentyl | 2-Me-4-BrPh | 118–119 |
| 342 | C—Me | N(CH₂CH₂OMe)₂ | 2-Me-4-BrPh | oil |
| 343 | C—Me | NHCH(CH₂-iPr)CH₂OMe | 2,4-Me₂—Ph | oil |
| 344 | C—Me | NHCH(Pr)CH₂OMe | 2,4-Me₂—Ph | 94–95 |
| 345 | C—Me | NHCH(Et)CH₂OEt | 2,4-Me₂—Ph | 76–77 |
| 346 | C—Me | NHCH(CH₂OMe)CH₂CH₂OMe | 2-Me-4-Me₂NPh | oil |
| 347 | C—Me | NEt₂ | 2-Me-4-ClPh | oil |
| 348 | C—Me | NH-3-pentyl | 2-Me-4-ClPh | 122–124 |
| 349 | C—Me | N(CH₂CH₂OMe)₂ | 2-Me-4-ClPh | oil |
| 350 | C—Me | NHCH(CH₂OMe)₂ | 2-Me-4-ClPh | 122–123 |
| 351 | C—Me | NEt₂ | 2-Me-4-ClPh | oil |
| 352 | C—Me | NEt₂ | 2-Cl-4-MePh | oil |
| 353 | C—Me | NH-3-pentyl | 2-Cl-4-MePh | 120–121 |
| 354 | C—Me | NHCH(CH₂OMe)₂ | 2-Cl-4-MeOPh | |
| 355[bl] | C—Me | N(CH₂CH₂OMe)₂ | 2-Cl-4-MeOPh | oil |
| 356[bm] | C—Me | NHCH(Et)CH₂OMe | 2-Cl-4-MeOPh | 108–110 |
| 357[bn] | C—Me | N(c-Pr)CH₂CH₂CN | 2-Cl-4-MeOPh | 127–129 |
| 358[bo] | C—Me | NEt₂ | 2-Cl-4-MeOPh | oil |
| 359[bp] | C—Me | NH-3-pentyl | 2-Cl-4-MeOPh | 77–79 |
| 360 | C—Me | NHCH(Et)CH₂CH₂OMe | 2-Cl-4-MeOPh | |
| 361 | C—Me | NHCH(Me)CH₂CH₂OMe | 2-Cl-4-MeOPh | |
| 362 | C—Me | NHCH(Et)CH₂CH₂OMe | 2-Br-4-MeOPh | |
| 363 | C—Me | NHCH(Me)CH₂CH₂OMe | 2-Br-4-MeOPh | |
| 364 | C—Me | NHCH(Et)CH₂CH₂OMe | 2-Me-4-MeOPh | |
| 365 | C—Me | NHCH(Me)CH₂CH₂OMe | 2-Me-4-MeOPh | |
| 366 | C—Me | NHCH(CH₂OMe)₂ | 2-Cl-4,5-(MeO)₂Ph | |
| 367 | C—Me | N(CH₂CH₂OMe)₂ | 2-Cl-4,5-(MeO)₂Ph | |
| 368 | C—Me | NHCH(Et)CH₂OMe | 2-Cl-4,5-(MeO)₂Ph | |
| 369 | C—Me | N(c-Pr)CH₂CH₂CN | 2-Cl-4,5-(MeO)₂Ph | |
| 370 | C—Me | NEt₂ | 2-Cl-4,5-(MeO)₂Ph | |
| 371 | C—Me | NH-3-pentyl | 2-Cl-4,5-(MeO)₂Ph | |
| 372 | C—Me | NHCH(Et)CH₂CH₂OMe | 2-Cl-4,5-(MeO)₂Ph | |
| 373 | C—Me | NHCH(Me)CH₂CH₂OMe | 2-Cl-4,5-(MeO)₂Ph | |
| 374[bq] | C—Me | NHCH(CH₂OMe)₂ | 2-Br-4,5-(MeO)₂Ph | 137–138 |
| 375 | C—Me | N(CH₂CH₂OMe)₂ | 2-Br-4,5-(MeO)₂Ph | |
| 376[br] | C—Me | NHCH(Et)CH₂OMe | 2-Br-4,5-(MeO)₂Ph | 147–148 |
| 377 | C—Me | N(c-Pr)CH₂CH₂CN | 2-Br-4,5-(MeO)₂Ph | |

TABLE 1-continued

| Ex. | Z | R₃ | Ar | mp(° C.) |
|---|---|---|---|---|
| 378[bs] | C—Me | NEt₂ | 2-Br-4,5-(MeO)₂Ph | 52–58 |
| 379 | C—Me | NH-3-pentyl | 2-Br-4,5-(MeO)₂Ph | |
| 380 | C—Me | NHCH(Et)CH₂CH₂OMe | 2-Br-4,5-(MeO)₂Ph | |
| 381 | C—Me | NHCH(Me)CH₂CH₂OMe | 2-Br-4,5-(MeO)₂Ph | |
| 382 | C—Me | NHCH(CH₂OMe)₂ | 2-Cl-4,6-(MeO)₂Ph | |
| 383 | C—Me | N(CH₂CH₂OMe)₂ | 2-Cl-4,6-(MeO)₂Ph | |
| 384 | C—Me | NHCH(Et)CH₂OMe | 2-Cl-4,6-(MeO)₂Ph | |
| 385 | C—Me | N(c-Pr)CH₂CH₂CN | 2-Cl-4,6-(MeO)₂Ph | |
| 386 | C—Me | NEt₂ | 2-Cl-4,6-(MeO)₂Ph | |
| 387 | C—Me | NH-3-pentyl | 2-Cl-4,6-(MeO)₂Ph | |
| 388 | C—Me | NHCH(Et)CH₂CH₂OMe | 2-Cl-4,6-(MeO)₂Ph | |
| 389 | C—Me | NHCH(Me)CH₂CH₂OMe | 2-Cl-4,6-(MeO)₂Ph | |
| 390 | C—Me | NHCH(CH₂OMe)₂ | 2-Me-4,6-(MeO)₂Ph | |
| 391 | C—Me | N(CH₂CH₂OMe)₂ | 2-Me-4,6-(MeO)₂Ph | |
| 392 | C—Me | NHCH(Et)CH₂OMe | 2-Me-4,6-(MeO)₂Ph | |
| 393 | C—Me | N(c-Pr)CH₂CH₂CN | 2-Me-4,6-(MeO)₂Ph | |
| 395 | C—Me | NEt₂ | 2-Me-4,6-(MeO)₂Ph | |
| 396 | C—Me | NH-3-pentyl | 2-Me-4,6-(MeO)₂Ph | |
| 397 | C—Me | NHCH(Et)CH₂CH₂OMe | 2-Me-4,6-(MeO)₂Ph | |
| 398 | C—Me | NHCH(Me)CH₂CH₂OMe | 2-Me-4,6-(MeO)₂Ph | |
| 399 | C—Me | N(c-Pr)CH₂CH₂CN | 2-Br-4,6-(MeO)₂Ph | |
| 400 | C—Me | NEt₂ | 2-Br-4,6-(MeO)₂Ph | |
| 401 | C—Me | NH-3-pentyl | 2-Br-4,6-(MeO)₂Ph | |
| 402 | C—Me | NHCH(Et)CH₂CH₂OMe | 2-Br-4,6-(MeO)₂Ph | |
| 403 | C—Me | NHCH(Me)CH₂CH₂OMe | 2-Br-4,6-(MeO)₂Ph | |
| 404 | C—Me | NHCH(Et)CH₂CH₂OMe | 2-Me-4-MeOPh | |
| 405 | C—Me | NHCH(Me)CH₂CH₂OMe | 2-Me-4-MeOPh | |
| 406 | C—Me | NHCH(CH₂OMe)₂ | 2-MeO-4-MePh | |
| 407 | C—Me | N(CH₂CH₂OMe)₂ | 2-MeO-4-MePh | |
| 408 | C—Me | NHCH(Et)CH₂OMe | 2-MeO-4-MePh | |
| 409 | C—Me | N(c-Pr)CH₂CH₂CN | 2-MeO-4-MePh | |
| 410 | C—Me | NEt₂ | 2-MeO-4-MePh | |
| 411 | C—Me | NH-3-pentyl | 2-MeO-4-MePh | |
| 412 | C—Me | NHCH(Et)CH₂CH₂OMe | 2-MeO-4-MePh | |
| 413 | C—Me | NHCH(Me)CH₂CH₂OMe | 2-MeO-4-MePh | |
| 414 | C—Me | NHCH(CH₂OMe)₂ | 2-MeO-4-MePh | |
| 415 | C—Me | N(CH₂CH₂OMe)₂ | 2-MeO-4-MePh | |
| 416 | C—Me | NHCH(Et)CH₂OMe | 2-MeO-4-MePh | |
| 417 | C—Me | N(c-Pr)CH₂CH₂CN | 2-MeO-4-MePh | |
| 418 | C—Me | NEt₂ | 2-MeO-4-MePh | |
| 419 | C—Me | NH-3-pentyl | 2-MeO-4-MePh | |
| 420 | C—Me | NHCH(Et)CH₂CH₂OMe | 2-MeO-4-MePh | |
| 421 | C—Me | NHCH(Me)CH₂CH₂OMe | 2-MeO-4-MePh | |
| 423[bt] | C—Me | NHCH(CH₂OMe)₂ | 2-MeO-4-ClPh | oil |
| 424 | C—Me | N(CH₂CH₂OMe)₂ | 2-MeO-4-ClPh | |
| 425 | C—Me | NHCH(Et)CH₂OMe | 2-MeO-4-ClPh | |
| 426 | C—Me | N(c-Pr)CH₂CH₂CN | 2-MeO-4-ClPh | |
| 427 | C—Me | NEt₂ | 2-MeO-4-ClPh | |
| 428 | C—Me | NH-3-pentyl | 2-MeO-4-ClPh | |
| 429 | C—Me | NHCH(Et)CH₂CH₂OMe | 2-MeO-4-ClPh | |
| 430 | C—Me | NHCH(Me)CH₂CH₂OMe | 2-Me0-4-ClPh | |

Notes for Table 1:

a) Analysis Calcd: C, 52.69, H, 5.17, N, 17.07, Cl, 17.28; Found: C, 52.82, H, 5.06, N, 16.77, Cl, 17.50.

b) CI-HRMS: Calcd: 406.1565, Found: 405.1573 (M+H); Analysis Calcd: C, 59.11; H, 6.20; N, 17.23; Cl: 17.45; Found: C, 59.93; H, 6.34; N, 16.50; Cl: 16.95; NMR (CDCl₃, 300 MHz): 0.95 (t, J=8, 4H), 1.30–1.40 (m, 4H), 1.50–1.75 (m, 4H), 2.35 (s, 3H), 2.48 (s, 3H), 4.30–4.45 (m, 1H), 6.15 (d, J=8, 1H), 7.30 (s, 2H), 7.50 (s, 1H)

c) CI-HRMS: Calcd: 392.1409, Found: 392.1388 (M+H); NMR (CDCl₃, 300 MHz): 1.00 (t, J=8, 3H), 1.35 (t, J=8, 3H), 1.41 (q, J=8, 2H), 1.65–1.85 (m, 2H), 2.30 (s, 3H), 2.40 (s, 3H), 3.85–4.20 (m, 4H), 7.30 (s, 2H), 7.50 (s, 1H).

d) CI-HRMS: Calcd: 404.1409, Found: 404.1408 (M+H); NMR(CDCl₃, 300 MHz): 0.35–0.45 (m, 2H), 0.52–0.62 (m, 2H), 0.98 (t, J=8, 3H), 1.70–1.90 (m, 2H), 2.30 (s, 3H), 2.40 (s, 3H), 3.85–4.02 (m, 2H), 4.02–4.20 (m, 2H), 7.30 (s, 2H), 7.50 (s, 1H).

e) CI-HRMS: Calcd: 424.1307, Found: 424.1307 (M+H): NMR (CDCl₃, 300 MHz): 2.28 (s, 3H), 2.40 (s, 3H), 3.40 (s, 6H), 3.75 (t, J=8, 4H), 4.20–4.45 (m, 4H), 7.30 (s, 2H), 7.50 (s, 1H).

f) CI-HRMS: Calcd: 406.1565, Found: 406.1578 (M+H); NMR (CDCl$_3$, 300 MHz): 0.90 (t, J=8, 3H), 1.00 (t, J=8, 3H), 1.28–1.45 (m, 4H), 1.50–1.80 (m, 4H), 2.35 (s, 3H), 2.50 (s, 3H), 4.20–4.35 (m, 1H), 6.10–6.23 (m, 1H), 7.30 (s, 2H), 7.50 (s, 1H).

g) CI-HRMS: Calcd: 394.1201, Found: 394.1209 (M+H); NMR (CDCl$_3$, 300 MHz): 1.02 (t, J=8, 3H), 1.65–1.90 (m, 2H), 2.35 (s, 3H), 2.48 (s, 3H), 3.40 (s, 3H), 3.50–3.60 (m, 2H), 4.35–4.45 (brs, 1H), 6.50–6.60 (m, 1H), 7.30 (s, 2H), 7.50 (s, 1H).

h) CI-HRMS: Calcd: 364.1096, Found: 364.1093 (M+H); Analysis: Calcd: C, 56.05; H, 5.27; N, 19.23; Cl: 19.46; Found: C, 55.96; H, 5.24; N, 18.93; Cl: 19.25; NMR (CDCl$_3$, 300 MHz): 1.35 (t, J=8, 6H), 2.30 (3, 3H), 2.40 (s, 3H), 3.95–4.15 (m, 4H), 7.30 (s, 2H), 7.50 (d, J=1, 1H).

i) CI-HRMS: Calcd: 438.1464, Found: 438.1454 (M+H); NMR (CDCl$_3$, 300 MHz): 1.22 (t, J=8, 6H), 2.35 (s, 3H), 2.47 (s, 3H), 3.39 (q, J=8, 4H), 3.65 (dd, J=8, 1, 2H), 3.73 (dd, J=8, 1, 2H), 4.55–4.65 (m, 1H), 6.75 (d, J=8, 1H), 7.30 (d, J=1, 2H), 7.50 (s, 1H).

j) CI-HRMS: Calcd: 378.1252, Found: 378.1249 (M+H); Analysis: Calcd: C, 57.15; H, 5.61; N, 18.51; Cl: 18.74; Found: C, 57.56; H, 5.65; N, 18.35; Cl: 18.45; NMR (CDCl$_3$, 300 MHz): 1.00 (t, J=8, 6H), 1.55–1.70 (m, 2H), 1.70–1.85 (m, 2H), 2.35 (s, 3H), 2.50 (s, 3H), 4.15–4.25 (m, 1H), 6.18 (d, J=8, 1H), 7.30 (s, 2H), 7.50 (s, 1H).

k) CI-HRMS: Calcd: 398.0939, Found: 398.0922 (M+H); Analysis: Calcd: C, 60.31; H, 4.30; N, 17.58; Cl: 17.80; Found: C, 60.29; H, 4.59; N, 17.09; Cl: 17.57; NMR (CDCl$_3$, 300 MHz): 2.05 (s, 3H), 2.50 (s, 3H), 3.78 (s, 3H), 7.20–7.45 (m, 7H), 7.50 (d, J=1, 1H).

l) CI-HRMS: Calcd: 392.1409, Found: 392.1391 (M+H); NMR (CDCl$_3$, 300 MHz): 0.98 (t, J=8, 6H), 1.70–1.85 (m, 4H), 2.30 (s, 3H), 2.40 (s, 3H), 3.80–4.10 (m, 4H), 7.30 (s, 2H), 7.50 (d, J=1, 1H).

m) CI-HRMS: Calcd: 392.1409, Found: 392.1415 (M+H); Analysis: Calcd: C, 58.17; H, 5.92; N, 17.85; Cl: 18.07; Found: C, 58.41; H, 5.85: N, 18.10; Cl: 17.75; NMR (CDCl$_3$, 300 MHz): 0.90–1.05 (m, 6H), 1.35–1.55 (m, 2H), 1.55–1.85 (m, 4H), 2.35 (s, 3H), 2.48 (s, 3H), 4.20–4.35 (m, 1H), 6.15 (d, J=8, 1H), 7.30 (s, 2H), 7.50 (d, J=1, 1H).

n) CI-HRMS: Calcd: 337.0623, Found: 337.0689 (M+H); Analysis: Calcd: C, 53.43; H, 4.18; N, 16.62; Cl: 21.03; Found: C, 53.56; H, 4.33; N, 16.56; Cl: 20.75; NMR (CDCl$_3$, 300 MHz): 1.60 (t, J=8, 3H), 2.40 (s, 3H), 2.55 (s, 3H), 4.80 (q, J=8, 2H), 7.30 (d, J=8, 1H), 7.35 (dd, J=8, 1, 1H), 7.55 (d, J=1, 1H)

o) CI-HRMS: Calcd: 383.2321, Found: 383.2309 (M+H); NMR (CDCl$_3$, 300 MHz): 2.00 (s, 6H), 2.20 (s, 3H), 2.30 (s, 3H), 2.45 (s, 3H), 3.45 (s, 6H), 3.61 (dd, J=8, 8, 2H), 3.70 (dd, J=8, 8, 2H), 4.60–4.70 (m, 1H), 6.70 (d, J=8, 1H), 6.94 (s, 2H).

p) CI-HRMS: Calcd: 370.2243, Found: 370.2246 (M+H); Analysis: Calcd: C, 65.02; H, 7.38; N, 18.96; Found: C, 65.22; H, 7.39; N, 18.71; NMR (CDCl$_3$, 300 MHz): 2.18 (s, 3H), 2.30 (s, 3H), 2.45 (s, 3H), 3.45 (s, 6H), 3.60 (dd, J=8, 8, 2H), 3.69 (dd, J=8, 8, 2H), 4.60–4.70 (m, 1H), 6.70 (d, J=8, 1H), 7.05 (d, J=8, 1H), 7.07 (d, J=8, 1H), 7.10 (s, 1H).

q) CI-HRMS: Calcd: 384.2400, Found: 384.2393 (M+H); NMR (CDCl$_3$, 300 MHz): 2.16 (s, 3H), 2.25 (s, 3H), 2.35 (s, 3H), 2.39 (s, 3H), 3.40 (s, 6H), 3.77 (t, J=8, 4H), 4.20–4.45 (m, 4H), 7.02 (d, J=8, 1H) 7.05 (s, 1H), 7.10 (d, J=7, 1H).

r) CI-HRMS: Calcd: 354.2294, Found: 354.2271 (M+H); Analysis: Calcd: C, 67.96; H, 7.71; N, 19.81; Found: C, 67.56; H, 7.37; N, 19.60; NMR (CDCl$_3$, 300 MHz): 1.03 (t, J=8, 3H), 1.65–1.88 (m, 2H), 2.17 (s, 3H), 2.30 (s, 3H), 2.35 (s, 3H), 2.45 (s, 3H), 3.40 (s, 3H), 3.50–3.62 (m, 2H), 4.30–4.45 (m, 1H), 6.51 (d, J=8, 1H), 7.04 (d, J=8, 1H), 7.10 (d, J=8, 1H), 7.12 (s, 1H).

s) CI-HRMS: Calcd: 338.2345, Found: 338.2332 (M+H); Analysis: Calcd: C, 71.18; H, 8.06; N, 20.75; Found: C, 71.43; H, 7.80; N, 20.70; NMR (CDCl$_3$, 300 MHz): 1.00 (t, J=8, 6H), 1.55–1.70 (m, 2H), 1.70–1.85 (m, 2H), 2.19 (s, 3H), 2.30 (s, 3H), 2.35 (s, 3H), 2.46 (s, 3H), 4.15–4.26 (m, 1H), 6.17 (d, J=8, 1H), 7.06 (d, J=8, 1H), 7.10 (d, J=1, 1H), 7.13 (s, 1H).

t) CI-HRMS: Calcd: 324.2188, Found: 324.2188 (M+H); NMR (CDCl$_3$, 300 MHz): 1.25 (t, J=8, 6H), 2.16 (s, 3H), 2.28 (s, 3H), 2.35 (s, 3H), 2.40 (s, 3H), 3.95–4.20 (m, 4H), 7.05 (dd, J=8, 1, 1H), 7.07 (s, 1H), 7.10 (d, J=1, 1H)

u) CI-HRMS: Calcd: 346.1780, Found: 346.1785 (M+H); Analysis: Calcd: C, 66.07; H, 5.54; N, 28.39; Found: C, 66.07; H, 5.60; N, 27.81; NMR (CDCl$_3$, 300 MHz): 2.15 (s, 3H), 2.32 (s, 3H) 2.17 (s, 3H), 2.52 (s, 3H), 5.25–5.35 (m, 4H), 7.08 (s, 2H), 7.15 (s, 1H).

v) CI-HRMS: Calcd: 340.2137, Found: 340.2137 (M+H); Analysis: Calcd: C, 67.23; H, 7.42; N, 20.63; Found:C, 67.11; H, 7.39; N, 20.26; NMR (CDCl$_3$, 300 MHz): 1.40 (d, J=8, 3H), 2.16 (s, 3H), 2.32 (s, 3H), 2.35 (s, 3H), 2.47 (s, 3H), 3.42 (s, 3H), 3.50–3.60 (m, 2H), 4.50–4.15 (m, 1H), 6.56 (d, J=8, 1H), 7.00–7.15 (m, 3H).

w) CI-HRMS: Calcd: 355.2134, Found: 355.2134 (M+H); NMR (CDCl$_3$, 300 MHz): 1.05 (t, J=8, 3H), 1.85–2.00 (m, 2H), 2.17 (s, 3H), 2.36 (s, 6H), 2.50 (s, 3H), 3.41 (s, 3H), 3.45 (dd, J=8, 3, 1H), 3.82 (dd, J=8, 1, 1H), 5.70–5.80 (m, 1H), 7.00–7.20 (m, 3H).

x) CI-HRMS: Calcd: 364.2501, Found: 364.2501 (M+H); NMR (CDCl$_3$, 300 MHz): 0.35–0.43 (m, 2H), 0.50–0.60 (m, 2H), 0.98 (t, J=8, 3H), 1.20–1.30 (m, 1H), 1.72–1.90 (m, 2H), 2.18 (s, 3H) 2.28 (s, 3H), 2.35 (s, 3H), 2.40 (s, 3H), 3.88–4.03 (m, 2H), 4.03–4.20 (m, 2H), 7.00–7.15 (m, 3H).

y) CI-HRMS: Calcd: 353.2454, Found: 353.2454 (M+H); Analysis: Calcd: C, 68.15; H, 8.02; N, 23.84; Found: C, 67.43; H, 7.81; N, 23.45; NMR (CDCl$_3$, 300 MHz): 1.38 (d, J=8, 3H), 2.18 (s, 3H), 2.30–2.40 (m, 12H), 2.47 93, 3H), 2.60–2.75 (m, 2H), 4.30–4.50 (m, 1H), 6.60–6.70 (m, 1H), 7.00–7.15 (m, 3H).

z) CI-HRMS: Calcd: 361.2140, Found: 361.2128 (M+H); NMR (CDCl$_3$, 300 MHz): 0.75–0.83 (m, 2H), 1.00–1.10 (m, 2H), 2.17 (s, 3H), 2.30 (s, 3H), 2.36 (s, 3H), 2.47 (s, 3H), 2.85 (t, J=8, 2H), 3.30–3.40 (m, 1H), 4.40–4.55 (m, 2H), 7.00–7.18 (m, 3H).

aa) CI-HRMS: Calcd: 363.2297, Found: 363.2311 (M+H); NMR (CDCl$_3$, 300 MHz): 1.01 (t, 3H, J=8), 1.75–1.90 (m,2H), 2.15 (s,3H), 2.19 (s, 3H), 2.35 (s, 3H), 2.40 (s, 3H), 2.40 (s, 3H), 2.98 (t, 2H, J=8), 3.97–4.15 (m, 2H), 4.15–4.30 (m, 2H), 7.03(d, 1H, 1H), 7.08 (d, 1H, J=8), 7.10 (s, 1H).

ab) CI-HRMS: Calcd: 363.2297, Found: 363.2295 (M+H); NMR (CDCl$_3$, 300 MHz): 1.01 (t, 3H, J=8), 1.35–1.55 (m, 2H), 1.75–1.90 (m, 2H), 2.15 (s, 3H), 2.30 (s, 3H), 2.36 (s, 3H), 2.46 (s, 3H), 4.10–4.30 (m, 2H), 4.95–5.10 (br s, 2H), 7.05 (d, 1H, J=8), 7.10 (d, 1H, J=8), 7.15 (s, 1H).

ac) CI-HRMS: Calcd: 368.2450, Found: 368.2436; Analysis: Calcd: C, 68.62, H, 7.95, N, 19.06; Found: C, 68.73, H, 7.97, N, 19.09; NMR (CDCl$_3$, 300 MHz): 1.05 (t, J=8, 3H), 1.70–1.90 (m, 2H), 2.01 (d, J=3, 6H), 2.20 (s, 3H), 2.30 (s, 3H), 2.46, 2.465 (s, s, 3H), 3.42, 3.48 (s, s, 3H), 3.53–3.63 (m, 2H), 4.35–4.45 (m, 1H), 6.73 (d, J=8, 1H), 6.97 (s, 2H).

(ad) CI-HRMS: Calcd: 352.2501, Found: 352.2500 (M+H): Analysis: Calcd: C, 71.76; H, 8.33; N: 19.92, Found: C, 71.55; H, 8.15; N, 19.28; NMR (CDCl$_3$, 300 MHz): 1.01(t, J=8, 6H), 1.58–1.70 (m, 2H), 1.70–1.85 (m, 2H), 2.02 (s, 6H), 2.19 (s, 3H), 2.45 (s, 3H), 4.12–4.28 (m, 1H), 6.18 (d, J=8, 1H), 6.95 (s, 2H).

(ae) CI-HRMS: Calcd: 398.2556, Found: 398.2551 (M+H); Analysis: Calcd: C, 66.47; H, 7.86; N, 17.62, Found: C, 66.74; H, 7.79; N, 17.70; NMR (CDCl$_3$, 300 MHz): 2.00 (s, 6H), 2.12 (s, 3H), 2.30 (s, 3H), 2.37 (s, 3H), 3.40 (s, 6H), 3.78 (t, J=8, 4H), 4.25–4.40 (m, 4H), 6.93 (s, 2H).

(af) CI-HRMS: Calcd: 450.1141, Found: 450.1133 (M+H); Analysis: Calcd: C, 50.67; H, 5.37; N, 15.55; Br: 17.74; Found: C, 52.36; H, 5.84; N, 14.90; Br: 17.44; NMR (CDCl$_3$, 300 MHz): 2.32 (s, 3H), 2.57 (s, 3H), 3.42 (s, 6H), 3.60 (q, J=8, 2H), 3.69 (q, J=8, 2H), 3.82 (s, 3H), 4.60–4.70 (m, 1H), 6.73 (d, J=8, 1H), 6.93 (dd, J=8, 1, 1H), 7.22 (d, J=8, 1H).

ag) CI-HRMS: Calcd: 434.1192, Found: 434.1169 (M+H); Analysis: Calcd: C, 52.54; H, 5.58; N, 16.12; Br: 18.40; Found: C, 52.57; H, 5.60; N, 15.98; Br: 18.22; NMR (CDCl$_3$, 300 MHz): 1.00–1.07 (m, 3H), 1.65–1.85 (m, 2H), 2.35 (s, 3H), 2.46, 2.47 (s, s, 3H), 3.40, 3.45 (s, s, 3H), 3.83 (s, 3H), 4.35–4.45 (m, 1H), 6.55 (d, J=8, 1H), 6.92 (dd, J=8, 1, 1H) 7.20–7.30 (m, 2H).

ah) CI-HRMS: Calcd: 337.2266, Found: 337.2251 (M+H); Analysis: Calcd: C, 70.18; H, 8.06; N, 20.75; Found: C, 70.69; H, 7.66; N: 20.34; NMR (CDCl$_3$, 300 MHz): 1.35 (t, J=8, 6H), 2.01 (s, 6H), 2.15 (s, 3H), 2.30 (s, 3H), 2.38 (s, 3H), 4.07 (q, J=8, 4H), 6.93 (s, 2H).

ai) CI-HRMS: Calcd: 412.2713, Found: 412.2687 (M+H); Analysis: Calcd: C, 67.13; H, 8.08; N, 17.02; Found: C, 67.22; H, 7.85; N, 17.13; NMR (CDCl$_3$, 300 MHz):1.24 (t, J=8, 6H), 2.00 (s, 6H), 2.20 (s, 3H), 2.30 (s, 3H), 2.43 (s, 3H), 3.60 (q, J=8, 4H), 3.66 (dd, J=8, 3, 2H), 3.75 (dd, J=8, 3, 2H), 4.55–4.65 (m, 1H), 6.75 (d, J=8, 1H), 6.95 (s, 2H).

aj) CI-HRMS: Calcd: 398.2556, Found: 398.2545 (M+H); Analysis: Calcd: C, 66.47; H, 7.86; N, 17.62; Found: C, 66.87; H, 7.62; N, 17.75; NMR (CDCl$_3$, 300 MHz): 1.95–2.10 (m, 8H), 2.20 (s, 3H), 2.32 (s, 3H), 2.44 (s, 3H), 3.38 (s, 3H), 3.42 (s, 3H), 3.50–3.70 (m, 4H), 4.58–4.70 (m, 1H), 6.87 (d, J=8, 1H), 6.95 (s, 2H).

ak) CI-HRMS: Calcd: 338.1981, Found: 338.1971 (M+H); Analysis: Calcd: C, 67.63; H, 6.87; N, 20.06; Found: C, 67.67; H, 6.82; N, 20.31; NMR (CDCl$_3$, 300 MHz): 2.15 (s, 3H), 2.29 (s, 3H), 2.35 (s, 3H), 2.43 (s, 3H), 3.90 (t, J=8, 4H), 4.35–4.45 (m, 4H), 7.00–7.15 (m, 3H).

al) CI-HRMS: Calcd: 464.1297, Found: 464.1297 (M+H); NMR (CDCl$_3$, 300 MHz): 2.28 (s, 3H), 2.40 (s, 3H), 3.40 (s, 6H), 3.75 (t, J=8, 4H), 3.83 (s, 3H), 4.20–4.50 (m, 4H), 6.93 (dd, J=8, 1, 1H), 7.20 (s, 1H), 7.24 (d, J=1, 1H).

am) CI-HRMS: Calcd: 418.1242, Found: 418.1223 (M+H); NMR (CDCl$_3$, 300 MHz): 1.00 (t, d, J=8, 1, 6H), 1.55–1.75 (m, 4H), 2.34 (s, 3H), 2.49 (s, 3H), 2.84 (s, 3H), 4.15–4.27 (m, 1H), 6.19 (d, J=8, 1H), 6.93 (dd, J=8, 1, 1H), 7.21–7.30 (m, 2H).

an) CI-HRMS: Calcd: 404.1086, Found: 404.1079(M+H); NMR (CDCl$_3$, 300 MHz): 1.35 (t, J=8, 6H), 2.28 (s, 3H), 2.40 (s, 3H), 3.83 (s, 3H), 3.90–4.08 (m, 2H), 4.08–4.20 (m, 2H), 6.92 (dd, J=8, 1, 1H), 7.20–7.25 (m, 2H).

ao) CI-HRMS: Calcd: 308.1875, Found: 308.1872 (M+H); NMR (CDCl$_3$, 300 MHz): 0.75–0.80 (m, 2H), 0.93–1.00 (m, 2H), 2.16 (s, 3H), 2.28 (s, 3H), 2.35 (s, 3H), 2.53 (s, 3H), 3.00–3.10 (m, 1H), 6.50–6.55 (m, 1H), 7.00–7.15 (m, 3H).

ap) CI-HRMS: Calcd: 397.1988, Found: 397.1984 (M+H); NMR (CDCl$_3$, 300 MHz): 2.43 (s, 3H), 2.50 (s, 3H), 3.43 (s, 3H), 3.61 (dd, J=8, 8, 2H), 3.69 (dd,J=8, 8, 2H), 3.88 (s, 3H), 4.58–4.70 (m, 1H), 6.75 (d, J=8, 1H), 7.20 (dd, J=8, 1, 1H), 7.25 (d, J=1, 1H), 7.40 (s, 1H).

aq) CI-HRMS: Calcd: 375.2297, Found: 375.2286 (M+H); Analysis: Calcd: C, 70.56; H, 7.01; N, 22.44; Found: C, 70.49; H, 6.99; N, 22.45; NMR (CDCl$_3$, 300 MHz): 0.79–0.85 (m, 2H), 1.00–1.05 (m, 1H), 2.00 (s, 6H), 2.19 (s, 3H), 2.32 (s, 3H), 2.44 (s, 3H), 2.84 (t, J=8, 2H), 3.30–3.40 (m, 1H), 4.50 (t, J=8, 2H), 6.95 (s, 2H).

ar) CI-HRMS: Calcd: 434.1192, Found: 434.1189 (M+H); Analysis: Calcd: C, 52.54; H, 5.58; N, 16.12; Br: 18.40; Found: C, 52.75; H, 5.59; N, 16.09; Br: 18.67; NMR (CDCl$_3$, 300 MHz): 2.19 (s, 3H), 2.30 (s, 3H), 2.47 (s, 3H), 3.43 (s, 6H), 3.60 (dd, J=8, 8, 2H), 3.70 (dd, J=8,8, 2H), 4.58–4.70 (m, 1H), 6.71 (d, J=8, 1H), 7.08 (d, J=8, 1H), 7.37 (dd, J=8, 1, 1H), 7.45 (d, J=1, 1H).

as) CI-HRMS: Calcd: 448.1348, Found: 448.1332 (M+H); Analysis: Calcd: C, 53.58; H, 5.85; N, 16.62; Br: 17.82; Found: C, 53.68; H, 5.74; N, 15.52; Br: 13.03; NMR (CDCl$_3$, 300 MHz): 1.95–2.10 (m, 2H), 2.20 (s, 3H), 2.30 (s, 3H), 2.47 (s, 3H), 3.38 (s, 3H), 3.41 (s, 3H), 3.50–3.67 (m, 4H), 4.55–4.70 (m, 1H), 6.89 (d, J=8, 1H), 7.05 (d, J=8, 1H), 7.35 (dd, J=8, 1, 1H), 7.47 (d, J=1, 1H).

at) CI-HRMS: Calcd: 400.2349, Found: 400.2348 (M+H); Analysis: Calcd: C: C, 63.14; H, 7.32; N, 17.53; Found: C, 63.40; H, 7.08; N, 17.14; NMR (CDCl$_3$, 300 MHz): 2.16 (s, 3H), 2.20 (s, 3H), 2.30 (s, 3H), 2.46 (s, 3H), 3.42 (s, 6H), 3.60 (q, J=8, 2H), 3.70 (q, J=8, 2H), 3.85 (s, 3H), 4.59–4.70 (m, 1H), 6.70 (d, J=8, 1H), 6.76 (s, 1H), 6.96 (s, 1H).

au) CI-HRMS: Calcd: 414.2505, Found: 414.2493 (M+H); NMR (CDCl$_3$, 300 MHz): 2.15 (s, 3H), 2.19 (s, 3H), 2.25 (s, 3H), 2.40 (s, 3H), 3.40 (s, 6H), 3.76 (t, J=8, 4H), 3.84 (s, 3H), 4.20–4.45 (m, 4H), 6.77 (s, 1H), 6.93 (s, 1H).

av) CI-HRMS: Calcd: 368.2450, Found: 368.2447 (M+H); NMR (CDCl$_3$, 300 MHz): 1.00 (t, J=8, 6H) 1.55–1.85 (m, 4H), 2.19 (s, 3H), 2.20 (s, 3H), 2.30 (s, 3H), 2.47 (s, 3H), 3.88 (s, 3H), 4.10–4.30 (m, 1H), 6.15 (d, J=8, 1H), 6.78 (s, 1H), 6.98 (s, 1H).

aw) CI-HRMS: Calcd: 353.2216, Found: 353.2197 (M+H); NMR (CDCl$_3$, 300 MHz): 1.35 (t, J=8, 6H), 2.17 (s, 3H), 2.19 (s, 3H), 2.28 (s, 3H), 2.40 (s, 3H), 3.85 (s, 3H), 3.90–4.20 (m, 4H), 6.78 (s, 1H), 6.95 (s, 1H).

ax) CI-HRMS: Calcd: 390.1697, Found: 390.1688 (M+H); Analysis: Calcd: C, 58.53; H, 6.20; N, 17.96; Cl: 9.09; Found: C, 58.95; H, 6.28; N, 17.73; Cl: 9.15; NMR (CDCl$_3$, 300 MHz): 2.35 (s, 3H), 2.37 (s, 3H), 2.48 (s, 3H), 3.42 (s, 6H), 3.60 (dd, J=8, 8, 2H) 3.68 (dd, J=8, 8, 2H), 4.59–4.72 (m, 1H), 6.72 (d, J=8, 1H), 7.12 (d, J=8, 1H), 7.23 (d, J=8, 1H), 7.32 (s, 1H).

ay) CI-HRMS: Calcd: 374.1748, Found: 374.1735 (M+H); Analysis: Calcd: C, 61.04; H, 6.47; N, 18.73; Cl: 9.48; Found: C, 61.47; H, 6.54; N, 18.23; Cl: 9.61; NMR (CDCl$_3$,300 MHz): 1.01 (t, J=8, 3H), 1.62–1.88 (m, 4H), 2.35 (s, 3H), 2.37 (s, 3H), 2.48 (d, J=1, 3H), 3.40, 3.45 (s, s, 3H), 3.50–3.64 (m, 2H), 4.38–4.47 (m, 1H), 6.53 (d, J=8, 1H), 7.12 (d, J=8, 1H), 7.07 (d, J=8, 1H), 7.12 (s, 1H).

az) CI-HRMS: Calcd: 404.1853, Found: 404.1839 (M+H); NMR (CDCl$_3$, 300 MHz): 2.29 (s, 3H), 2.38 (s, 3H), 2.40 (s, 3H), 3.40 (s, 6H), 3.76 (t, J=8, 4H), 4.20–4.45 (m, 4H), 7.11 (d, J=8, 1H), 7.22 (d, J=8, 1H), 7.31 (s, 1H).

ba) CI-HRMS: Calcd: 404.1853, Found: 404.1859 (M+H); Analysis: C, 59.47; H, 6.50; N, 17.34; Cl: 8.79; Found: C, 59.73; H, 6.46; N, 17.10; Cl: 8.73; NMR (CDCl$_3$, 300 MHz): 1.95–2.08 (m, 2H), 2.35 (s, 3H), 2.38 (s, 3H), 2.46 (s, 3H), 3.38 (s, 3H), 3.41 (s, 3H), 3.50–3.65 (m, 4H), 4.56–4.70 (m, 1H), 6.85 (d, J=8, 1H), 7.12 (d, J=8, 1H), 7.45 (d, J=8, 1H), 7.32 (s, 1H).

bb) CI-HRMS: Calcd: 391.2246, Found: 391.2258 (M+H); Analysis: C, 67.67; H, 6.71; N, 21.52; Found: C: 67.93; H, 6.70; N, 21.48; NMR (CDCl$_3$, 300 MHz): 0.76–0.84 (m, 2H), 0.84–0.91 (m, 2H), 1.00–1.08 (m, 2H), 2.15 (s, 3H), 2.20 (s, 3H), 2.29 (s, 3H), 2.45 (s, 3H), 2.85 (t, J=8, 2H), 3.28–3.30 (m, 1H), 3.85 (s, 3H), 6.78 (s, 1H), 6.95 (s, 1H).

bc) CI-HRMS: Calcd: 386.2192, Found: 386.2181 (M+H); Analysis: C, 62.32; H, 7.06; N, 18.17; Found: C: 62.48; H, 6.83; N, 18.15; NMR (CDCl$_3$, 300 MHz): 7.1 (d, 1H, J=8), 6.9 (d, 1H, J=1), 6.8 (dd, 1H, J=8,1), 6.7 (br. d, 1H, J=8), 4.7–4.6 (m, 1H), 3.85 (s, 3H), 3.70–3.55 (m, 4H), 3.45 (s, 6H), 2.5 (s, 3H), 2.3 (s, 3H), 2.15 (s, 3H).

bd) CI-HRMS: Calcd: 400.2349, Found: 400.2336 (M+H); NMR (CDCl$_3$, 300 MHz): 7.1 (d, 1H, J=7), 6.85 (d, 1H, J=1), 6.75 (dd, 1H, J=7,1), 4.45–4.25 (br.s, 4H), 3.75 (t, 4H, J=7), 3.4 (s, 6H), 2.4 (s, 3H), 2.25 (s, 3H), 2.15 (s, 3H).

be) CI-HRMS: Calcd: 370.2243, Found: 370.2247 (M+H); Analysis: C, 65.02; H, 7.38; N, 18.96; Found: C: 65.28; H, 7.27; N, 18.71; NMR (CDCl$_3$, 300 MHz): 7.1 (d, 1H, J=8), 6.85 (d, 1H, J=1), 6.8 (dd, 1H, J=8,1), 6.5 (br. d, 1H, J=1), 4.5–4.3 (m, 1H), 3.85 (s, 3H), 3.65–3.5 (m, 2H), 3.4 (s, 2H), 2.5 (s, 3H), 2.3 (s, 3H), 2.2 (s, 3H), 1.9–1.7 (m, 2H), 1.05 (t, 3H, J=7).

bf) CI-HRMS: Calcd: 379.2246, Found: 379.2248 (M+H); NMR (CDCl$_3$, 300 MHz): 7.1 (d, 1H, J=8), 6.85 (d, 1H, J=1), 6.8 (dd, 1H, J=8,1), 4.3–4.0 (m, 4H), 3.85 (s, 3H), 3.0 (t, 2H, J=7), 2.45 (s, 3H), 2.3 (s, 3H), 2.2 (s, 3H), 1.9–1.8 (m, 2H) 1.0 (t, 3H, J=7).

bg) CI-HRMS: Calcd: 340.2137, Found: 340.2122 (M+H); NMR (CDCl$_3$, 300 MHz): 7.1 (d, 1H, J=8), 6.85 (d, 1H, J=1), 6.75 (dd, 1H, J=8,1), 4.2–4.0 (br.m, 4H), 3.85 (s, 3H, 2.4 (s, 3H), 2.3 (s, 3H), 2.2 (s, 3H), 1.35 (t, 6H, J=7).

bh) CI-HRMS: Calcd: 313.1665, Found: 313.6664 (M+H).

bi) CI-HRMS: Calcd: 400.2349, Found: 400.2346 (M+H); NMR (CDCl$_3$, 300 MHz): 7.1 (d, 1H, J=7), 6.9–6.75 (m, 3H), 4.7–4.55 (m, 1H), 3.8 (s, 3H), 3,7–3.5 (m, 4H), 3.45 (s, 3H), 3.35 (s, 3H), 2.5 (s, 3H), 2.3 (s, 3H), 2.2 (s, 3H), 2.1–1.95 (m, 2H).

bj) CI-HRMS: Calcd: 377.2090, Found: 377.2092 (M+H); Analysis: C, 67.00; H, 6.44; N, 22.32; Found: C: 67.35; H, 6.44; N, 22.23; NMR (CDCl$_3$, 300 MHz): 7.1 (d, 1H, J=8), 6.9 (d, 1H, J=1), 6.8 (dd, 1H, J=8,1), 4.55–4.4 (m, 2H), 3.85 (s, 3H), 3.4–3.3 (m, 1H), 2.85 (t, 2H, J=7), 2.5 (s, 3H), 2.3 (s, 3H), 2.2 (s, 3H), 1.11.0 (m, 2H), 0.85–0.75 (m, 2H).

bk) CI-HRMS: Calcd: 413.2427, Found: 413.2416 (M+H); NMR (CDCl$_3$, 300 Hz): 7.1 (d, 1H, J=8), 6.85 (d, 1H, J=1), 6.75 (dd, 1H, J=8,1), 4.6 (m, 1H), 3.85 (s, 3H), 3.75–3.6(m, 4H), 3.6 (q, 4H, J=7), 2.5 (s, 3H), 2.3 s, 3H), 2.2 (s, 3H), 1.25 (t, 6H, J=7).

bl) CI-HRMS: Calcd: 420.1802, Found: 420.1825(M+H);
bm) CI-HRMS: Calcd: 390.1697, Found: 390.1707(M+H);
bn) CI-HRMS: Calcd: 397.1465, Found: 397.1462(M+H);
bo) CI-HRMS: Calcd: 360.1513, Found: 360.1514(M+H);
bp) CI-HRMS: Calcd: 374.1748, Found: 374.1737(M+H);
bq) CI-HRMS: Calcd: 479.1155, Found: 479.1154(M+H);
br) CI-HRMS: Calcd: 463.1219, Found: 463.1211(M+H); Analysis Calcd: C, 51.96, H, 5.23, N, 15.15, Br: 17.28; Found: C, 52.29, H, 5.62, N, 14.79, Br: 17.47
bs) CI-HRMS: Calcd: 433.1113, Found: 433.1114(M, $^{79}$Br);

bt) NH$_3$—CI MS: Calcd: 406, Found: 406 (M+H)+; NMR (CDCl$_3$, 300 MHz):δ7.28 (d, J=10 Hz, 1H), 7.03 (d, J=8 Hz, 1H), 6.96 (s, 1H), 6.7 (d, J=9, 1H), 4.63 (m, 1H), 3.79 (s, 3H), 3.6 (m, 4H), 3.42 (s, 6H), 2.47 (s, 3H), 2.32 (s, 3H).

Example 431

Preparation of 2,4,7-dimethyl-8-(4-methoxy-2-methylphenyl)[1,5-a]-pyrazolo-1,3,5-triazine (Formula 1, where R$^3$ is CH$_3$, R$_1$ is CH$_3$, Z is C—CH$_3$, Ar is 2,4-dimethylphenyl)

5-Acetamidino-4-(4-methoxy-2-methylphenyl)-3-methylpyrazole, acetic acid salt (602 mg, 2 mmol) was mixed with a saturated NaHCO$_3$ solution (10 mL). The aqueous mixture was extracted with EtOAc three times. The combined organic layers were dried over MgSO$_4$, filtered and concentrated in vacuo. The residue was taken up in toluene (10 mL) and trimethyl orthoacetate (0.36 g, 3 mmol) was added to the suspension. The reaction mixture was heated to reflux temperature under a nitrogen atmosphere and stirred for 16 hours. After being cooled to ambient temperature, the reaction mixture was concentrated in vacuo to give an oily solid. Column chromatography (CHCl$_3$:MeOH::9:1) afforded, after removal of solvent in vacuo, a yellow viscous oil (Rf=0.6, 210 mg, 37% yield): NMR (CDCl$_3$, 300 MHz): 7.15 (d, 1H, J=8), 6.9 (d, 1H, J=1), 6.85 (dd, 1H, J=8,1), 3.85 (s, 3H), 2.95 (s, 3H), 2.65 (s, 3H), 2.4 (s, 3H), 2.15 (s, 3H); CI-HRMS: Calcd: 283.1559, Found: 283.1554 (M+H).

Example 432

7-hydroxy-5-methyl-3-(2-chloro-4-methylphenyl)pyrazolo[1,5-a]pyrimidine (Formula 1 where A is CH, R1 is Me, R$^3$ is OH, Z is C-Me, Ar is 2-chloro-4-methylphenyl)

5-Amino-4-(2-chloro-4-methylphenyl)-3-methylpyrazole (1.86 g, 8.4 mmol) was dissolved in glacial acetic acid (30 mL) with stirring. Ethyl acetoacetate (1.18 mL, 9.2 mmol) was then added dropwise to the resulting solution. The reaction mixture was then heated to reflux temperature and stirred for 16 hours, then cooled to room temperature. Ether (100 mL) was added and the resulting precipitate was collected by filtration. Drying in vacuo afforded a white solid (1.0 g, 42% yield): NMR (CDCl$_3$, 300 Hz): 8.70 (br.s 1H), 7.29 (s, 1H), 7.21–7.09 (m, 2H), 5.62 (s, 1H), 2.35 (s, 6H), 2.29 (s, 3H); CI-MS: 288 (M+H).

Example 433

7-chloro-5-methyl-3-(2-chloro-4-methylphenyl)pyrazolo[1,5-a]pyrimidine (Formula 1 where A is CH, R1 is Me, R$^3$ is Cl, Z is C-Me, Ar is 2-chloro-4-methylphenyl)

A mixture of 7-hydroxy-5-methyl-3-(2-chloro-4-methylphenyl)-pyrazolo[1,5-a]pyrimidine (1.0 g, 3.5 mmol), phosphorus oxychloride (2.7 g, 1.64 mL, 17.4 mmol), N,N-diethylaniline (0.63 g, 0.7 mL, 4.2 mmol) and toluene (20 mL) was stirred at reflux temperature for 3 hours, then it was cooled to ambient temperature. The volatiles were removed in vacuo. Flash chromatography (EtOAc:hexane::1:2) on the residue gave 7-chloro-5-methyl-3-(2-chloro-4-methylphenyl)pyrazolo[1,5-a]pyrimidine (900 mg, 84% yield) as a yellow oil: NMR (CDCl$_3$, 300 Hz): 7.35 (s, 1H), 7.28–7.26 (m, 1H), 71.6 (d, 1H, J=7), 6.80 (s, 1H), 2.55 (s, 3H), 2.45 (s, 3H), 2.40 (s, 3H); CI-MS: 306 (M+H).

Example 434

7-(pentyl-3-amino)-5-methyl-3-(2-chloro-4-methylphenyl)pyrazolo[1,5-a]pyrimidine (Formula 1 where A is CH, R1 is Me, R3 is pentyl-3-amino, Z is C-Me, Ar is 2-chloro-4-methylphenyl)

A solution of substituents independently selected at each occurrence from $C_1$–$C_6$ alkyl, $C_3$–$C_6$ cycloalkyl, halo, $C_1$–$C_4$ haloalkyl, cyano, $OR^{15}$, SH, $S(O)_nR^{13}$, $COR^{15}$, $CO_2R^{15}$, $OC(O)R^{13}$, $NR^8COR^{15}$, $N(COR^{15})_2$, $NR^8CONR^{16}R^{15}$, $NR^8CO_2R^{13}$, $NR^{16}R^{15}$, $CONR^{16}R^{15}$, aryl, heteroaryl or heterocyclyl,
-aryl, aryl($C_1$–$C_4$ alkyl), heteroaryl, heteroaryl($C_1$–$C_4$ alkyl), heterocyclyl or heterocyclyl($C_1$–$C_4$ alkyl);

3-pentylamine (394 mg, 6.5 mmol) and 7-chloro-5-methyl-3-(2-chloro-4-methylphenyl)pyrazolo[1,5-a]pyrimidine (200 mg, 0.65 mmol) in dimethylsulfoxide (DMSO, 10 mL) was stirred at 150° C. for 2 hours; then it was cooled to ambient temperature. The reaction mixture was then poured onto water (100 mL) and mixed. Three extractions with dichloromethane, washing the combined organic layers with brine, drying over $MgSO_4$, filtration and removal of solvent in vacuo produced a yellow solid. Flash chromatography (EtOAc:hexanes::1:4) afforded a white solid (140 mg, 60% yield): mp 139–141° C.; NMR ($CDCl_3$, 300 Hz):7.32 (s, 1H), 7.27 (d, 1H, J=8), 7.12 (d, 1H, J=7), 6.02 (d, 1H, J=9), 5.78 (s, 1H), 3.50–3.39 (m, 1H), 2.45 (s, 3H), 2.36 (s, 6H), 1.82–1.60 (m, 4H), 1.01 (t, 6H, J=8); Analysis Calcd for $CO_2OH_{25}ClN_4$: C, 67.31, H, 7.06, N, 15.70, Cl: 9.93; Found: C, 67.32, H, 6.95, N, 15.50, Cl, 9.93.

The examples delineated in TABLE 2 may be prepared by the methods outlined in Examples 1A, 1B, 432, 433, 434. Commonly used abbreviations are: Ph is phenyl, Pr is propyl, Me is methyl, Et is ethyl, Bu is butyl, Ex is Example, EtOAc is ethyl acetate.

TABLE 2

| Ex. | Z | R3 | Ar | mp(° C.) |
|---|---|---|---|---|
| 435[b] | C—Me | N(CH2CH2OMe)2 | 2,4-Cl2—Ph | 71–73 |
| 436[c] | C—Me | N(Bu)Et | 2,4-Cl2—Ph | 86–87 |
| 437[d] | C—Me | NHCH(Et)CH2OMe | 2,4-Cl2—Ph | 110–111 |
| 438[e] | C—Me | N(Pr)CH2CH2CN | 2,4-Cl2—Ph | 83–85 |
| 439[f] | C—Me | NH-3-pentyl | 2,4-Cl2—Ph | 175–176 |
| 440[g] | C—Me | NHCH(CH2OMe)2 | 2,4-Cl2—Ph | 107 |
| 441[h] | C—Me | NHCH(Et)2 | 2,4-Me2—Ph | oil |
| 442[i] | C—Me | NHCH(CH2OMe)2 | 2,4-Me2—Ph | 103–105 |
| 443[j] | C—Me | N(CH2CH2OMe)2 | 2,4-Me2—Ph | 87–89 |
| 444[k] | C—Me | N(c-Pr)CH2CH2CN | 2,4-Me2—Ph | 133 (dec) |
| 445[l] | C—Me | N(CH2CH2OMe)2 | 2-Cl,4-MePh | 77–78 |
| 446[m] | C—Me | NHCH(CH2OMe)2 | 2-Cl,4-MePh | 131–133 |
| 447[n] | C—Me | NHCH(Et)2 | 2-Cl,4-MePh | 139–141 |
| 448[o] | C—Me | NEt2 | 2,4-Me2—Ph | 92–94 |
| 449[p] | C—Me | N(Pr)CH2CH2CN | 2,4-Me2—Ph | 143–144 |
| 450[q] | C—Me | N(Bu)CH2CH2CN | 2,4-Me2—Ph | 115–117 |
| 451[r] | C—Me | NHCH(Et)CH2OMe | 2,4-Me2—Ph | oil |
| 452[s] | C—Me | NHCH(Et)2 | 2-Me,4-MeOPh | 104–106 |
| 453[t] | C—Me | NHCH(CH2OMe)2 | 2-Me,4-MeOPh | 115–116 |
| 454[u] | C—Me | N(CH2CH2OMe)2 | 2-Me,4-MeOPh | oil |
| 455[v] | C—Me | (S)-NHCH(CH2CH2OMe)—(CH2OMe) | 2-Me,4-MeOPh | oil |
| 456[w] | C—Me | (S)-NHCH(CH2CH2OMe)—(CH2OMe) | 2,4-Me2—Ph | oil |
| 457[x] | C—Me | N(CH2CH2OMe)2 | 2-Me,4-ClPh | oil |
| 458[y] | C—Me | NHEt | 2,4-Me2—Ph | oil |
| 459[z] | C—Me | NHCH(Et)2 | 2-Me,4-ClPh | 94–96 |
| 460[aa] | C—Me | NHCH(CH2OMe)2 | 2-Me,4-ClPh | 113–114 |
| 461[ab] | C—Me | N(Ac)Et | 2,4-Me2—Ph | oil |
| 462[ac] | C—Me | (S)-NHCH(CH2CH2OMe)—(CH2OMe) | 2-Me,4-ClPh | oil |
| 463[ad] | C—Me | N(Pr)CH2CH2CN | 2-Me,4-MeOPh | 118–119 |
| 464[ae] | C—Me | NEt2 | 2-Me,4-MeOPh | 97–99 |
| 465[af] | C—Me | (S)-NHCH(CH2CH2OMe)—(CH2OMe) | 2-Cl,4-MePh | 101–103 |
| 466[ag] | C—Me | NEt2 | 2-Cl,4-MePh | 129–130 |
| 467[ah] | C—Me | N(c-Pr)CH2CH2CN | 2-Me,4-MeOPh | 177–178 |
| 468[ai] | C—Me | N(c-Pr)CH2CH2CN | 2-Cl,4-MePh | 162–163 |
| 469[aj] | C—Me | NHCH(Et)CH2OMe | 2-Me,4-MeOPh | oil |
| 470[ak] | C—Me | NHCH(Et)CH2OMe | 2-Cl,4-MePh | 111–113 |
| 471 | C—Me | NHCH(CH2OMe)2 | 2-Cl-4-MeOPh | |
| 472 | C—Me | N(CH2CH2OMe)2 | 2-Cl-4-MeOPh | |
| 473 | C—Me | NHCH(Et)CH2OMe | 2-Cl-4-MeOPh | |
| 474 | C—Me | N(c-Pr)CH2CH2CN | 2-Cl-4-MeOPh | |
| 475 | C—Me | NEt2 | 2-Cl-4-MeOPh | |
| 476 | C—Me | NH-3-pentyl | 2-Cl-4-MeOPh | |
| 477 | C—Me | NHCH(Et)CH2CH2OMe | 2-Cl-4-MeOPh | |
| 478 | C—Me | NHCH(Me)CH2CH2OMe | 2-Cl-4-MeOPh | |

TABLE 2-continued

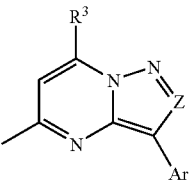

| Ex. | Z | R₃ | Ar | mp(° C.) |
|---|---|---|---|---|
| 479 | C—Me | NHCH(Et)CH$_2$CH$_2$OMe | 2-Br-4-MeOPh | |
| 480 | C—Me | NHCH(Me)CH$_2$CH$_2$OMe | 2-Br-4-MeOPh | |
| 481 | C—Me | NHCH(Et)CH$_2$CH$_2$OMe | 2-Me-4-MeOPh | |
| 482 | C—Me | NHCH(Me)CH$_2$CH$_2$OMe | 2-Me-4-MeOPh | |
| 483 | C—Me | NHCH(CH$_2$OMe)$_2$ | 2-Cl-4,5-(MeO)$_2$Ph | |
| 484 | C—Me | N(CH$_2$CH$_2$OMe)$_2$ | 2-Cl-4,5-(MeO)$_2$Ph | |
| 485 | C—Me | NHCH(Et)CH$_2$OMe | 2-Cl-4,5-(MeO)$_2$Ph | |
| 486 | C—Me | N(c-Pr)CH$_2$CH$_2$CN | 2-Cl-4,5-(MeO)$_2$Ph | |
| 487 | C—Me | NEt$_2$ | 2-Cl-4,5-(MeO)$_2$Ph | 99–101 |
| 488 | C—Me | NH-3-pentyl | 2-Cl-4,5-(MeO)$_2$Ph | 169–170 |
| 489 | C—Me | NHCH(Et)CH$_2$CH$_2$OMe | 2-Cl-4,5-(MeO)$_2$Ph | |
| 490 | C—Me | NHCH(Me)CH$_2$CH$_2$OMe | 2-Cl-4,5-(MeO)$_2$Ph | |
| 491 | C—Me | NHCH(CH$_2$OMe)$_2$ | 2-Br-4,5-(MeO)$_2$Ph | 90–93 |
| 492 | C—Me | N(CH$_2$CH$_2$OMe)$_2$ | 2-Br-4,5-(MeO)$_2$Ph | 110 |
| 493 | C—Me | NHCH(Et)CH$_2$OMe | 2-Br-4,5-(MeO)$_2$Ph | |
| 494 | C—Me | N(c-Pr)CH$_2$CH$_2$CN | 2-Br-4,5-(MeO)$_2$Ph | |
| 495 | C—Me | NEt$_2$ | 2-Br-4,5-(MeO)$_2$Ph | |
| 496 | C—Me | NH-3-pentyl | 2-Br-4,5-(MeO)$_2$Ph | |
| 497 | C—Me | NHCH(Et)CH$_2$CH$_2$OMe | 2-Br-4,5-(MeO)$_2$Ph | |
| 498 | C—Me | NHCH(Me)CH$_2$CH$_2$OMe | 2-Br-4,5-(MeO)$_2$Ph | |
| 499 | C—Me | NHCH(CH$_2$OMe)$_2$ | 2-Cl-4,6-(MeO)$_2$Ph | |
| 500 | C—Me | N(CH$_2$CH$_2$OMe)$_2$ | 2-Cl-4,6-(MeO)$_2$Ph | |
| 501 | C—Me | NHCH(Et)CH$_2$OMe | 2-Cl-4,6-(MeO)$_2$Ph | |
| 502 | C—Me | N(c-Pr)CH$_2$CH$_2$CN | 2-Cl-4,6-(MeO)$_2$Ph | |
| 503 | C—Me | NEt$_2$ | 2-Cl-4,6-(MeO)$_2$Ph | |
| 504 | C—Me | NH-3-pentyl | 2-Cl-4,6-(MeO)$_2$Ph | |
| 505 | C—Me | NHCH(Et)CH$_2$CH$_2$OMe | 2-Cl-4,6-(MeO)$_2$Ph | |
| 506 | C—Me | NHCH(Me)CH$_2$CH$_2$OMe | 2-Cl-4,6-(MeO)$_2$Ph | |
| 507 | C—Me | NHCH(CH$_2$OMe)$_2$ | 2-Me-4,6-(MeO)$_2$Ph | |
| 508 | C—Me | N(CH$_2$CH$_2$OMe)$_2$ | 2-Me-4,6-(MeO)$_2$Ph | |
| 509 | C—Me | NHCH(Et)CH$_2$OMe | 2-Me-4,6-(MeO)$_2$Ph | |
| 510 | C—Me | N(c-Pr)CH$_2$CH$_2$CN | 2-Me-4,6-(MeO)$_2$Ph | |
| 511 | C—Me | NEt$_2$ | 2-Me-4,6-(MeO)$_2$Ph | |
| 512 | C—Me | NH-3-pentyl | 2-Me-4,6-(MeO)$_2$Ph | |
| 513 | C—Me | NHCH(Et)CH$_2$CH$_2$OMe | 2-Me-4,6-(MeO)$_2$Ph | |
| 514 | C—Me | NHCH(Me)CH$_2$CH$_2$OMe | 2-Me-4,6-(MeO)$_2$Ph | |
| 515 | C—Me | N(c-Pr)CH$_2$CH$_2$CN | 2-Br-4,6-(MeO)$_2$Ph | |
| 516 | C—Me | NEt$_2$ | 2-Br-4,6-(MeO)$_2$Ph | |
| 517 | C—Me | NH-3-pentyl | 2-Br-4,6-(MeO)$_2$Ph | |
| 518 | C—Me | NHCH(Et)CH$_2$CH$_2$OMe | 2-Br-4,6-(MeO)$_2$Ph | |
| 519 | C—Me | NHCH(Me)CH$_2$CH$_2$OMe | 2-Br-4,6-(MeO)$_2$Ph | |
| 520 | C—Me | NHCH(Et)CH$_2$CH$_2$OMe | 2-Me-4-MeOPh | |
| 521 | C—Me | NHCH(Me)CH$_2$CH$_2$OMe | 2-Me-4-MeOPh | |
| 522 | C—Me | NHCH(CH$_2$OMe)$_2$ | 2-MeO-4-MePh | |
| 523 | C—Me | N(CH$_2$CH$_2$OMe)$_2$ | 2-MeO-4-MePh | |
| 524 | C—Me | NHCH(Et)CH$_2$OMe | 2-MeO-4-MePh | |
| 525 | C—Me | N(c-Pr)CH$_2$CH$_2$CN | 2-MeO-4-MePh | |
| 526 | C—Me | NEt$_2$ | 2-MeO-4-MePh | |
| 527 | C—Me | NH-3-pentyl | 2-MeO-4-MePh | |
| 528 | C—Me | NHCH(Et)CH$_2$CH$_2$OMe | 2-MeO-4-MePh | |
| 529 | C—Me | NHCH(Me)CH$_2$CH$_2$OMe | 2-MeO-4-MePh | |
| 530 | C—Me | NHCH(CH$_2$OMe)$_2$ | 2-MeO-4-MePh | |
| 531 | C—Me | N(CH$_2$CH$_2$OMe)$_2$ | 2-MeO-4-MePh | |
| 532 | C—Me | NHCH(Et)CH$_2$OMe | 2-MeO-4-MePh | |
| 533 | C—Me | N(c-Pr)CH$_2$CH$_2$CN | 2-MeO-4-MePh | |
| 534 | C—Me | NEt$_2$ | 2-MeO-4-MePh | |
| 535 | C—Me | NH-3-pentyl | 2-MeO-4-MePh | |
| 536 | C—Me | NHCH(Et)CH$_2$CH$_2$OMe | 2-MeO-4-MePh | |
| 537 | C—Me | NHCH(Me)CH$_2$CH$_2$OMe | 2-MeO-4-MePh | |
| 538 | C—Me | NHCH(CH$_2$OMe)$_2$ | 2-MeO-4-ClPh | |
| 539 | C—Me | N(CH$_2$CH$_2$OMe)$_2$ | 2-MeO-4-ClPh | |
| 540 | C—Me | NHCH(Et)CH$_2$OMe | 2-MeO-4-ClPh | |
| 541 | C—Me | N(c-Pr)CH$_2$CH$_2$CN | 2-MeO-4-ClPh | |
| 542 | C—Me | NEt$_2$ | 2-MeO-4-ClPh | |
| 543 | C—Me | NH-3-pentyl | 2-MeO-4-ClPh | |
| 544 | C—Me | NHCH(Et)CH$_2$CH$_2$OMe | 2-MeO-4-ClPh | |
| 545 | C—Me | NHCH(Me)CH$_2$CH$_2$OMe | 2-MeO-4-ClPh | |

Notes for Table 2:
b) CI-HRMS: Calcd: 423.1355; Found: 423.1337 (M+H).
c) Analysis: Calcd: C, 61.38, H, 6.18, N, 14.32: Found: C, 61.54, H, 6.12, N, 14.37.
d) Analysis: Calcd: C, 58.02, H, 5.65, N, 14.24; Found: C, 58.11, H, 5.52, N, 14.26.
e) Analysis: Calcd: C, 59.71, H, 5.26, N, 14.85; Found: C, 59.94, H, 5.09, N, 17.23.
f) Analysis: Calcd: C, 60.48, H, 5.89, N, 14.85, Found: C, 60.62, H, 5.88, N, 14.82.
h) CI-HRMS: Calcd: 337.2388; Found: 337.2392 (M+H).
i) Analysis: Calcd: C, 68.45, H, 7.669, N, 15.21, Found: C, 68.35, H, 7.49 N, 14.91.
j) Analysis: Calcd: C, 69.08, H, 7.915, N, 14.65, Found: C, 68.85, H, 7.83, N, 14.54.
k) Analysis: Calcd: C, 73.51, H, 7.01, N, 19.48, Found: C, 71.57, H, 7.15, N, 19.12.
l) CI-HRMS: Calcd: 403.1899; Found: 403.1901 (M+H).
m) Analysis: Calcd: C, 61.77, H, 6.49, N, 14.41, Cl. 9.13; Found: C, 61.90, H, 6.66, N, 13.62, Cl, 9.25.
n) Analysis: Calcd: C, 67.31, H, 7.06, N, 15.70, Cl. 9.93; Found: C, 67.32, H, 6.95, N, 15.50, Cl, 9.93.
o) Analysis: Calcd:. C, 74.50, H, 8.14, N, 17.38, Found: C, 74.43, H, 7.59, N, 17.16.
p) Analysis: Calcd: C, 73.10, H, 7.54, N, 19.37, Found: C, 73.18, H, 7.59, N, 18.81.
q) Analysis: Calcd: C, 73.57, H, 7.78, N, 18.65, Found: C, 73.55, H, 7.79, N, 18.64.
r) CI-HRMS: Calcd: 353.2333; Found: 353.2341 (M+H).
s) Analysis: Calcd: C, 71.56, H, 8.02, N, 15.90, Found: C, 71.45, H, 7.99, N, 15.88.
t) Analysis: Calcd: C, 65.60, H, 7.34, N, 14.57, Found: C, 65.42, H, 7.24, N, 14.37.
u) CI-HRMS: Calcd: 399.2398; Found: 399.2396 (M+H).
v) CI-HRMS: Calcd: 399.2398; Found: 399.2396 (M+H).
w) CI-HRMS: Calcd: 383.2450; Found: 383.2447 (M+H).
x) CI-HRMS: Calcd: 403.1887; Found: 403.1901 (M+H).
y) CI-HRMS: Calcd: 295.1919; Found: 295.1923 (M+H).
z) Analysis: Calcd: C, 67.31, H, 7.06, N, 15.70, Found: C, 67.12, H, 6.86, N, 15.53.
aa) Analysis: Calcd: C, 61.77, H, 6.49, N, 14.41, Cl, 9.13; Found: C, 62.06, H, 6.37, N, 14.25, Cl, 9.12.
ab) CI-HRMS: Calcd: 337.2017; Found: 337.2028 (M+H).
ac) CI-HRMS: Calcd: 403.1893; Found: 403.1901 (M+H).
ad) Analysis: Calcd: C, 70.00, H, 7.22, N, 18.55, Found: C, 70.05, H, 7.22, N, 18.36.
ae) Analysis: Calcd: C, 70.98, H, 7.74, N, 16.55, Found: C, 71.15, H, 7.46, N, 16.56.
ag) Analysis: Calcd: C, 66.59, H, 6.76, N, 16.34, Found: C, 66.69, H, 6.82, N, 16.20.
ah) Analysis: Calcd: C, 70.38, H, 6.71, N, 18.65, Found: C, 70.35, H, 6.82, N, 18.83.
ai) Analysis: Calcd: C, 66.39, H, 5.85, N, 18.44, Cl, 9.33; Found: C, 66.29, H, 5.51, N, 18.36, Cl, 9.31.
aj) CI-HRMS: Calcd: 369.2278; Found: 369.2291 (M+H).
ak) Analysis: Calcd: C, 64.42, H, 6.77, N, 15.02, Found: C, 64.59, H, 6.51, N, 14.81.

The examples delineated in TABLE 3 may be prepared by the methods outlined in Examples 1, 2, 3 or 6. Commonly used abbreviations are: Ph is phenyl, Pr is propyl, Me is methyl, Et is ethyl, Bu is butyl, Ex is Example.

TABLE 3

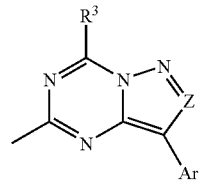

| Ex. | Z | R3 | Ar | mp(° C.) |
|---|---|---|---|---|
| 546[a] | C—Me | NHCH(Et)2 | 2-Me-4-Me2N—Ph | 164–166 |
| 547[b] | C—Me | S—NHCH(CH2CH2OMe)—CH2OMe | 2,4-Me2-Ph | oil |
| 548[c] | C—Me | S—NHCH(CH2CH2OMe)—CH2OMe | 2-Me-4-Cl—Ph | oil |
| 549[d] | C—Me | N(c-Pr)CH2CH2CN | 2-Me-4-Cl—Ph | 115–116 |
| 550[e] | C—Me | NHCH(Et)CH2CN | 2-Me-4-Cl—Ph | 131–132 |
| 551[f] | C—Me | N(Et)2 | 2,3-Me2-4-OMe—Ph | oil |
| 552[g] | C—Me | N(CH2CH2OMe)CH2CH2OH | 2,4-Cl2—Ph | oil |
| 553[h] | C—Me | N(CH2CH2OMe)2 | 2,3-Me2-4-OMe—Ph | oil |
| 554[i] | C—Me | NHCH(Et)2 | 2,3-Me2-4-OMePh | 123–124 |
| 555[j] | C—Me | N(CH2—c-Pr)Pr | 2-Me-4-Cl—Ph | oil |
| 556[k] | C—Me | N(c-Pr)CH2CH2CN | 2,3-Me2-4-OMePh | 158–160 |
| 557 | C—Me | N(c-Pr)Et | 2-Cl-4-OMePh | |
| 558 | C—Me | N(c-Pr)Me | 2-Cl-4-OMePh | |
| 559 | C—Me | N(c-Pr)Pr | 2-Cl-4-OMePh | |
| 560 | C—Me | N(c-Pr)Bu | 2-Cl-4-OMePh | |
| 561[l] | C—Me | N(Et)2 | 2-Cl-4-CN—Ph | 115–117 |
| 562 | C—Me | N(c-Pr)2 | 2-Cl-4-OMe | 127–129 |
| 563[m] | C—Me | NHCH(CH2OH)2 | 2,4-Cl2—Ph | 128–129 |
| 564 | C—Me | N(c-Pr)Et | 2-Br-4,5-(MeO)2Ph | |
| 565 | C—Me | N(c-Pr)Me | 2-Br-4,5-(MeO)2Ph | |
| 566 | C—Me | NH-c-Pr | 2-Me-4-MeOPh | 126–128 |
| 567 | C—Me | NHCH(Et)CH2OH | 2-Me-4-MeOPh | 60–62 |
| 568 | C—Me | NMe2 | 2-Br-4,5-(MeO)2Ph | |
| 569 | C—Me | NHCH(Et)2 | 2-Me-4-MeOPh | 103–105 |
| 570 | C—Me | N(c-Pr)Et | 2-Me-4-MeOPh | 173–174 |

TABLE 3-continued

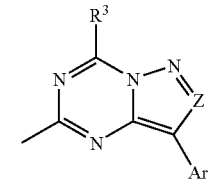

| Ex. | Z | R$_3$ | Ar | mp(° C.) |
| --- | --- | --- | --- | --- |
| 571 | C—Me | NH-2-pentyl | 2,4-Cl$_2$—Ph | 118–120 |
| 572 | C—Me | NHCH(Et)CH2CN | 2,4-Cl$_2$—Ph | 141–142 |
| 573 | C—Me | NHCH(Pr)CH2OMe | 2,4-Cl$_2$—Ph | 87–88 |
| 574 | C—Me | NHCH(CH2-iPr)CH2OMe | 2,4-Cl$_2$—Ph | amorphous |
| 575 | C—Me | NH-2-butyl | 2,4-Me$_2$—Ph | oil |
| 576 | C—Me | NH-2-pentyl | 2,4-Me$_2$—Ph | oil |
| 577 | C—Me | NH-2-hexyl | 2,4-Me$_2$—Ph | oil |
| 578 | C—Me | NHCH(i-Pr)Me | 2,4-Me$_2$—Ph | oil |
| 579 | C—Me | NHCH(Me)CH2-iPr | 2,4-Me$_2$—Ph | oil |
| 580 | C—Me | NHCH(Me)-c-C6H11 | 2,4-Me$_2$—Ph | oil |
| 581 | C—Me | NH-2-indanyl | 2,4-Me$_2$—Ph | oil |
| 582 | C—Me | NH-1-indanyl | 2,4-Me$_2$—Ph | oil |
| 583 | C—Me | NHCH(Me)Ph | 2,4-Me$_2$—Ph | oil |
| 584 | C—Me | NHCH(Me)CH$_2$—(4-ClPh) | 2,4-Me$_2$—Ph | oil |
| 585 | C—Me | NHCH(Me)CH$_2$COCH$_3$ | 2,4-Me$_2$—Ph | oil |
| 586 | C—Me | NHCH(Ph)CH$_2$Ph | 2,4-Me$_2$—Ph | oil |
| 587 | C—Me | NHCH(Me)(CH$_2$)3NEt$_2$ | 2,4-Me$_2$—Ph | oil |
| 588 | C—Me | NH—(2-Ph-c-C$_3$H$_4$) | 2,4-Me$_2$—Ph | oil |
| 589 | C—Me | NHCH(Et)CH$_2$CN | 2,4-Me$_2$—Ph | 119–120 |
| 590 | C—Me | NH-3-hexyl | 2,4-Me$_2$—Ph | oil |
| 591[n] | C—Me | NEt$_2$ | 2-MeO-4-ClPh | oil |
| 592[o] | C—Me | NHCH(Et)$_2$ | 2-MeO-4-ClPh | oil |
| 593[p] | C—Me | NHCH(Et)CH$_2$OMe | 2-MeO-4-ClPh | oil |
| 594 | C—Me | NMe$_2$ | 2-MeO-4-ClPh | oil |
| 595[q] | C—Me | NHCH(Et)$_2$ | 2-OMe-4-MePh | oil |
| 596[r] | C—Me | NEt$_2$ | 2-OMe-4-MePh | oil |
| 597[s] | C-c-Pr | NHCH(CH$_2$OMe)$_2$ | 2,4-Cl$_2$—Ph | oil |
| 598 | C—Me | N(c-Pr)Et | 2,4-Me$_2$—Ph | |
| 599 | C—Me | N(c-Pr)Et | 2,4-Cl$_2$—Ph | |
| 600 | C—Me | N(c-Pr)Et | 2,4,6-Me$_3$—Ph | |
| 601 | C—Me | N(c-Pr)Et | 2-Me-4-Cl—Ph | |
| 602 | C—Me | N(c-Pr)Et | 2-Cl-4-Me—Ph | |
| 603 | C—Me | NHCH(c-Pr)$_2$ | 2,4-Cl$_2$—Ph | |
| 604 | C—Me | NHCH(c-Pr)$_2$ | 2,4-Me$_2$—Ph | |
| 605 | C—Me | NHCH(c-Pr)$_2$ | 2-Me-4-Cl—Ph | |
| 606 | C—Me | NHCH(c-Pr)$_2$ | 2-Cl-4-Me—Ph | |
| 607 | C—Me | NHCH(c-Pr)$_2$ | 2-Me-4-OMe—Ph | |
| 608 | C—Me | NHCH(c-Pr)$_2$ | 2-Cl-4-OMe—Ph | |
| 609 | C—Me | NHCH(CH$_2$OMe)$_2$ | 2-Cl-5-F—OMePh | |
| 610 | C—Me | NEt$_2$ | 2-Cl-5-F—OMePh | |
| 611 | C—Me | N(c-Pr)CH$_2$CH$_2$CN | 2-Cl-5-F—OMePh | |
| 612 | C—Me | NHCH(Et)$_2$ | 2-Cl-5-F—OMePh | |
| 613 | C—Me | N(CH$_2$CH$_2$OMe)$_2$ | 2-Cl-5-F—OMePh | |
| 614 | C—Me | NEt$_2$ | 2,6-Me$_2$-pyrid-3-yl | |
| 615 | C—Me | N(c-Pr)CH$_2$CH$_2$CN | 2,6-Me$_2$-pyrid-3-yl | |
| 616 | C—Me | NHCH(Et)$_2$ | 2,6-Me$_2$-pyrid-3-yl | |
| 617 | C—Me | N(CH$_2$CH$_2$OMe)$_2$ | 2,6-Me$_2$-pyrid-3-yl | |
| 618 | C—OH | NHCH(CH$_2$OMe)$_2$ | 2,4-Me$_2$—Ph | |
| 619 | C—OH | NEt$_2$ | 2,4-Me$_2$—Ph | |
| 620 | C—OH | N(c-Pr)CH$_2$CH$_2$CN | 2,4-Me$_2$—Ph | |
| 621 | C—OH | NHCH(Et)$_2$ | 2,4-Me$_2$—Ph | |
| 623 | C—OH | N(CH$_2$CH$_2$OMe)$_2$ | 2,4-Me$_2$—Ph | |
| 624 | C—NEt$_2$ | NHCH(CH$_2$OMe)$_2$ | 2,4-Me$_2$—Ph | |
| 625 | C—NEt$_2$ | NEt$_2$ | 2,4-Me$_2$—Ph | |
| 626 | C—NEt$_2$ | N(c-Pr)CH$_2$CH$_2$CN | 2,4-Me$_2$—Ph | |
| 627 | C—NEt$_2$ | NHCH(Et)$_2$ | 2,4-Me$_2$—Ph | |
| 628 | C—NEt$_2$ | N(CH$_2$CH$_2$OMe)$_2$ | 2,4-Me$_2$—Ph | |
| 629 | C—Me | NHCH(Et)$_2$ | 2-Me-4-CN—Ph | |
| 630 | C—Me | N(CH$_2$CH$_2$OMe)$_2$ | 2-Me-4-CN—Ph | |

Notes for Table 3:
a) CI-HRMS: Calcd:367.2610, Found: 367.2607 (M+H);
b) CI-HRMS: Calcd:384.2400, Found: 384.2393 (M+H);
c) CI-HRMS: Calcd:404.1853, Found: 404.1844 (M+H);
d) CI-HRMS: Calcd:381.1594, Found: 381.1596 (M+H);
Analysis: Calcd: C, 63.07, H, 5.57, N, 22.07, Cl, 9.32; Found: C, 63.40, H, 5.55, N, 21.96, Cl: 9.15
e) CI-HRMS: Calcd:369.1594, Found: 369.1576 (M+H);

f) CI-HRMS: Calcd:354.2216, Found: 354.2211 (M+H);
g) CI-HRMS: Calcd:410.1072, Found: 410.1075 (M+H);
h) CI-HRMS: Calcd:414.2427, Found: 414.2427(M+H);
i) CI-HRMS: Calcd:368.2372, Found: 368.2372(M+H);
j) CI-HRMS: Calcd:384.1955, Found: 384.1947(M+H);
k) CI-HRMS: Calcd:391.2168, Found: 391.2160(M+H);
l) CI-HRMS: Calcd:335.1984, Found: 335.1961(M+H);
m) CI-HRMS: Calcd:382.0759, Found: 382.0765(M+H);
n) $NH_3$-CI MS: Calcd: 360, Found: 360 (M+H)+
o) $NH_3$-CI MS: Calcd: 374, Found: 374 (M+H)+; NMR ($CDCl_3$, 300 MHz):δ7.29 (d, J=8.4 Hz, 1H), 7.04 (dd, J=1.8, 8 Hz, 1H), 6.96 (d, J=1.8 Hz, 1H), 6.15 (d, J=10, 1H), 4.19 (m, 1H), 3.81 (s, 3H), 2.47 (s, 3H), 2.32 (s, 3H), 1.65 (m, 4H), 0.99 (t, J=7.32 Hz, 6H)
p) $NH_3$-CI MS: Calcd: 390, Found: 390 (M+H)+; NMR ($CDCl_3$, 300 MHz): δ7.28 (d, J=8 Hz, 1H), 7.03 (d, J=8 Hz, 1H), 6.96 (s, 1H), 6.52 (d, J=9 Hz, 1H), 4.36 (m, 1H), 3.8 (s, 3H), 3.55 (m, 2H), 3.39 (s, 3H), 2.47 (s, 3H), 2.32 (s, 3H), 1.76 (m, 2H), 1.01 (t, J=7.32 Hz, 3H).
q) CI-HRMS: Calcd: 354.2294, Found: 354.2279 (M+H)+
r) CI-HRMS: Calcd: 340.2137, Found: 340.2138 (M+H)+
s) CI-HRMS: Calcd: 436.1307, Found: 436.1296 (M+H)+

The examples delineated in TABLE 4 may be prepared by the methods outlined in Examples 1A, 1B, 432, 433, 434. Commonly used abbreviations are: Ph is phenyl, Pr is propyl, Me is methyl, Et is ethyl, Bu is butyl, Ex is Example, EtOAc is ethyl acetate.

TABLE 4

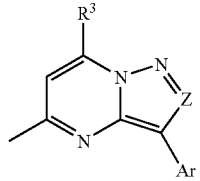

| Ex. | Z | $R_3$ | Ar | mp (° C.) |
|---|---|---|---|---|
| 631 | C—Me | $NHCH(Et)_2$ | 2-Br-4,5-$(MeO)_2$Ph | 160–161 |
| 632 | C—Me | $NHCH(Et)_2$ | 2-Br-4-MeOPh | 110–111 |
| 633 | C—Me | $N(CH_2CH_2OMe)_2$ | 2-Br-4-MeOPh | 74–76 |
| 634 | C—Me | $NHCH(CH_2OMe)_2$ | 2-Br-4-MeOPh | 128–130 |
| 635 | C—Me | $N(Et)_2$ | 2-Me-4-ClPh | 113–114 |
| 636 | C—Me | N(c-Pr)Et | 2,4-$Cl_2$Ph | |
| 637 | C—Me | N(c-Pr)Et | 2,4-$Me_2$Ph | |
| 638 | C—Me | N(c-Pr)Et | 2,4,6-$Me_3$Ph | |
| 639 | C—Me | N(c-Pr)Et | 2-Me-4-MeOPh | |
| 640 | C—Me | N(c-Pr)Et | 2-Cl-4-MeOPh | |
| 641 | C—Me | N(c-Pr)Et | 2-Cl-4-MePh | |
| 642 | C—Me | N(c-Pr)Et | 2-Me-4-ClPh | |
| 643 | C—Me | $NHCH(c-Pr)_2$ | 2,4-$Cl_2$—Ph | |
| 644 | C—Me | $NHCH(c-Pr)_2$ | 2,4-$Me_2$—Ph | |
| 645 | C—Me | $NHCH(c-Pr)_2$ | 2-Me-4-Cl—Ph | |
| 646 | C—Me | $NHCH(c-Pr)_2$ | 2-Cl-4-Me—Ph | |
| 647 | C—Me | $NHCH(c-Pr)_2$ | 2-Me-4-OMe—Ph | |
| 648 | C—Me | $NHCH(c-Pr)_2$ | 2-Cl-4-OMe—Ph | |
| 649 | C—Me | $NHCH(CH_2OMe)_2$ | 2-Cl-5-F-OMePh | |
| 650 | C—Me | $NEt_2$ | 2-Cl-5-F-OMePh | |
| 651 | C—Me | $N(c-Pr)CH_2CH_2CN$ | 2-Cl-5-F-OMePh | |
| 652 | C—Me | $NHCH(Et)_2$ | 2-Cl-5-F-OMePh | |
| 653 | C—Me | $N(CH_2CH_2OMe)_2$ | 2-Cl-5-F-OMePh | |
| 654 | C—Me | $NEt_2$ | 2,6-$Me_2$-pyrid-3-yl | |
| 655 | C—Me | $N(c-Pr)CH_2CH_2CN$ | 2,6-$Me_2$-pyrid-3-yl | |
| 656 | C—Me | $NHCH(Et)_2$ | 2,6-$Me_2$-pyrid-3-yl | |
| 657 | C—Me | $N(CH_2CH_2OMe)_2$ | 2,6-$Me_2$-pyrid-3-yl | |
| 658 | C—OH | $NHCH(CH_2OMe)_2$ | 2,4-$Me_2$—Ph | |
| 659 | C—OH | $NEt_2$ | 2,4-$Me_2$—Ph | |
| 660 | C—OH | $N(c-Pr)CH_2CH_2CN$ | 2,4-$Me_2$—Ph | |
| 661 | C—OH | $NHCH(Et)_2$ | 2,4-$Me_2$—Ph | |
| 662 | C—OH | $N(CH_2CH_2OMe)_2$ | 2,4-$Me_2$—Ph | |

TABLE 4-continued

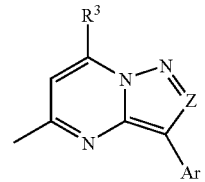

| Ex. | Z | $R_3$ | Ar | mp (° C.) |
|---|---|---|---|---|
| 663 | C—$NEt_2$ | $NHCH(CH_2OMe)_2$ | 2,4-$Me_2$—Ph | |
| 664 | C—$NEt_2$ | $NEt_2$ | 2,4-$Me_2$—Ph | |
| 665 | C—$NEt_2$ | $N(c-Pr)CH_2CH_2CN$ | 2,4-$Me_2$—Ph | |
| 666 | C—$NEt_2$ | $NHCH(Et)_2$ | 2,4-$Me_2$—Ph | |
| 667 | C—$NEt_2$ | $N(CH_2CH_2OMe)_2$ | 2,4-$Me_2$—Ph | |
| 668 | C—Me | $NHCH(Et)_2$ | 2-Me-4-CN—Ph | |
| 669 | C—Me | $N(CH_2CH_2OMe)_2$ | 2-Me-4-CN—Ph | |

The examples in Tables 5 or 6 may be prepared by the methods illustrated in Examples 1A, 1B, 2, 3, 6, 431, 432, 433, 434 or by appropriate combinations thereof. Commonly used abbreviations are: Ph is phenyl, Pr is propyl, Me is methyl, Et is ethyl, Bu is butyl, Ex is Example.

TABLE 5

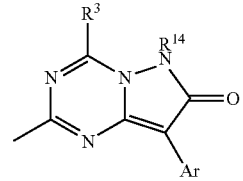

| Ex. | $R_{14}$ | $R_3$ | Ar |
|---|---|---|---|
| 670 | Me | $NHCH(CH_2OMe)_2$ | 2,4-$Cl_2$—Ph |
| 671 | Me | $NHCHPr_2$ | 2,4-$Cl_2$—Ph |
| 672 | Me | NEtBu | 2,4-$Cl_2$—Ph |
| 673 | Me | $NPr(CH_2$-c-$C_3H_5)$ | 2,4-$Cl_2$—Ph |
| 674 | Me | $N(CH_2CH_2OMe)_2$ | 2,4-$Cl_2$—Ph |
| 675 | Me | NH-3-heptyl | 2,4-$Cl_2$—Ph |
| 676 | Me | $NHCH(Et)CH_2OMe$ | 2,4-$Cl_2$—Ph |
| 677 | Me | $NEt_2$ | 2,4-$Cl_2$—Ph |
| 678 | Me | $NHCH(CH_2OEt)_2$ | 2,4-$Cl_2$—Ph |
| 679 | Me | NH-3-pentyl | 2,4-$Cl_2$—Ph |
| 680 | Me | NMePh | 2,4-$Cl_2$—Ph |
| 681 | Me | $NPr_2$ | 2,4-$Cl_2$—Ph |
| 682 | Me | NH-3-hexyl | 2,4-$Cl_2$—Ph |
| 683 | Me | morpholino | 2,4-$Cl_2$—Ph |
| 684 | Me | $N(CH_2Ph)CH_2CH_2OMe$ | 2,4-$Cl_2$—Ph |
| 685 | Me | $NHCH(CH_2Ph)CH_2OMe$ | 2,4-$Cl_2$—Ph |
| 686 | Me | NH-4-tetrahydropyranyl | 2,4-$Cl_2$—Ph |
| 687 | Me | NH-cyclopentyl | 2,4-$Cl_2$—Ph |
| 688 | Me | OEt | 2,4-$Cl_2$—Ph |
| 689 | Me | $OCH(Et)CH_2OMe$ | 2,4-$Cl_2$—Ph |
| 690 | Me | $OCH_2Ph$ | 2,4-$Cl_2$—Ph |
| 691 | Me | O-3-pentyl | 2,4-$Cl_2$—Ph |
| 692 | Me | SEt | 2,4-$Cl_2$—Ph |
| 693 | Me | S(O)Et | 2,4-$Cl_2$—Ph |
| 694 | Me | $SO_2Et$ | 2,4-$Cl_2$—Ph |
| 695 | Me | Ph | 2,4-$Cl_2$—Ph |
| 696 | Me | 2-$CF_3$—Ph | 2,4-$Cl_2$—Ph |
| 697 | Me | 2-Ph—Ph | 2,4-$Cl_2$—Ph |
| 698 | Me | 3-pentyl | 2,4-$Cl_2$—Ph |
| 699 | Me | cyclobutyl | 2,4-$Cl_2$—Ph |
| 700 | Me | 3-pyridyl | 2,4-$Cl_2$—Ph |
| 701 | Me | $CH(Et)CH_2CONMe_2$ | 2,4-$Cl_2$—Ph |
| 702 | Me | $CH(Et)CH_2CH_2NMe_2$ | 2,4-$Cl_2$—Ph |
| 703 | Me | $NHCH(CH_2OMe)_2$ | 2,4,6-$Me_3$—Ph |
| 704 | Me | $NHCHPr_2$ | 2,4,6-$Me_3$—Ph |
| 705 | Me | NEtBu | 2,4,6-$Me_3$—Ph |
| 706 | Me | $NPr(CH_2$-c-$C_3H_5)$ | 2,4,6-$Me_3$—Ph |

TABLE 5-continued

| Ex. | R14 | R3 | Ar |
|---|---|---|---|
| 707 | Me | N(CH$_2$CH$_2$OMe)$_2$ | 2,4,6-Me$_3$—Ph |
| 708 | Me | NH-3-heptyl | 2,4,6-Me$_3$—Ph |
| 709 | Me | NHCH(Et)CH$_2$OMe | 2,4,6-Me$_3$—Ph |
| 710 | Me | NEt$_2$ | 2,4,6-Me$_3$—Ph |
| 711 | Me | NHCH(CH$_2$OEt)$_2$ | 2,4,6-Me$_3$—Ph |
| 712 | Me | NH-3-pentyl | 2,4,6-Me$_3$—Ph |
| 713 | Me | NMePh | 2,4,6-Me$_3$—Ph |
| 714 | Me | NPr$_2$ | 2,4,6-Me$_3$—Ph |
| 715 | Me | NH-3-hexyl | 2,4,6-Me$_3$—Ph |
| 716 | Me | morpholino | 2,4,6-Me$_3$—Ph |
| 717 | Me | N(CH$_2$Ph)CH$_2$CH$_2$OMe | 2,4,6-Me$_3$—Ph |
| 718 | Me | NHCH(CH$_2$Ph)CH$_2$OMe | 2,4,6-Me$_3$—Ph |
| 719 | Me | NH-4-tetrahydropyranyl | 2,4,6-Me$_3$—Ph |
| 720 | Me | NH-cyclopentyl | 2,4,6-Me$_3$—Ph |
| 721 | Me | OEt | 2,4,6-Me$_3$—Ph |
| 722 | Me | OCH(Et)CH$_2$OMe | 2,4,6-Me$_3$—Ph |
| 723 | Me | OCH$_2$Ph | 2,4,6-Me$_3$—Ph |
| 724 | Me | O-3-pentyl | 2,4,6-Me$_3$—Ph |
| 725 | Me | SEt | 2,4,6-Me$_3$—Ph |
| 726 | Me | S(O)Et | 2,4,6-Me$_3$—Ph |
| 727 | Me | SO$_2$Et | 2,4,6-Me$_3$—Ph |
| 728 | Me | CH(CO$_2$Et)$_2$ | 2,4,6-Me$_3$—Ph |
| 729 | Me | C(Et)(CO$_2$Et)$_2$ | 2,4,6-Me$_3$—Ph |
| 730 | Me | CH(Et)CH$_2$OH | 2,4,6-Me$_3$—Ph |
| 731 | Me | CH(Et)CH$_2$OMe | 2,4,6-Me$_3$—Ph |
| 732 | Me | CONMe$_2$ | 2,4,6-Me$_3$—Ph |
| 733 | Me | COCH$_3$ | 2,4,6-Me$_3$—Ph |
| 734 | Me | CH(OH)CH$_3$ | 2,4,6-Me$_3$—Ph |
| 735 | Me | C(OH)Ph-3-pyridyl | 2,4,6-Me$_3$—Ph |
| 736 | Me | Ph | 2,4,6-Me$_3$—Ph |
| 737 | Me | 2-Ph—Ph | 2,4,6-Me$_3$—Ph |
| 738 | Me | 3-pentyl | 2,4,6-Me$_3$—Ph |
| 739 | Me | cyclobutyl | 2,4,6-Me$_3$—Ph |
| 740 | Me | 3-pyridyl | 2,4,6-Me$_3$—Ph |
| 741 | Me | CH(Et)CH$_2$CONMe$_2$ | 2,4,6-Me$_3$—Ph |
| 742 | Me | CH(Et)CH$_2$CH$_2$NMe$_2$ | 2,4,6-Me$_3$—Ph |
| 743 | Me | NHCH(CH$_2$OMe)$_2$ | 2,4-Me$_2$—Ph |
| 744 | Me | N(CH$_2$CH$_2$OMe)$_2$ | 2,4-Me$_2$—Ph |
| 745 | Me | NHCH(Et)CH$_2$OMe | 2,4-Me$_2$—Ph |
| 746 | Me | NH-3-pentyl | 2,4-Me$_2$—Ph |
| 747 | Me | NEt$_2$ | 2,4-Me$_2$—Ph |
| 748 | Me | N(CH$_2$CN)$_2$ | 2,4-Me$_2$—Ph |
| 749 | Me | NHCH(Me)CH$_2$OMe | 2,4-Me$_2$—Ph |
| 750 | Me | OCH(Et)CH$_2$OMe | 2,4-Me$_2$—Ph |
| 751 | Me | NPr-c-C$_3$H$_5$ | 2,4-Me$_2$—Ph |
| 752 | Me | NHCH(Me)CH$_2$NMe$_2$ | 2,4-Me$_2$—Ph |
| 753 | Me | N(c-C$_3$H$_5$)CH$_2$CH$_2$CN | 2,4-Me$_2$—Ph |
| 754 | Me | N(Pr)CH$_2$CH$_2$CN | 2,4-Me$_2$—Ph |
| 755 | Me | N(Bu)CH$_2$CH$_2$CN | 2,4-Me$_2$—Ph |
| 756 | Me | NHCHPr$_2$ | 2,4-Me$_2$—Ph |
| 757 | Me | NEtBu | 2,4-Me$_2$—Ph |
| 758 | Me | NPr(CH$_2$-c-C$_3$H$_5$) | 2,4-Me$_2$—Ph |
| 759 | Me | NH-3-heptyl | 2,4-Me$_2$—Ph |
| 760 | Me | NEt$_2$ | 2,4-Me$_2$—Ph |
| 761 | Me | NHCH(CH$_2$OEt)$_2$ | 2,4-Me$_2$—Ph |
| 762 | Me | NH-3-pentyl | 2,4-Me$_2$—Ph |
| 763 | Me | NMePh | 2,4-Me$_2$—Ph |
| 764 | Me | NPr$_2$ | 2,4-Me$_2$—Ph |
| 765 | Me | NH-3-hexyl | 2,4-Me$_2$—Ph |
| 766 | Me | morpholino | 2,4-Me$_2$—Ph |
| 767 | Me | N(CH$_2$Ph)CH$_2$CH$_2$OMe | 2,4-Me$_2$—Ph |
| 768 | Me | NHCH(CH$_2$Ph)CH$_2$OMe | 2,4-Me$_2$—Ph |
| 769 | Me | NH-4-tetrahydropyranyl | 2,4-Me$_2$—Ph |
| 770 | Me | NH-cyclopentyl | 2,4-Me$_2$—Ph |
| 771 | Me | NHCH(CH$_2$OMe)$_2$ | 2-Me-4-MeO—Ph |
| 772 | Me | N(CH$_2$CH$_2$OMe)$_2$ | 2-Me-4-MeO—Ph |
| 773 | Me | NHCH(Et)CH$_2$OMe | 2-Me-4-MeO—Ph |
| 774 | Me | N(Pr)CH$_2$CH$_2$CN | 2-Me-4-MeO—Ph |
| 775 | Me | OCH(Et)CH$_2$OMe | 2-Me-4-MeO—Ph |
| 776 | Me | NHCH(CH$_2$OMe)$_2$ | 2-Br-4-MeO—Ph |
| 777 | Me | N(CH$_2$CH$_2$OMe)$_2$ | 2-Br-4-MeO—Ph |
| 778 | Me | NHCH(Et)CH$_2$OMe | 2-Br-4-MeO—Ph |
| 779 | Me | N(Pr)CH$_2$CH$_2$CN | 2-Br-4-MeO—Ph |
| 780 | Me | OCH(Et)CH$_2$OMe | 2-Br-4-MeO—Ph |
| 781 | Me | NHCH(CH$_2$OMe)$_2$ | 2-Me-4-NMe$_2$—Ph |
| 782 | Me | N(CH$_2$CH$_2$OMe)$_2$ | 2-Me-4-NMe$_2$—Ph |
| 783 | Me | NHCH(Et)CH$_2$OMe | 2-Me-4-NMe$_2$—Ph |
| 784 | Me | N(Pr)CH$_2$CH$_2$CN | 2-Me-4-NMe$_2$—Ph |
| 785 | Me | OCH(Et)CH$_2$OMe | 2-Me-4-NMe$_2$—Ph |
| 786 | Me | NHCH(CH$_2$OMe)$_2$ | 2-Br-4-NMe$_2$—Ph |
| 787 | Me | N(CH$_2$CH$_2$OMe)$_2$ | 2-Br-4-NMe$_2$—Ph |
| 788 | Me | NHCH(Et)CH$_2$OMe | 2-Br-4-NMe$_2$—Ph |
| 789 | Me | N(Pr)CH$_2$CH$_2$CN | 2-Br-4-NMe$_2$—Ph |
| 790 | Me | OCH(Et)CH$_2$OMe | 2-Br-4-NMe$_2$—Ph |
| 791 | Me | NHCH(CH$_2$OMe)$_2$ | 2-Br-4-i-Pr—Ph |
| 792 | Me | N(CH$_2$CH$_2$OMe)$_2$ | 2-Br-4-i-Pr—Ph |
| 793 | Me | NHCH(Et)CH$_2$OMe | 2-Br-4-i-Pr—Ph |
| 794 | Me | N(Pr)CH$_2$CH$_2$CN | 2-Br-4-i-Pr—Ph |
| 795 | Me | OCH(Et)CH$_2$OMe | 2-Br-4-i-Pr—Ph |
| 796 | Me | NHCH(CH$_2$OMe)$_2$ | 2-Br-4-Me—Ph |
| 797 | Me | N(CH$_2$CH$_2$OMe)$_2$ | 2-Br-4-Me—Ph |
| 798 | Me | NHCH(Et)CH$_2$OMe | 2-Br-4-Me—Ph |
| 799 | Me | N(Pr)CH$_2$CH$_2$CN | 2-Br-4-Me—Ph |
| 800 | Me | OCH(Et)CH$_2$OMe | 2-Br-4-Me—Ph |
| 801 | Me | NHCH(CH$_2$OMe)$_2$ | 2-Me-4-Br—Ph |
| 802 | Me | N(CH$_2$CH$_2$OMe)$_2$ | 2-Me-4-Br—Ph |
| 803 | Me | NHCH(Et)CH$_2$OMe | 2-Me-4-Br—Ph |
| 804 | Me | N(Pr)CH$_2$CH$_2$CN | 2-Me-4-Br—Ph |
| 805 | Me | OCH(Et)CH$_2$OMe | 2-Me-4-Br—Ph |
| 806 | Me | NHCH(CH$_2$OMe)$_2$ | 2-Cl-4,6-Me$_2$—Ph |
| 807 | Me | N(CH$_2$CH$_2$OMe)$_2$ | 2-Cl-4,6-Me$_2$—Ph |
| 808 | Me | NHCH(CH$_2$OMe)$_2$ | 4-Br-2,6-(Me)$_2$—Ph |
| 809 | Me | N(CH$_2$CH$_2$OMe)$_2$ | 4-Br-2,6-(Me)$_2$—Ph |
| 810 | Me | NHCH(CH$_2$OMe)$_2$ | 4-i-Pr-2-SMe—Ph |
| 811 | Me | N(CH$_2$CH$_2$OMe)$_2$ | 4-i-Pr-2-SMe—Ph |
| 812 | Me | NHCH(CH$_2$OMe)$_2$ | 2-Br-4-CF$_3$—Ph |
| 813 | Me | N(CH$_2$CH$_2$OMe)$_2$ | 2-Br-4-CF$_3$—Ph |
| 814 | Me | NHCH(CH$_2$OMe)$_2$ | 2-Br-4,6-(MeO)$_2$—Ph |
| 815 | Me | N(CH$_2$CH$_2$OMe)$_2$ | 2-Br-4,6-(MeO)$_2$—Ph |
| 816 | Me | NHCH(CH$_2$OMe)$_2$ | 2-Cl-4,6-(MeO)$_2$—Ph |
| 817 | Me | N(CH$_2$CH$_2$OMe)$_2$ | 2-Cl-4,6-(MeO)$_2$—Ph |
| 818 | Me | NHCH(CH$_2$OMe)$_2$ | 2,6-(Me)$_2$-4-SMe—Ph |
| 819 | Me | N(CH$_2$CH$_2$OMe)$_2$ | 2,6-(Me)$_2$-4-SMe—Ph |
| 820 | Me | NHCH(CH$_2$OMe)$_2$ | 4-(COMe)-2-Br—Ph |
| 821 | Me | N(CH$_2$CH$_2$OMe)$_2$ | 4-(COMe)-2-Br—Ph |
| 822 | Me | NHCH(CH$_2$OMe)$_2$ | 2,4,6-Me$_3$-pyrid-3-yl |
| 823 | Me | N(CH$_2$CH$_2$OMe)$_2$ | 2,4,6-Me$_3$-pyrid-3-yl |
| 824 | Me | NHCH(CH$_2$OMe)$_2$ | 2,4-(Br)$_2$—Ph |
| 825 | Me | N(CH$_2$CH$_2$OMe)$_2$ | 2,4-(Br)$_2$—Ph |
| 826 | Me | NHCH(CH$_2$OMe)$_2$ | 4-i-Pr-2-SMe—Ph |
| 827 | Me | N(CH$_2$CH$_2$OMe)$_2$ | 4-i-Pr-2-SMe—Ph |
| 828 | Me | NHCH(CH$_2$OMe)$_2$ | 4-i-Pr-2-SO$_2$Me—Ph |
| 829 | Me | N(CH$_2$CH$_2$OMe)$_2$ | 4-i-Pr-2-SO$_2$Me—Ph |
| 830 | Me | NHCH(CH$_2$OMe)$_2$ | 2,6-(Me)$_2$-4-SMe—Ph |
| 831 | Me | N(CH$_2$CH$_2$OMe)$_2$ | 2,6-(Me)$_2$-4-SMe—Ph |
| 832 | Me | NHCH(CH$_2$OMe)$_2$ | 2,6-(Me)$_2$-4-SO$_2$Me—Ph |
| 833 | Me | N(CH$_2$CH$_2$OMe)$_2$ | 2,6-(Me)$_2$-4-SO$_2$Me—Ph |
| 834 | Me | NHCH(CH$_2$OMe)$_2$ | 2-I-4-i-Pr—Ph |
| 835 | Me | N(CH$_2$CH$_2$OMe)$_2$ | 2-I-4-i-Pr—Ph |
| 836 | Me | NHCH(CH$_2$OMe)$_2$ | 2-Br-4-N(Me)$_2$-6-MeO—Ph |
| 837 | Me | N(CH$_2$CH$_2$OMe)$_2$ | 2-Br-4-N(Me)$_2$-6-MeO—Ph |
| 838 | Me | NEt$_2$ | 2-Br-4-MeO—Ph |
| 839 | Me | NH-3-pentyl | 2-Br-4-MeO—Ph |
| 840 | Me | NHCH(CH$_2$OMe)$_2$ | 2-CN-4-Me—Ph |

TABLE 5-continued

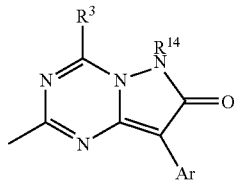

| Ex. | R14 | R3 | Ar |
|---|---|---|---|
| 841 | Me | N(c-C3H5)CH2CH2CN | 2,4,6-Me3—Ph |
| 842 | Me | NHCH(CH2CH2OMe)-CH2OMe | 2-Me-4-Br—Ph |
| 843 | Me | NHCH(CH2OMe)2 | 2,5-Me2-4-MeO—Ph |
| 844 | Me | N(CH2CH2OMe)2 | 2,5-Me2-4-MeO—Ph |
| 845 | Me | NH-3-pentyl | 2,5-Me2-4-MeO—Ph |
| 846 | Me | NEt2 | 2,5-Me2-4-MeO—Ph |
| 847 | Me | NHCH(CH2OMe)2 | 2-Cl-4-MePh |
| 848 | Me | NCH(Et)CH2OMe | 2-Cl-4-MePh |
| 849 | Me | N(CH2CH2OMe)2 | 2-Cl-4-MePh |
| 850 | Me | (S)—NHCH(CH2CH2OMe)-CH2OMe | 2-Cl-4-MePh |
| 851 | Me | N(c-C3H5)CH2CH2CN | 2,5-Me2-4-MeOPh |
| 852 | Me | NEt2 | 2-Me-4-MeOPh |
| 853 | Me | OEt | 2-Me-4-MeOPh |
| 854 | Me | (S)—NHCH(CH2CH2OMe)-CH2OMe | 2-Me-4-MeOPh |
| 855 | Me | N(c-C3H5)CH2CH2CN | 2-Me-4-MeOPh |
| 856 | Me | NHCH(CH2OEt)2 | 2-Me-4-MeOPh |
| 857 | Me | N(c-C3H5) CH2CH2CN | 2,4-Cl2—Ph |
| 858 | Me | NEt2 | 2-Me-4-ClPh |
| 859 | Me | NH-3-pentyl | 2-Me-4-ClPh |
| 860 | Me | N(CH2CH2OMe)2 | 2-Me-4-ClPh |
| 861 | Me | NHCH(CH2OMe)2 | 2-Me-4-ClPh |
| 862 | Me | NEt2 | 2-Me-4-ClPh |
| 863 | Me | NEt2 | 2-Cl-4-MePh |
| 864 | Me | NH-3-pentyl | 2-Cl-4-MePh |
| 865 | Me | NHCH(CH2OMe)2 | 2-Cl-4-MeOPh |
| 866 | Me | N(CH2CH2OMe)2 | 2-Cl-4-MeOPh |
| 867 | Me | NHCH(Et)CH2OMe | 2-Cl-4-MeOPh |
| 868 | Me | N(c-Pr)CH2CH2CN | 2-Cl-4-MeOPh |
| 869 | Me | NEt2 | 2-Cl-4-MeOPh |
| 870 | Me | NH-3-pentyl | 2-Cl-4-MeOPh |
| 871 | Me | NHCH(Et)CH2OMe | 2-Cl-4-MeOPh |
| 872 | Me | NHCH(Me)CH2CH2OMe | 2-Cl-4-MeOPh |
| 873 | Me | NHCH(Et)CH2CH2OMe | 2-Br-4-MeOPh |
| 874 | Me | NHCH(Me)CH2CH2OMe | 2-Br-4-MeOPh |
| 875 | Me | NHCH(Et)CH2CH2OMe | 2-Me-4-MeOPh |
| 876 | Me | NHCH(Me)CH2CH2OMe | 2-Me-4-MeOPh |
| 877 | Me | NHCH(CH2OMe)2 | 2-Cl-4,5-(MeO)2Ph |
| 878 | Me | N(CH2CH2OMe)2 | 2-Cl-4,5-(MeO)2Ph |
| 879 | Me | NHCH(Et)CH2OMe | 2-Cl-4,5-(MeO)2Ph |
| 880 | Me | N(c-Pr)CH2CH2CN | 2-Cl-4,5-(MeO)2Ph |
| 881 | Me | NEt2 | 2-Cl-4,5-(MeO)2Ph |
| 882 | Me | NH-3-pentyl | 2-Cl-4,5-(MeO)2Ph |
| 883 | Me | NHCH(Et)CH2OMe | 2-Cl-4,5-(MeO)2Ph |
| 884 | Me | NHCH(Me)CH2CH2OMe | 2-Cl-4,5-(MeO)2Ph |
| 885 | Me | NHCH(CH2OMe)2 | 2-Br-4,5-(MeO)2Ph |
| 886 | Me | N(CH2CH2OMe)2 | 2-Br-4,5-(MeO)2Ph |
| 887 | Me | NHCH(Et)CH2OMe | 2-Br-4,5-(MeO)2Ph |
| 888 | Me | N(c-Pr)CH2CH2CN | 2-Br-4,5-(MeO)2Ph |
| 889 | Me | NEt2 | 2-Br-4,5-(MeO)2Ph |
| 890 | Me | NH-3-pentyl | 2-Br-4,5-(MeO)2Ph |
| 891 | Me | NHCH(CH2OMe)2 | 2-Cl-4,6-(MeO)2Ph |
| 892 | Me | N(CH2CH2OMe)2 | 2-Cl-4,6-(MeO)2Ph |
| 893 | Me | NEt2 | 2-Cl-4,6-(MeO)2Ph |
| 894 | Me | NH-3-pentyl | 2-Cl-4,6-(MeO)2Ph |
| 895 | Me | NHCH(CH2OMe)2 | 2-Me-4,6-(MeO)2Ph |
| 896 | Me | N(CH2CH2OMe)2 | 2-Me-4,6-(MeO)2Ph |
| 897 | Me | NHCH(Et)CH2OMe | 2-Me-4,6-(MeO)2Ph |
| 898 | Me | NEt2 | 2-Me-4,6-(MeO)2Ph |
| 899 | Me | NH-3-pentyl | 2-Me-4,6-(MeO)2Ph |
| 900 | Me | NHCH(Et)CH2CH2OMe | 2-Me-4-MeOPh |
| 901 | Me | NHCH(Me)CH2CH2OMe | 2-Me-4-MeOPh |
| 902 | Me | NHCH(CH2OMe)2 | 2-MeO-4-MePh |
| 903 | Me | N(CH2CH2OMe)2 | 2-MeO-4-MePh |
| 904 | Me | NHCH(Et)CH2OMe | 2-MeO-4-MePh |

TABLE 5-continued

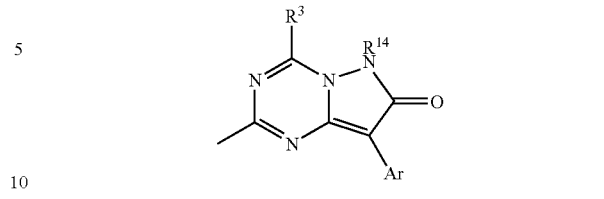

| Ex. | R14 | R3 | Ar |
|---|---|---|---|
| 905 | Me | N(c-Pr)CH2CH2CN | 2-MeO-4-MePh |
| 906 | Me | NEt2 | 2-MeO-4-MePh |
| 907 | Me | NH-3-pentyl | 2-MeO-4-MePh |
| 908 | Me | NHCH(Et)CH2CH2OMe | 2-MeO-4-MePh |
| 909 | Me | NHCH(Me)CH2CH2OMe | 2-MeO-4-MePh |
| 910 | Me | NHCH(CH2OMe)2 | 2-MeO-4-MePh |
| 911 | Me | N(CH2CH2OMe)2 | 2-MeO-4-MePh |
| 912 | Me | NHCH(Et)CH2OMe | 2-MeO-4-MePh |
| 913 | Me | N(c-Pr)CH2CH2CN | 2-MeO-4-MePh |
| 914 | Me | NEt2 | 2-MeO-4-MePh |
| 915 | Me | NH-3-pentyl | 2-MeO-4-MePh |
| 916 | Me | NHCH(CH2OMe)2 | 2-MeO-4-ClPh |
| 917 | Me | N(CH2CH2OMe)2 | 2-MeO-4-ClPh |
| 918 | Me | NHCH(Et)CH2OMe | 2-MeO-4-ClPh |
| 919 | Me | NEt2 | 2-MeO-4-ClPh |
| 920 | Me | NH-3-pentyl | 2-MeO-4-ClPh |

TABLE 6

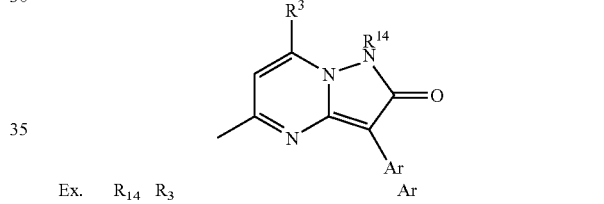

| Ex. | R14 | R3 | Ar |
|---|---|---|---|
| 921 | Me | NHCH(CH2OMe)2 | 2,4-Cl2—Ph |
| 922 | Me | NHCHPr2 | 2,4-Cl2—Ph |
| 923 | Me | NEtBu | 2,4-Cl2—Ph |
| 924 | Me | NPr(CH2-c-C3H5) | 2,4-Cl2—Ph |
| 925 | Me | N(CH2CH2OMe)2 | 2,4-Cl2—Ph |
| 926 | Me | NH-3-heptyl | 2,4-Cl2—Ph |
| 927 | Me | NHCH(Et)CH2OMe | 2,4-Cl2—Ph |
| 928 | Me | NEt2 | 2,4-Cl2—Ph |
| 929 | Me | NHCH(CH2OEt)2 | 2,4-Cl2—Ph |
| 930 | Me | NH-3-pentyl | 2,4-Cl2—Ph |
| 931 | Me | NMePh | 2,4-Cl2—Ph |
| 932 | Me | NPr2 | 2,4-Cl2—Ph |
| 933 | Me | NH-3-hexyl | 2,4-Cl2—Ph |
| 934 | Me | morpholino | 2,4-Cl2—Ph |
| 935 | Me | N(CH2Ph)CH2CH2OMe | 2,4-Cl2—Ph |
| 936 | Me | NHCH(CH2Ph)CH2OMe | 2,4-Cl2—Ph |
| 937 | Me | NH-4-tetrahydropyranyl | 2,4-Cl2—Ph |
| 938 | Me | NH-cyclopentyl | 2,4-Cl2—Ph |
| 939 | Me | OEt | 2,4-Cl2—Ph |
| 940 | Me | OCH(Et)CH2OMe | 2,4-Cl2—Ph |
| 941 | Me | OCH2Ph | 2,4-Cl2—Ph |
| 942 | Me | O-3-pentyl | 2,4-Cl2—Ph |
| 943 | Me | SEt | 2,4-Cl2—Ph |
| 944 | Me | S(O)Et | 2,4-Cl2—Ph |
| 945 | Me | SO2Et | 2,4-Cl2—Ph |
| 946 | Me | Ph | 2,4-Cl2—Ph |
| 947 | Me | 2-CF3—Ph | 2,4-Cl2—Ph |
| 948 | Me | 2-Ph—Ph | 2,4-Cl2—Ph |
| 949 | Me | 3-pentyl | 2,4-Cl2—Ph |
| 950 | Me | cyclobutyl | 2,4-Cl2—Ph |
| 951 | Me | 3-pyridyl | 2,4-Cl2—Ph |
| 952 | Me | CH(Et)CH2CONMe2 | 2,4-Cl2—Ph |
| 953 | Me | CH(Et)CH2CH2NMe2 | 2,4-Cl2—Ph |
| 954 | Me | NHCH(CH2OMe)2 | 2,4,6-Me3—Ph |
| 955 | Me | NHCHPr2 | 2,4,6-Me3—Ph |

TABLE 6-continued

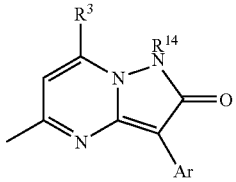

| Ex. | R14 | R3 | Ar |
|---|---|---|---|
| 956 | Me | NEtBu | 2,4,6-Me3—Ph |
| 957 | Me | NPr(CH2-c-C3H5) | 2,4,6-Me3—Ph |
| 958 | Me | N(CH2CH2OMe)2 | 2,4,6-Me3—Ph |
| 959 | Me | NH-3-heptyl | 2,4,6-Me3—Ph |
| 960 | Me | NHCH(Et)CH2OMe | 2,4,6-Me3—Ph |
| 961 | Me | NEt2 | 2,4,6-Me3—Ph |
| 962 | Me | NHCH(CH2OEt)2 | 2,4,6-Me3—Ph |
| 963 | Me | NH-3-pentyl | 2,4,6-Me3—Ph |
| 964 | Me | NMePh | 2,4,6-Me3—Ph |
| 965 | Me | NPr2 | 2,4,6-Me3—Ph |
| 966 | Me | NH-3-hexyl | 2,4,6-Me3—Ph |
| 967 | Me | morpholino | 2,4,6-Me3—Ph |
| 968 | Me | N(CH2Ph)CH2CH2OMe | 2,4,6-Me3—Ph |
| 969 | Me | NHCH(CH2Ph)CH2OMe | 2,4,6-Me3—Ph |
| 970 | Me | NH-4-tetrahydropyranyl | 2,4,6-Me3—Ph |
| 971 | Me | NE-cyclopentyl | 2,4,6-Me3—Ph |
| 972 | Me | OEt | 2,4,6-Me3—Ph |
| 973 | Me | OCH(Et)CH2OMe | 2,4,6-Me3—Ph |
| 974 | Me | OCH2Ph | 2,4,6-Me3—Ph |
| 975 | Me | O-3-pentyl | 2,4,6-Me3—Ph |
| 976 | Me | SEt | 2,4,6-Me3—Ph |
| 977 | Me | S(O)Et | 2,4,6-Me3—Ph |
| 978 | Me | SO2Et | 2,4,6-Me3—Ph |
| 979 | Me | CH(CO2Et)2 | 2,4,6-Me3—Ph |
| 980 | Me | C(Et)(CO2Et)2 | 2,4,6-Me3—Ph |
| 981 | Me | CH(Et)CH2OH | 2,4,6-Me3—Ph |
| 982 | Me | CH(Et)CH2OMe | 2,4,6-Me3—Ph |
| 983 | Me | CONMe2 | 2,4,6-Me3—Ph |
| 984 | Me | COCH3 | 2,4,6-Me3—Ph |
| 985 | Me | CH(OH)CH3 | 2,4,6-Me3—Ph |
| 986 | Me | C(OH)Ph-3-pyridyl | 2,4,6-Me3—Ph |
| 987 | Me | Ph | 2,4,6-Me3—Ph |
| 988 | Me | 2-Ph—Ph | 2,4,6-Me3—Ph |
| 989 | Me | 3-pentyl | 2,4,6-Me3—Ph |
| 990 | Me | cyclobutyl | 2,4,6-Me3—Ph |
| 991 | Me | 3-pyridyl | 2,4,6-Me3—Ph |
| 992 | Me | CH(Et)CH2CONMe2 | 2,4,6-Me3—Ph |
| 993 | Me | CH(Et)CH2CH2NMe2 | 2,4,6-Me3—Ph |
| 994 | Me | NHCH(CH2OMe)2 | 2,4-Me2—Ph |
| 995 | Me | N(CH2CH2OMe)2 | 2,4-Me2—Ph |
| 996 | Me | NHCH(Et)CH2OMe | 2,4-Me2—Ph |
| 997 | Me | NH-3-pentyl | 2,4-Me2—Ph |
| 998 | Me | NEt2 | 2,4-Me2—Ph |
| 999 | Me | N(CH2CN)2 | 2,4-Me2—Ph |
| 1000 | Me | NHCH(Me)CH2OMe | 2,4-Me2—Ph |
| 1001 | Me | OCH(Et)CH2OMe | 2,4-Me2—Ph |
| 1002 | Me | NPr-c-C3H5 | 2,4-Me2—Ph |
| 1003 | Me | NHCH(Me)CH2NMe2 | 2,4-Me2—Ph |
| 1004 | Me | N(c-C3H5)CH2CH2CN | 2,4-Me2—Ph |
| 1005 | Me | N(Pr)CH2CH2CN | 2,4-Me2—Ph |
| 1006 | Me | N(Bu)CH2CH2CN | 2,4-Me2—Ph |
| 1007 | Me | NHCHPr2 | 2,4-Me2—Ph |
| 1008 | Me | NEtBu | 2,4-Me2—Ph |
| 1009 | Me | NPr(CH2-c-C3H5) | 2,4-Me2—Ph |
| 1010 | Me | NH-3-heptyl | 2,4-Me2—Ph |
| 1011 | Me | NEt2 | 2,4-Me2—Ph |
| 1012 | Me | NHCH(CH2OEt)2 | 2,4-Me2—Ph |
| 1013 | Me | NH-3-pentyl | 2,4-Me2—Ph |
| 1014 | Me | NMePh | 2,4-Me2—Ph |
| 1015 | Me | NPr2 | 2,4-Me2—Ph |
| 1016 | Me | NH-3-hexyl | 2,4-Me2—Ph |
| 1017 | Me | morpholino | 2,4-Me2—Ph |
| 1018 | Me | N(CH2Ph)CH2CH2OMe | 2,4-Me2—Ph |
| 1019 | Me | NHCH(CH2Ph)CH2OMe | 2,4-Me2—Ph |
| 1020 | Me | NH-4-tetrahydropyranyl | 2,4-Me2—Ph |
| 1021 | Me | NH-cyclopentyl | 2,4-Me2—Ph |
| 1022 | Me | NHCH(CH2OMe)2 | 2-Me-4-MeO—Ph |
| 1023 | Me | N(CH2CH2OMe)2 | 2-Me-4-MeO—Ph |

TABLE 6-continued

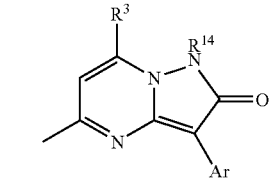

| Ex. | R14 | R3 | Ar |
|---|---|---|---|
| 1024 | Me | NHCH(Et)CH2OMe | 2-Me-4-MeO—Ph |
| 1025 | Me | N(Pr)CH2CH2CN | 2-Me-4-MeO—Ph |
| 1026 | Me | OCH(Et)CH2OMe | 2-Me-4-MeO—Ph |
| 1027 | Me | NHCH(CH2OMe)2 | 2-Br-4-MeO—Ph |
| 1028 | Me | N(CH2CH2OMe)2 | 2-Br-4-MeO—Ph |
| 1029 | Me | NHCH(Et)CH2OMe | 2-Br-4-MeO—Ph |
| 1030 | Me | N(Pr)CH2CH2CN | 2-Br-4-MeO—Ph |
| 1031 | Me | OCH(Et)CH2OMe | 2-Br-4-MeO—Ph |
| 1032 | Me | NHCH(CH2OMe)2 | 2-Me-4-NMe2—Ph |
| 1033 | Me | N(CH2CH2OMe)2 | 2-Me-4-NMe2—Ph |
| 1034 | Me | NHCH(Et)CH2OMe | 2-Me-4-NMe2—Ph |
| 1035 | Me | N(Pr)CH2CH2CN | 2-Me-4-NMe2—Ph |
| 1036 | Me | OCH(Et)CH2OMe | 2-Me-4-NMe2—Ph |
| 1037 | Me | NHCH(CH2OMe)2 | 2-Br-4-NMe2—Ph |
| 1038 | Me | N(CH2CH2OMe)2 | 2-Br-4-NMe2—Ph |
| 1039 | Me | NHCH(Et)CH2OMe | 2-Br-4-NMe2—Ph |
| 1040 | Me | N(Pr)CH2CH2CN | 2-Br-4-NMe2—Ph |
| 1041 | Me | OCH(Et)CH2OMe | 2-Br-4-NMe2—Ph |
| 1042 | Me | NHCH(CH2OMe)2 | 2-Br-4-i-Pr—Ph |
| 1043 | Me | N(CH2CH2OMe)2 | 2-Br-4-i-Pr—Ph |
| 1044 | Me | NHCH(Et)CH2OMe | 2-Br-4-i-Pr—Ph |
| 1045 | Me | N(Pr)CH2CH2CN | 2-Br-4-i-Pr—Ph |
| 1046 | Me | OCH(Et)CH2OMe | 2-Br-4-i-Pr—Ph |
| 1047 | Me | NHCH(CH2OMe)2 | 2-Br-4-Me—Ph |
| 1048 | Me | N(CH2CH2OMe)2 | 2-Br-4-Me—Ph |
| 1049 | Me | NHCH(Et)CH2OMe | 2-Br-4-Me—Ph |
| 1050 | Me | N(Pr)CH2CH2CN | 2-Br-4-Me—Ph |
| 1051 | Me | OCH(Et)CH2OMe | 2-Br-4-Me—Ph |
| 1052 | Me | NHCH(CH2OMe)2 | 2-Me-4-Br—Ph |
| 1053 | Me | N(CH2CH2OMe)2 | 2-Me-4-Br—Ph |
| 1054 | Me | NHCH(Et)CH2OMe | 2-Me-4-Br—Ph |
| 1055 | Me | N(Pr)CH2CH2CN | 2-Me-4-Br—Ph |
| 1056 | Me | OCH(Et)CH2OMe | 2-Me-4-Br—Ph |
| 1057 | Me | NHCH(CH2OMe)2 | 2-Cl-4,6-Me2—Ph |
| 1058 | Me | N(CH2CH2OMe)2 | 2-Cl-4,6-Me2—Ph |
| 1059 | Me | NHCH(CH2OMe)2 | 4-Br-2,6-(Me)2—Ph |
| 1060 | Me | N(CH2CH2OMe)2 | 4-Br-2,6-(Me)2—Ph |
| 1061 | Me | NHCH(CH2OMe)2 | 4-i-Pr-2-SMe—Ph |
| 1062 | Me | N(CH2CH2OMe)2 | 4-i-Pr-2-SMe—Ph |
| 1063 | Me | NHCH(CH2OMe)2 | 2-Br-4-CF3—Ph |
| 1064 | Me | N(CH2CH2OMe)2 | 2-Br-4-CF3—Ph |
| 1065 | Me | NHCH(CH2OMe)2 | 2-Br-4,6-(MeO)2—Ph |
| 1066 | Me | N(CH2CH2OMe)2 | 2-Br-4,6-(MeO)2—Ph |
| 1067 | Me | NHCH(CH2OMe)2 | 2-Cl-4,6-(MeO)2—Ph |
| 1068 | Me | N(CH2CH2OMe)2 | 2-Cl-4,6-(MeO)2—Ph |
| 1069 | Me | NHCH(CH2OMe)2 | 2,6-(Me)2-4-SMe—Ph |
| 1070 | Me | N(CH2CH2OMe)2 | 2,6-(Me)2-4-SMe—Ph |
| 1071 | Me | NHCH(CH2OMe)2 | 4-(COMe)-2-Br—Ph |
| 1072 | Me | N(CH2CH2OMe)2 | 4-(COMe)-2-Br—Ph |
| 1073 | Me | NHCH(CH2OMe)2 | 2,4,6-Me3-pyrid-3-yl |
| 1074 | Me | N(CH2CH2OMe)2 | 2,4,6-Me3-pyrid-3-yl |
| 1075 | Me | NHCH(CH2OMe)2 | 2,4-(Br)—Ph |
| 1076 | Me | N(CH2CH2OMe)2 | 2,4-(Br)—Ph |
| 1077 | Me | NHCH(CH2OMe)2 | 4-i-Pr-2-SMe—Ph |
| 1078 | Me | N(CH2CH2OMe)2 | 4-i-Pr-2-SMe—Ph |
| 1079 | Me | NHCH(CH2OMe)2 | 4-i-Pr-2-SO2Me—Ph |
| 1080 | Me | N(CH2CH2OMe)2 | 4-i-Pr-2-SO2Me—Ph |
| 1081 | Me | NHCH(CH2OMe)2 | 2,6-(Me)2-4-SMe—Ph |
| 1082 | Me | N(CH2CH2OMe)2 | 2,6-(Me)2-4-SMe—Ph |
| 1083 | Me | NHCH(CH2OMe)2 | 2,6-(Me)2-4-SO2Me—Ph |
| 1084 | Me | N(CH2CH2OMe)2 | 2,6-(Me)2-4-SO2Me—Ph |
| 1085 | Me | NHCH(CH2OMe)2 | 2-I-4-i-Pr—Ph |
| 1086 | Me | N(CH2CH2OMe)2 | 2-I-4-i-Pr—Ph |
| 1087 | Me | NHCH(CH2OMe)2 | 2-Br-4-N(Me)2-6-MeO—Ph |
| 1088 | Me | N(CH2CH2OMe)2 | 2-Br-4-N(Me)2-6-MeO—Ph |
| 1089 | Me | NEt2 | 2-Br-4-MeO—Ph |
| 1090 | Me | NH-3-pentyl | 2-Br-4-MeO—Ph |
| 1091 | Me | NHCH(CH2OMe)2 | 2-CN-4-Me—Ph |

TABLE 6-continued

![structure: pyrazolo-pyrimidinone with R3, R14, Ar substituents]

| Ex. | R14 | R3 | Ar |
|---|---|---|---|
| 1092 | Me | N(c-C3H5)CH2CH2CN | 2,4,6-Me3—Ph |
| 1093 | Me | NHCH(CH2CH2OMe)CH2OMe | 2-Me-4-Br—Ph |
| 1094 | Me | NHCH(CH2OMe)2 | 2,5-Me2-4-MeO—Ph |
| 1095 | Me | N(CH2CH2OMe)2 | 2,5-Me2-4-MeO—Ph |
| 1096 | Me | NH-3-pentyl | 2,5-Me2-4-MeO—Ph |
| 1097 | Me | NEt2 | 2,5-Me2-4-MeO—Ph |
| 1098 | Me | NHCH(CH2OMe)2 | 2-Cl-4-MePh |
| 1099 | Me | NCH(Et)CH2OMe | 2-Cl-4-MePh |
| 1100 | Me | N(CH2CH2OMe)2 | 2-Cl-4-MePh |
| 1101 | Me | (S)-NHCH(CH2CH2OMe)CH2OMe | 2-Cl-4-MePh |
| 1102 | Me | N(c-C3H5)CH2CH2CN | 2,5-Me2-4-MeOPh |
| 1103 | Me | NEt2 | 2-Me-4-MeOPh |
| 1104 | Me | OEt | 2-Me-4-MeOPh |
| 1105 | Me | (S)-NHCH(CH2CH2OMe)CH2OMe | 2-Me-4-MeOPh |
| 1106 | Me | N(c-C3H5)CH2CH2CN | 2-Me-4-MeOPh |
| 1107 | Me | NHCH(CH2CH2OEt)2 | 2-Me-4-MeOPh |
| 1108 | Me | N(c-C3H5)CH2CH2CN | 2,4-Cl2—Ph |
| 1109 | Me | NEt2 | 2-Me-4-ClPh |
| 1110 | Me | NH-3-pentyl | 2-Me-4-ClPh |
| 1111 | Me | N(CH2CH2OMe)2 | 2-Me-4-ClPh |
| 1112 | Me | NHCH(CH2OMe)2 | 2-Me-4-ClPh |
| 1113 | Me | NEt2 | 2-Me-4-ClPh |
| 1114 | Me | NEt2 | 2-Cl-4-MePh |
| 1115 | Me | NH-3-pentyl | 2-Cl-4-MePh |
| 1116 | Me | NHCH(CH2OMe)2 | 2-Cl-4-MeOPh |
| 1117 | Me | N(CH2CH2OMe)2 | 2-Cl-4-MeOPh |
| 1118 | Me | NHCH(Et)CH2OMe | 2-Cl-4-MeOPh |
| 1119 | Me | N(c-Pr)CH2CH2CN | 2-Cl-4-MeOPh |
| 1120 | Me | NEt2 | 2-Cl-4-MeOPh |
| 1121 | Me | NH-3-pentyl | 2-Cl-4-MeOPh |
| 1122 | Me | NHCH(Et)CH2CH2OMe | 2-Cl-4-MeOPh |
| 1123 | Me | NHCH(Et)CH2CH2OMe | 2-Cl-4-MeOPh |
| 1124 | Me | NHCH(Me)CH2CH2OMe | 2-Cl-4-MeOPh |
| 1125 | Me | NHCH(Et)CH2CH2OMe | 2-Br-4-MeOPh |
| 1126 | Me | NHCH(Me)CH2CH2OMe | 2-Br-4-MeOPh |
| 1127 | Me | NHCH(Et)CH2CH2OMe | 2-Me-4-MeOPh |
| 1128 | Me | NHCH(Me)CH2CH2OMe | 2-Me-4-MeOPh |
| 1129 | Me | NHCH(CH2OMe)2 | 2-Cl-4,5-(MeO)2Ph |
| 1130 | Me | N(CH2CH2OMe)2 | 2-Cl-4,5-(MeO)2Ph |
| 1131 | Me | NHCH(Et)CH2OMe | 2-Cl-4,5-(MeO)2Ph |
| 1132 | Me | N(c-Pr)CH2CH2CN | 2-Cl-4,5-(MeO)2Ph |
| 1133 | Me | NEt2 | 2-Cl-4,5-(MeO)2Ph |
| 1134 | Me | NH-3-pentyl | 2-Cl-4,5-(MeO)2Ph |
| 1135 | Me | NHCH(Et)CH2CH2OMe | 2-Cl-4,5-(MeO)2Ph |
| 1136 | Me | NHCH(Me)CH2CH2OMe | 2-Cl-4,5-(MeO)2Ph |
| 1137 | Me | NHCH(CH2OMe)2 | 2-Br-4,5-(MeO)2Ph |
| 1138 | Me | N(CH2CH2OMe)2 | 2-Br-4,5-(MeO)2Ph |
| 1139 | Me | NHCH(Et)CH2OMe | 2-Br-4,5-(MeO)2Ph |
| 1140 | Me | N(c-Pr)CH2CH2CN | 2-Br-4,5-(MeO)2Ph |
| 1141 | Me | NEt2 | 2-Br-4,5-(MeO)2Ph |
| 1142 | Me | NH-3-pentyl | 2-Br-4,5-(MeO)2Ph |
| 1143 | Me | NHCH(CH2OMe)2 | 2-Cl-4,6-(MeO)2Ph |
| 1144 | Me | N(CH2CH2OMe)2 | 2-Cl-4,6-(MeO)2Ph |
| 1145 | Me | NEt2 | 2-Cl-4,6-(MeO)2Ph |
| 1146 | Me | NH-3-pentyl | 2-Cl-4,6-(MeO)2Ph |
| 1147 | Me | NHCH(CH2OMe)2 | 2-Me-4,6-(MeO)2Ph |
| 1148 | Me | N(CH2CH2OMe)2 | 2-Me-4,6-(MeO)2Ph |
| 1149 | Me | NHCH(Et)CH2OMe | 2-Me-4,6-(MeO)2Ph |
| 1150 | Me | NEt2 | 2-Me-4,6-(MeO)2Ph |
| 1151 | Me | NH-3-pentyl | 2-Me-4,6-(MeO)2Ph |
| 1152 | Me | NHCH(Et)CH2CH2OMe | 2-Me-4-MeOPh |
| 1153 | Me | NHCH(Me)CH2CH2OMe | 2-Me-4-MeOPh |
| 1154 | Me | NHCH(CH2OMe)2 | 2-MeO-4-MePh |
| 1155 | Me | N(CH2CH2OMe)2 | 2-MeO-4-MePh |
| 1156 | Me | NHCH(Et)CH2OMe | 2-MeO-4-MePh |
| 1157 | Me | N(c-Pr)CH2CH2CN | 2-MeO-4-MePh |
| 1158 | Me | NEt2 | 2-MeO-4-MePh |
| 1159 | Me | NH-3-pentyl | 2-MeO-4-MePh |
| 1160 | Me | NHCH(Et)CH2CH2OMe | 2-MeO-4-MePh |
| 1161 | Me | NHCH(Me)CH2CH2OMe | 2-MeO-4-MePh |
| 1162 | Me | NHCH(CH2OMe)2 | 2-MeO-4-MePh |
| 1163 | Me | N(CH2CH2OMe)2 | 2-MeO-4-MePh |
| 1164 | Me | NHCH(Et)CH2OMe | 2-MeO-4-MePh |
| 1165 | Me | N(c-Pr)CH2CH2CN | 2-MeO-4-MePh |
| 1166 | Me | NEt2 | 2-MeO-4-MePh |
| 1167 | Me | NH-3-pentyl | 2-MeO-4-MePh |
| 1168 | Me | NHCH(CH2OMe)2 | 2-MeO-4-ClPh |
| 1169 | Me | N(CH2CH2OMe)2 | 2-MeO-4-ClPh |
| 1170 | Me | NHCH(Et)CH2OMe | 2-MeO-4-ClPh |
| 1171 | Me | NEt2 | 2-MeO-4-ClPh |
| 1172 | Me | NH-3-pentyl | 2-MeO-4-ClPh |

Utility

CRF-R1 Receptor Binding Assay for the Evaluation of Biological Activity

The following is a description of the isolation of cell membranes containing cloned human CRF-R1 receptors for use in the standard binding assay as well as a description of the assay itself.

Messenger RNA was isolated from human hippocampus. The mRNA was reverse transcribed using oligo (dt) 12–18 and the coding region was amplified by PCR from start to stop codons. The resulting PCR fragment was cloned into the EcoRV site of pGEMV, from whence the insert was reclaimed using XhoI+XbaI and cloned into the XhoI+XbaI sites of vector pm3ar (which contains a CMV promoter, the SV40 't' splice and early poly A signals, an Epstein-Barr viral origin of replication, and a hygromycin selectable marker). The resulting expression vector, called phchCRFR was transfected in 293EBNA cells and cells retaining the episome were selected in the presence of 400 μM hygromycin. Cells surviving 4 weeks of selection in hygromycin were pooled, adapted to growth in suspension and used to generate membranes for the binding assay described below. Individual aliquots containing approximately $1 \times 10^8$ of the suspended cells were then centrifuged to form a pellet and frozen.

For the binding assay a frozen pellet described above containing 293EBNA cells transfected with hCRFR1 receptors is homogenized in 10 ml of ice cold tissue buffer (50 mM HEPES buffer pH 7.0, containing 10 mM MgCl2, 2 mM EGTA, 1 μg/l aprotinin, 1 μg/ml leupeptin and 1 μg/ml pepstatin). The homogenate is centrifuged at 40,000×g for 12 min and the resulting pellet rehomogenized in 10 ml of tissue buffer. After another centrifugation at 40,000×g for 12 min, the pellet is resuspended to a protein concentration of 360 μg/ml to be used in the assay.

Binding assays are performed in 96 well plates; each well having a 300 μl capacity. To each well is added 50 μl of test drug dilutions (final concentration of drugs range from $10^{-10}$–$10^{-5}$ M), 100 μl of $^{125}$I-ovine-CRF ($^{125}$I-o-CRF) (final concentration 150 pM) and 150 μl of the cell homogenate described above. Plates are then allowed to incubate at room temperature for 2 hours before filtering the incubate over GF/F filters (presoaked with 0.3% polyethyleneimine) using an appropriate cell harvester. Filters are rinsed 2 times with ice cold assay buffer before removing individual filters and assessing them for radioactivity on a gamma counter.

Curves of the inhibition of $^{125}$I-o-CRF binding to cell membranes at various dilutions of test drug are analyzed by the iterative curve fitting program LIGAND [P. J. Munson and D. Rodbard, *Anal. Biochem.* 107:220 (1980), which provides Ki values for inhibition which are then used to assess biological activity.

A compound is considered to be active if it has a $K_i$ value of less than about 10000 nM for the inhibition of CRF.

Inhibition of CRF-Stimulated Adenylate Cyclase Activity

Inhibition of CRF-stimulated adenylate cyclase activity can be performed as described by G. Battaglia et al. *Synapse* 1:572 (1987). Briefly, assays are carried out at 37° C. for 10 min in 200 ml of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/ml phosphocreatine kinase, 5 mM creatine phosphate, 100 mM guanosine 5'-triphosphate, 100 nM oCRF, antagonist peptides (concentration range $10^{-9}$ to $10^{-6m}$) and 0.8 mg original wet weight tissue (approximately 40–60 mg protein). Reactions are initiated by the addition of 1 mM ATP/$^{32}$P]ATP (approximately 2–4 mCi/tube) and terminated by the addition of 100 ml of 50 mM Tris-HCL, 45 mM ATP and 2% sodium dodecyl sulfate. In order to monitor the recovery of cAMP, 1 μl of [$^3$H]cAMP (approximately 40,000 dpm) is added to each tube prior to separation. The separation of [$^{32}$P]cAMP from [$^{32}$P]ATP is performed by sequential elution over Dowex and alumina columns.

In vivo Biological Assay

The in vivo activity of the compounds of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn *Brain Research Reviews* 15:71 (1990).

Compounds may be tested in any species of rodent or small mammal.

Compounds of this invention have utility in the treatment of inbalances associated with abnormal levels of corticotropin releasing factor in patients suffering from depression, affective disorders, and/or anxiety.

Compounds of this invention can be administered to treat these abnormalities by means that produce contact of the active agent with the agent's site of action in the body of a mammal. The compounds can be administered by any conventional means available for use in conjunction with pharmaceuticals either as individual therapeutic agent or in combination of therapeutic agents. They can be administered alone, but will generally be administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugarcoated or film-coated to mask any unpleasant taste, or used to protect the active ingredients from the atmosphere, or to allow selective disintegration of the tablet in the gastrointestinal tract.

Liquid dose forms for oral administration can contain coloring or flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

Although the present invention has been described and exemplified in terms of certain preferred embodiments, other embodiments will be apparent to those skilled in the art. The invention is, therefore, not limited to the particular embodiments described and exemplified, but is capable of modification or variation without departing from the spirit of the invention, the full scope of which is delineated by the appended claims.

What is claimed is:

1. A method of treating supranuclear palsy in mammals comprising administering to the mammal a therapeutically effective amount of a compound of Formula (2):

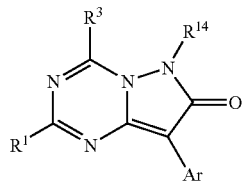

and isomers thereof, stereoisomeric forms thereof, or mixtures of stereoisomeric forms thereof, and pharmaceutically acceptable salt forms thereof, wherein:
Ar is 2,3-dihydrobenzofuranyl;
$R^1$ is CN;
$R^1$ is H; and
$R^{14}$ is $C_3$–$C_{10}$ alkynyl.

* * * * *